US012564645B2

(12) United States Patent
Boeglin et al.

(10) Patent No.: US 12,564,645 B2
(45) Date of Patent: Mar. 3, 2026

(54) METHODS FOR TREATMENT OF METHYLMALONIC ACIDEMIA

(71) Applicant: Translate Bio, Inc., Lexington, MA (US)

(72) Inventors: Lianne Boeglin, Lexington, MA (US); Christian Cobaugh, Lexington, MA (US); Frank DeRosa, Lexington, MA (US); Michael Heartlein, Lexington, MA (US); Kim Askew, Lexington, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 1177 days.

(21) Appl. No.: 17/275,803

(22) PCT Filed: Sep. 13, 2019

(86) PCT No.: PCT/US2019/051060

§ 371 (c)(1),
(2) Date: Mar. 12, 2021

(87) PCT Pub. No.: WO2020/056294

PCT Pub. Date: Mar. 19, 2020

(65) Prior Publication Data

US 2023/0145188 A1 May 11, 2023

Related U.S. Application Data

(60) Provisional application No. 62/793,221, filed on Jan. 16, 2019, provisional application No. 62/731,481, filed on Sep. 14, 2018.

(51) Int. Cl.

| | |
|---|---|
| ***A61K 48/00*** | (2006.01) |
| ***A61K 9/1271*** | (2025.01) |
| ***A61P 3/00*** | (2006.01) |
| ***C12N 15/52*** | (2006.01) |
| ***C12N 15/88*** | (2006.01) |

(52) U.S. Cl.

CPC .......... *A61K 48/005* (2013.01); *A61K 9/1271* (2013.01); *A61P 3/00* (2018.01); *C12N 15/52* (2013.01); *C12N 15/88* (2013.01); *C12Y 504/99002* (2013.01)

(58) Field of Classification Search

None

See application file for complete search history.

(56) References Cited

U.S. PATENT DOCUMENTS 10,426,738 B2 * 10/2019 Martini .................... A61P 3/00
2009/0263375 A1 * 10/2009 Anderson ............. C07K 16/40 435/7.1
2012/0251618 A1 * 10/2012 Schrum ................ A61K 38/193 536/23.1
2015/0038556 A1 * 2/2015 Heartlein ................ A61P 11/00 514/44 R
2016/0032317 A1 * 2/2016 Rossi .................. C12N 5/0647 435/456

FOREIGN PATENT DOCUMENTS

WO WO-2013151666 A2 * 10/2013 ............ A61K 38/17
WO WO 2014/143884 11/2014
WO WO 2017/106799 6/2017
WO WO-2017106799 A1 * 6/2017 ............ A61K 38/52
WO WO 2019/207060 10/2019

OTHER PUBLICATIONS

Gustafsson et al (Trends in Biotechnology,22(7), 346-353 (Year: 2004).*

An et al Cell Reports 21, 3548-3558, (Year: 2017).*

Grier et al Molecular Therapy, 5, e306, 1-10 (Year: 2016).*

Alton et al., "A randomised, double-blind, placebo-controlled trial of repeated nebulisation of non-viral cystic fibrosis transmembrane conductance regulator (CFTR) gene therapy in patients with cystic fibrosis," Efficacy and Mechanism Evaluation, Jul. 2016, vol. 3, No. 5, ISSN 2050-4365.

An et al.: "Systemic Messenger RNA Therapy as a Treatment for Methylmalonic Acidemia" Cell Reports, vol. 21, No. 12, Dec. 19, 2017 (Dec. 19, 2017), pp. 3548-3558, XP055488589, US ISSN: 2211-1247, DOI.

Andries et al.: "N-methylpseudouridine-incorporated mRNA out-performs pseudouridine-incorporated mRNA by providing enhanced protein expression and reduced immunogenicity in mammalian cell lines and mice." (2015, J Controlled Release 217, 337-344).

International Search Report for PCT/US2019/051 060, 5 pages, (dated Dec. 19, 2019).

Kariko et al.: "Incorporation of pseudouridine into mRNA yields superior nonimmunogenic vector with increased translational capacity and biological stability." (2008, Mol Ther. 16(11).

Xiong et al.: "Biomedical applications of mRNA nanomedicine," Nano Research, Tsinghua University Press, CN, vol. 11, No. 10, Jul. 27, 2018 (Jul. 27, 2018), pp. 5281-5309, XP036607492, ISSN: 1998-0124, DOI: 10.1007/S12274-018-2146-1.

* cited by examiner

*Primary Examiner* — Anoop K Singh

(74) *Attorney, Agent, or Firm* — LATHROP GPM LLP; James H. Velema, Esq.

(57) ABSTRACT

The present invention provides, among other things, methods and compositions for treating methylmalonic academia (MMA) based on mRNA therapy. The compositions used in treatment of MMA comprise an mRNA comprising a methymalonyl-CoA mutase (MUT) coding sequence and are administered at an effective dose and an administration interval such that at least one symptom or feature of MMA is reduced in intensity, severity, or frequency or has a delayed onset. mRNAs with optimized MUT coding sequences are provided that can be administered without the need for modifying the nucleotides of the mRNA to achieve sustained in vivo function.

14 Claims, 12 Drawing Sheets

Specification includes a Sequence Listing.

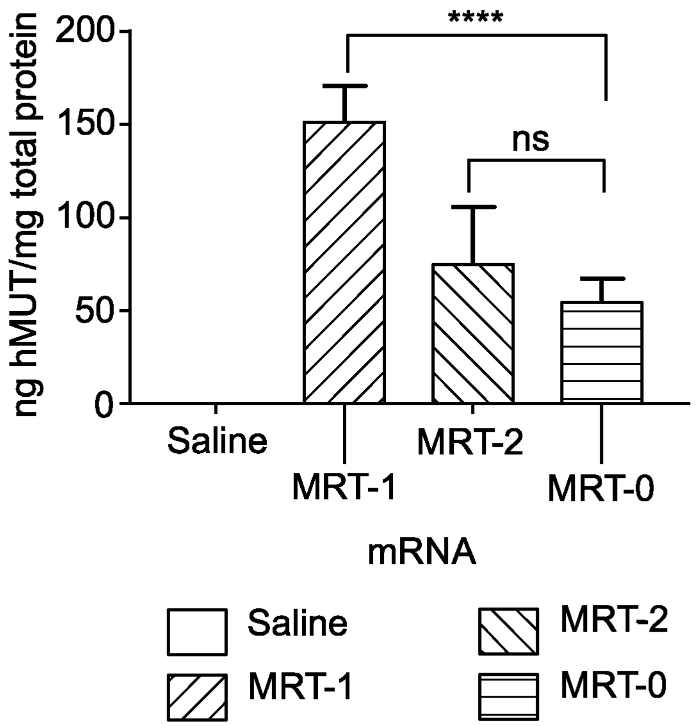
FIG. 1
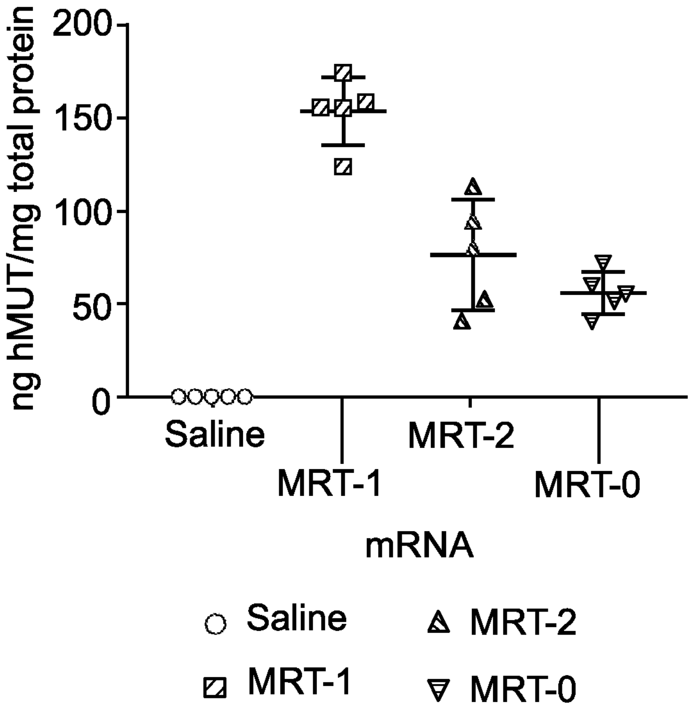

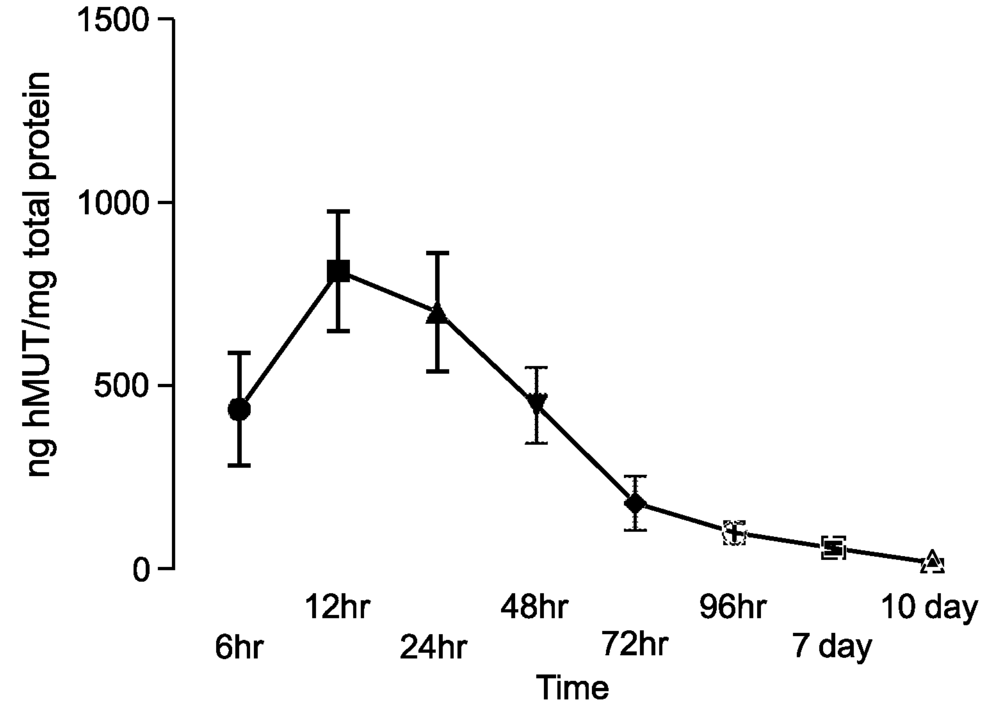
FIG. 3
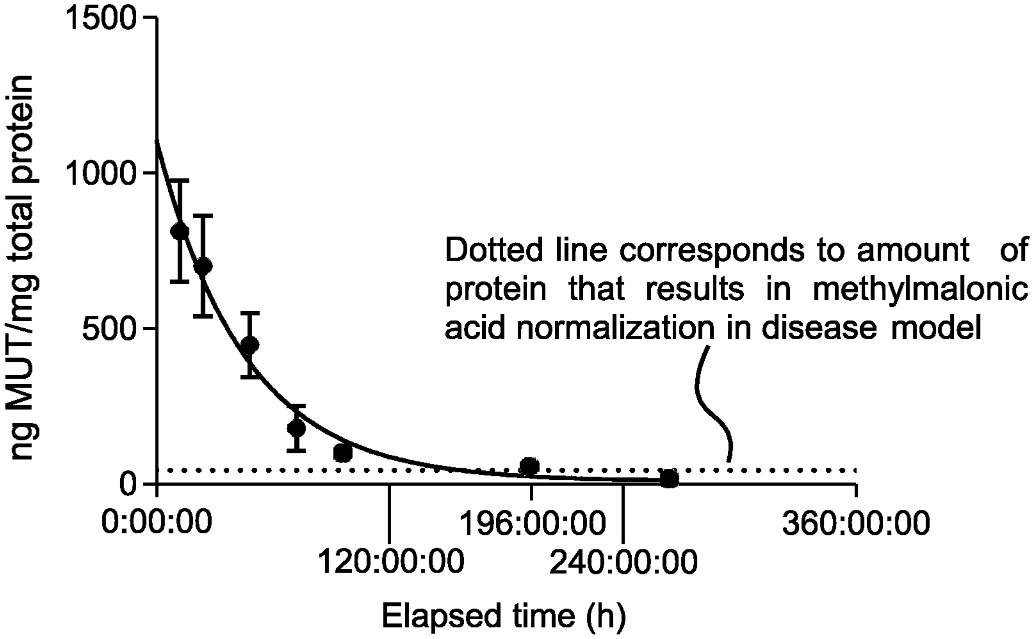

SEQUENCE LISTING

```
<160> NUMBER OF SEQ ID NOS: 14

<210> SEQ ID NO 1
<211> LENGTH: 2253
<212> TYPE: RNA
<213> ORGANISM: Homo sapiens

<400> SEQUENCE: 1

auguuaagag cuaagaauca gcuuuuuuua cuuucaccuc auuaccugag gcagguaaaa      60

gaaucaucag gcuccaggcu cauacagcaa cgacuucuac accagcaaca gccccuucac     120

ccagaauggg cugcccuggc uaaaaagcag cugaaaggca aaaacccaga agaccuaaua     180

uggcacaccc cggaagggau cucuauaaaa cccuuguauu ccaagagaga uacuauggac     240

uuaccugaag aacuuccagg agugaagcca uucacacgug gaccauaucc uaccauguau     300

accuuuaggc ccuggaccau ccgccaguau gcugguuuua guacugugga agaaagcaau     360

aaguucuaua aggacaacau uaaggcuggu cagcagggau uaucaguugc cuuugaucug     420

gcgacacauc guggcuauga uucagacaac ccucgaguuc guggugaugu uggaauggcu     480

ggaguugcua uugacacugu ggaagauacc aaaauucuuu uugauggaau uccuuuagaa     540
```

-continued

```
aaaaugucag uuuccaugac uaugaaugga gcaguuauuc caguucuugc aaauuuuaua    600

guaacuggag aagaacaagg uguaccuaaa gagaagcuua cugguaccau ccaaaaugau    660

auacuaaagg aauuuauggu ucgaaauaca uacauuuuuc cuccagaacc auccaugaaa    720

auuauugcug acauauuuga auauacagca aagcacaugc caaaauuuaa uucaauuuca    780

auuaguggau accauaugca ggaagcaggg gcugaugcca uucuggagcu ggccuauacu    840

uuagcagaug gauuggagua cucuagaacu ggacuccagg cuggccugac aauugaugaa    900

uuugcaccaa gguugucuuu cuucugggga auuggaauga auucuauau ggaaauagca     960

aagaugagag cugguagaag acucugggcu cacuuaauag agaaaauguu ucagccuaaa   1020

aacucaaaau cucuucuucu aagagcacac ugucagacau cuggaugguc acuuacugag   1080

caggaucccu acaauaauau uguccguacu gcaauagaag caauggcagc aguauuugga   1140

gggacucagu cuuugcacac aaauucuuuu gaugaagcuu uggguuugcc aacugugaaa   1200

agugcucgaa uugccaggaa cacacaaauc aucauucaag aagaaucugg gauucccaaa   1260

guggcugauc cuuggggagg uucuuacaug auggaaugyc ucacaaauga uguuuaugau   1320

gcugcuuuaa agcucauuaa ugaaauugaa gaaaugggug gaauggccaa agcuguagcu   1380

gagggaauac cuaaacuucg aauugaagaa ugugcugccc gaagacaagc uagaauagau   1440

ucugguucug aaguaauugu uggaguaaau aaguaccagu uggaaaaaga agacgcugua   1500

gaaguucugg caauugauaa uacuucagug cgaaacaggc agauugaaaa acuuaagaag   1560

aucaaaucca gcagggauca agcuuuggcu gaacguuguc uugcugcacu aaccgaaugu   1620

gcugcuagcg gagauggaaa uauccuggcu cuugcagugg augcaucucg ggcaagaugu   1680

acagugggag aaaucacaga ugcccugaaa aagguauuug gugaacauaa agcgaaugau   1740

cgaaugguga guggagcaua ucgccaggaa uuuggagaaa guaaagagau aacaucugcu   1800

aucaagaggg uucauaaauu cauggaacgu gaaggucgca gaccucgucu ucuuguagca   1860

aaaaugggac aagauggcca ugacagagga gcaaaaguua uugcuacagg auuugcugau   1920

cuugguuuug auguggacau aggcccucuu uuccagacuc cucgugaagu ggcccagcag   1980

gcuguggaug cggaugugca ugcuguggge auaagcaccc ucgcugcugg ucauaaaacc   2040

cuaguuccug aacucaucaa agaacuuaac ucccuuggac ggccagauau ucuugucaug   2100

uguggagggg ugauaccacc ucaggauuau gaauuucugu uugaaguugg uguuuccaau   2160

guauuugguc cugggacucg aauuccaaag gcugccguuc aggugcuuga ugauauugag   2220

aaguguuugg aaaagaagca gcaaucugua uaa                                2253
```

```
<210> SEQ ID NO 2
<211> LENGTH: 2253
<212> TYPE: DNA
<213> ORGANISM: Homo sapiens

<400> SEQUENCE: 2

atgttaagag ctaagaatca gcttttttta ctttcacctc attacctgag gcaggtaaaa     60

gaatcatcag gctccaggct catacagcaa cgacttctac accagcaaca gccccttcac    120

ccagaatggg ctgccctggc taaaaagcag ctgaaaggca aaaacccaga agacctaata    180

tggcacaccc cggaagggat ctctataaaa cccttgtatt ccaagagaga tactatggac    240

ttacctgaag aacttccagg agtgaagcca ttcacacgtg gaccatatcc taccatgtat    300

acctttaggc cctggaccat ccgccagtat gctggtttta gtactgtgga agaaagcaat    360

aagttctata aggacaacat taaggctggt cagcagggat tatcagttgc ctttgatctg    420
```

-continued gcgacacatc gtggctatga ttcagacaac cctcgagttc gtggtgatgt tggaatggct 480
ggagttgcta ttgacactgt ggaagatacc aaaattcttt ttgatggaat tcctttagaa 540
aaaatgtcag tttccatgac tatgaatgga gcagttattc cagttcttgc aaattttata 600
gtaactggag aagaacaagg tgtacctaaa gagaagctta ctggtaccat ccaaaatgat 660
atactaaagg aatttatggt tcgaaataca tacatttttc ctccagaacc atccatgaaa 720
attattgctg acatatttga atatacagca aagcacatgc caaaatttaa ttcaatttca 780
attagtggat accatatgca ggaagcaggg gctgatgcca ttctggagct ggcctatact 840
ttagcagatg gattggagta ctctagaact ggactccagg ctggcctgac aattgatgaa 900
tttgcaccaa ggttgtcttt cttctgggga attggaatga atttctatat ggaaatagca 960
aagatgagag ctggtagaag actctgggct cacttaatag agaaaatgtt tcagcctaaa 1020
aactcaaaat ctcttcttct aagagcacac tgtcagacat ctggatggtc acttactgag 1080
caggatccct acaataatat tgtccgtact gcaatagaag caatggcagc agtatttgga 1140
gggactcagt ctttgcacac aaattctttt gatgaagctt tgggtttgcc aactgtgaaa 1200
agtgctcgaa ttgccaggaa cacacaaatc atcattcaag aagaatctgg gattcccaaa 1260
gtggctgatc cttggggagg ttcttacatg atggaatgtc tcacaaatga tgtttatgat 1320
gctgctttaa agctcattaa tgaaattgaa gaaatgggtg gaatggccaa agctgtagct 1380
gagggaatac ctaaacttcg aattgaagaa tgtgctgccc gaagacaagc tagaatagat 1440
tctggttctg aagtaattgt tggagtaaat aagtaccagt tggaaaaaga agacgctgta 1500
gaagttctgg caattgataa tacttcagtg cgaaacaggc agattgaaaa acttaagaag 1560
atcaaatcca gcagggatca agctttggct gaacgttgtc ttgctgcact aaccgaatgt 1620
gctgctagcg gagatggaaa tatcctggct cttgcagtgg atgcatctcg ggcaagatgt 1680
acagtgggag aaatcacaga tgccctgaaa aaggtatttg gtgaacataa agcgaatgat 1740
cgaatggtga gtggagcata tcgccaggaa tttggagaaa gtaaagagat aacatctgct 1800
atcaagaggg ttcataaatt catggaacgt gaaggtcgca gacctcgtct tcttgtagca 1860
aaaatgggac aagatggcca tgacagagga gcaaaagtta ttgctacagg atttgctgat 1920
cttggttttg atgtggacat aggccctctt ttccagactc ctcgtgaagt ggcccagcag 1980
gctgtggatg cggatgtgca tgctgtgggc ataagcaccc tcgctgctgg tcataaaacc 2040
ctagttcctg aactcatcaa agaacttaac tcccttggac ggccagatat tcttgtcatg 2100
tgtggagggg tgataccacc tcaggattat gaatttctgt ttgaagttgg tgtttccaat 2160
gtatttggtc ctgggactcg aattccaaag gctgccgttc aggtgcttga tgatattgag 2220
aagtgtttgg aaaagaagca gcaatctgta taa 2253

<210> SEQ ID NO 3
<211> LENGTH: 750
<212> TYPE: PRT
<213> ORGANISM: Homo sapiens

<400> SEQUENCE: 3

Met Leu Arg Ala Lys Asn Gln Leu Phe Leu Leu Ser Pro His Tyr Leu
1 5 10 15

Arg Gln Val Lys Glu Ser Ser Gly Ser Arg Leu Ile Gln Gln Arg Leu
20 25 30

Leu His Gln Gln Gln Pro Leu His Pro Glu Trp Ala Ala Leu Ala Lys
35 40 45

-continued

```
Lys Gln Leu Lys Gly Lys Asn Pro Glu Asp Leu Ile Trp His Thr Pro
    50                  55                  60

Glu Gly Ile Ser Ile Lys Pro Leu Tyr Ser Lys Arg Asp Thr Met Asp
65                  70                  75                  80

Leu Pro Glu Glu Leu Pro Gly Val Lys Pro Phe Thr Arg Gly Pro Tyr
                85                  90                  95

Pro Thr Met Tyr Thr Phe Arg Pro Trp Thr Ile Arg Gln Tyr Ala Gly
            100                 105                 110

Phe Ser Thr Val Glu Glu Ser Asn Lys Phe Tyr Lys Asp Asn Ile Lys
        115                 120                 125

Ala Gly Gln Gln Gly Leu Ser Val Ala Phe Asp Leu Ala Thr His Arg
    130                 135                 140

Gly Tyr Asp Ser Asp Asn Pro Arg Val Arg Gly Asp Val Gly Met Ala
145                 150                 155                 160

Gly Val Ala Ile Asp Thr Val Glu Asp Thr Lys Ile Leu Phe Asp Gly
                165                 170                 175

Ile Pro Leu Glu Lys Met Ser Val Ser Met Thr Met Asn Gly Ala Val
            180                 185                 190

Ile Pro Val Leu Ala Asn Phe Ile Val Thr Gly Glu Glu Gln Gly Val
        195                 200                 205

Pro Lys Glu Lys Leu Thr Gly Thr Ile Gln Asn Asp Ile Leu Lys Glu
    210                 215                 220

Phe Met Val Arg Asn Thr Tyr Ile Phe Pro Pro Glu Pro Ser Met Lys
225                 230                 235                 240

Ile Ile Ala Asp Ile Phe Glu Tyr Thr Ala Lys His Met Pro Lys Phe
                245                 250                 255

Asn Ser Ile Ser Ile Ser Gly Tyr His Met Gln Glu Ala Gly Ala Asp
            260                 265                 270

Ala Ile Leu Glu Leu Ala Tyr Thr Leu Ala Asp Gly Leu Glu Tyr Ser
        275                 280                 285

Arg Thr Gly Leu Gln Ala Gly Leu Thr Ile Asp Glu Phe Ala Pro Arg
    290                 295                 300

Leu Ser Phe Phe Trp Gly Ile Gly Met Asn Phe Tyr Met Glu Ile Ala
305                 310                 315                 320

Lys Met Arg Ala Gly Arg Arg Leu Trp Ala His Leu Ile Glu Lys Met
                325                 330                 335

Phe Gln Pro Lys Asn Ser Lys Ser Leu Leu Leu Arg Ala His Cys Gln
            340                 345                 350

Thr Ser Gly Trp Ser Leu Thr Glu Gln Asp Pro Tyr Asn Asn Ile Val
        355                 360                 365

Arg Thr Ala Ile Glu Ala Met Ala Ala Val Phe Gly Gly Thr Gln Ser
    370                 375                 380

Leu His Thr Asn Ser Phe Asp Glu Ala Leu Gly Leu Pro Thr Val Lys
385                 390                 395                 400

Ser Ala Arg Ile Ala Arg Asn Thr Gln Ile Ile Ile Gln Glu Glu Ser
                405                 410                 415

Gly Ile Pro Lys Val Ala Asp Pro Trp Gly Gly Ser Tyr Met Met Glu
            420                 425                 430

Cys Leu Thr Asn Asp Val Tyr Asp Ala Ala Leu Lys Leu Ile Asn Glu
        435                 440                 445

Ile Glu Glu Met Gly Gly Met Ala Lys Ala Val Ala Glu Gly Ile Pro
    450                 455                 460
```

-continued

```
Lys Leu Arg Ile Glu Glu Cys Ala Ala Arg Arg Gln Ala Arg Ile Asp
465                 470                 475                 480

Ser Gly Ser Glu Val Ile Val Gly Val Asn Lys Tyr Gln Leu Glu Lys
                485                 490                 495

Glu Asp Ala Val Glu Val Leu Ala Ile Asp Asn Thr Ser Val Arg Asn
            500                 505                 510

Arg Gln Ile Glu Lys Leu Lys Lys Ile Lys Ser Ser Arg Asp Gln Ala
        515                 520                 525

Leu Ala Glu Arg Cys Leu Ala Ala Leu Thr Glu Cys Ala Ala Ser Gly
    530                 535                 540

Asp Gly Asn Ile Leu Ala Leu Ala Val Asp Ala Ser Arg Ala Arg Cys
545                 550                 555                 560

Thr Val Gly Glu Ile Thr Asp Ala Leu Lys Lys Val Phe Gly Glu His
                565                 570                 575

Lys Ala Asn Asp Arg Met Val Ser Gly Ala Tyr Arg Gln Glu Phe Gly
            580                 585                 590

Glu Ser Lys Glu Ile Thr Ser Ala Ile Lys Arg Val His Lys Phe Met
        595                 600                 605

Glu Arg Glu Gly Arg Arg Pro Arg Leu Leu Val Ala Lys Met Gly Gln
    610                 615                 620

Asp Gly His Asp Arg Gly Ala Lys Val Ile Ala Thr Gly Phe Ala Asp
625                 630                 635                 640

Leu Gly Phe Asp Val Asp Ile Gly Pro Leu Phe Gln Thr Pro Arg Glu
                645                 650                 655

Val Ala Gln Gln Ala Val Asp Ala Asp Val His Ala Val Gly Ile Ser
            660                 665                 670

Thr Leu Ala Ala Gly His Lys Thr Leu Val Pro Glu Leu Ile Lys Glu
        675                 680                 685

Leu Asn Ser Leu Gly Arg Pro Asp Ile Leu Val Met Cys Gly Gly Val
    690                 695                 700

Ile Pro Pro Gln Asp Tyr Glu Phe Leu Phe Glu Val Gly Val Ser Asn
705                 710                 715                 720

Val Phe Gly Pro Gly Thr Arg Ile Pro Lys Ala Ala Val Gln Val Leu
                725                 730                 735

Asp Asp Ile Glu Lys Cys Leu Glu Lys Lys Gln Gln Ser Val
            740                 745                 750
```

<210> SEQ ID NO 4
<211> LENGTH: 2253
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 4

```
augcuuaggg caaagaauca acucuuucug cugagcccac acuauuugcg ccaggugaaa      60

gagagcuccg gcucaaggcu gauccagcag cgucuuuugc aucagcagca gccacugcac     120

ccggaauggg ccgcucucgc gaagaagcag cugaagggaa agaacccgga agaucugauc     180

uggcacacuc cggagggaau cucaaucaag ccacuguacu cuaagagaga caccauggac     240

cuucccgaag aacugcccgg ggugaagccc uucacccggg gaccguaccc gaccauguac     300

accuuuagac cguggacgau ccgccaguac gcaggcuucu cgacggucga agaaagcaac     360

aaauucuaua aagacaacau uaaggccgga caacagggac uguccgucgc auucgaccuc     420
```

gccacccacc gcggauacga uucggacaau ccaaggguga gaggugacgu cggaauggcc 480
ggaguggcua uugauaccgu ggaggacacg aagauccugu ucgacggcau ccccuuggag 540
aagauguccg ugagcaugac uaugaauggc gcugugauuc cugugcucgc caacuucauc 600
gugaccggag aggaacaagg cgugccgaag gaaaagcuca cuggcacuau ccaaaacgac 660 aucccucaaag aauucauggu ccgcaacacu uacauuuuuc cucccgaacc uucgaugaag 720
aucaucgccg auaucuuuga guacacggca aaacacaugc cgaaguucaa uucgaucucg 780
aucuccggau accauaugca agaggcuggg gccgacgcga uccucgaacu ggcuuacacc 840
cuggccgacg gacuggaaua cucacgcacu gggcugcagg ccggucugac caucgacgag 900
uucgcgccga gacuguccuu cuucuggggc auugguauga acuucuacau ggagaucgcc 960
aaaaugcgag caggccgcag gcucugggca caccucaucg agaaaauguu ccagccgaag 1020
aauucuaagu cgcuccugcu gcgcgcccac ugccagacua gcggauggag cuugacugaa 1080
caggacccgu acaacaauau cgugcggacu gccaucgaag cgauggccgc aguguucgga 1140
ggaacccagu cacugcauac caacagcuuu gacgaagccc ucggcuugcc aacugugaaa 1200
agcgcgcgga ucgcaaggaa cacucagauc auuauccaag aagaauccgg uaucccuaag 1260
guggccgauc cguggggcgg auccuacaug auggagugcc ugaccaauga cgucuacgau 1320
gccgcgcuga aacugaucaa cgagauugaa gagaugggag gaauggcuaa ggccguugca 1380
gaagggaucc cgaagcugcg gauugaggaa ugugcggccc ggcgccaggc ccgaaucgau 1440
agcggcucag aaguuaucgu gggugucaac aaguaccagc uugagaagga agaugcagug 1500
gagguccucg caauugauaa uaccuccguc cggaauagac aaaucgaaaa acugaaaaag 1560
aucaagagcu cccgcgacca agcccuggcg gaaagaugcu uggcggcccu gaccgagugc 1620
gcugccucag gcgacggaaa cauccuggca cucgcagucg augccucgcg ggcgcgcugc 1680
acugugggug agaucaccga cgcccucaag aaggucuuug gagagcauaa ggcgaacgac 1740 agaaugggugu cgggagcaua ccggcaggag uucggcgaau ccaaagagau cacuucggcg 1800
aucaaacgcg ugcacaaguu cauggaacgg gaggggcggc ggccgcgccu ucucguggcg 1860 aagaugggggc aggauggaca ugaccgcgga gcuaagguga ucgccaccgg guucgcugau 1920
cucggguucg acguggacau cggcccucug uuccaaaccc cuagagaagu ggcgcaacaa 1980
gcuguggaug cugaugugca ugcggucgga aucuccaccc ucgcagccgg acauaaaacu 2040
cuggugcccg agcucauaaa ggaacugaac ucgcugggcc ggccagauau ccuggucaug 2100
ugcgguggag ugaucccacc ucaagauuac gaguuccugu uugaagucgg agugucaaac 2160
guguuuggac cgggaacucg caucccaaag gcggccgugc aaguccuuga ugacauugaa 2220
aagugucugg agaaaaagca gcagagcgug uag 2253

<210> SEQ ID NO 5
<211> LENGTH: 2253
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 5
augcugcggg ccaagaacca gcuguuccuc cuuuccccccc acuaccugag acaagucaaa 60
gaauccuccg gaucaagauu gauucagcaa cgccuguugc aucagcaaca gccauugcac 120
ccugaauggg ccgcccuggc uaagaagcag cuuaagggaa agaacccgga agaucugauc 180

-continued uggcacaccc cggaaggcau cucuaucaag ccucuguacu ccaagagaga caccauggau 240
cucccugagg aacugccggg agucaagccu uuuacccgcg guccguaccc uaccauguac 300
acguuccgcc cguggaccau caggcaguac gccggauuca gcacggugga agagagcaac 360
aaguucuaca aggacaacau aaaggccgga cagcagggac uguccguggc cuucgaccug 420
gccacccauc ggggcuauga cucggacaac ccucgcgugc gcggggaugu cggaauggcc 480
ggaguggcga uugacacugu cgaggacacu aagauccugu ucgauggcau uccccuggaa 540
aagauguccg ugagcaugac uaugaacggc gcagugaucc cagugcuggc uaacuucauc 600
gugacuggag aggagcaagg ggugcccaaa gagaagcuga cuggaacuau ccagaacgau 660
auucugaagg aguuuauggu ccggaacacu uacauuuucc cgcccgagcc cucgaugaag 720
aucaucgcgg acauuuucga guacaccgcc aagcauaugc cuaaguucaa cuccaucucg 780
aucuccggau accacaugca ggaagccgga gcggacgcga uccuugaacu ggcguacacu 840
cuggccgaug gccuggaaua cucccgcacg ggcuugcagg ccggucugac caucgacgaa 900
uuugccccgc gguuguccuu cuuuugggga aucggcauga auuucuacau ggaaaucgcc 960
aagaugagag cgggccggag acugugggcc caccugaucg agaagauguu ccagcccaag 1020
aacucgaaaa gccuccuccu gcgggcgcac ugccagaccu ccggaugguc ccugaccgag 1080
caggacccgu acaacaacau cguccgaacc gcuauugagg ccauggccgc cguguuuggg 1140
ggaacucagu cacuccauac uaauuccuuc gaugaagccc uggggcuucc uaccgucaag 1200
agcgcccgga ucgccaggaa uacccagauc aucauucaag aagagucagg caucccuaaa 1260
guggccgacc ccugggggggg aagcuacaug auggaauguu ugaccaacga cgucuacgac 1320
gccgcccuga agcucaucaa cgaaauugaa gaaaugggcg gcauggccaa ggccguggca 1380
gaggggaucc cuaagcugcg gauugaggaa ugcgccgcca gacgccaggc ccgaaucgac 1440
uccgguuccg aagucaucgu gggcgugaac aaguaccagc uggagaagga agaugccgug 1500
gaagugcugg ccauugauaa caccuccgug cgcaaccgcc agaucgaaaa gcugaaaaag 1560
auuaagucgu cgcgcgacca ggcacuggcg gagagaugcc uggcugcacu gaccgagugc 1620
gcggcgucug gggacggcaa uauccuggca cuggcugugg acgcgagccg ggcccgcugc 1680
acugugggag agaucacuga ugcccucaag aaaguguucg gagaacacaa ggccaacgac 1740
agaauggugu cgggggccua ucgccaagaa uucggggagu cgaaggaaau caccagcgcc 1800
auuaagcggg ugcacaaguu cauggaaagg gaaggacgcc ggccacgccu ccugguggca 1860
aagaugggac aggacgguca cgacaggggc gcaaagguca ucgcgaccgg auucgccgac 1920
cucggcuucg auguggacau uggaccccuu uuccaaaccc cucgggaggu cgcccaacaa 1980
gcuguggaug ccgacgugca ugcuguggga auuucgaccc uggccgccgg ucacaagacc 2040
cuggugcccg aacugauuaa ggagcugaac ucacugggaa ggccugauau ucucgugaug 2100
uguggcggag ugaucccgcc gcaagacuac gaauuccugu ucgaagucgg cguguccaac 2160
guguucgggc ccggcacacg gaucccgaaa gccgcggucc aagugcucga ugauauugag 2220
aagugucucg aaaagaaaca gcaguccguc uag 2253

<210> SEQ ID NO 6
<211> LENGTH: 140
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 6
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg 140

<210> SEQ ID NO 7
<211> LENGTH: 105
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 7
cggguggcau cccugugacc ccuccccagu gccucuccug gcccuggaag uugccacucc 60
agugcccacc agccuugucc uaauaaaauu aaguugcauc aagcu 105

<210> SEQ ID NO 8
<211> LENGTH: 105
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 8
ggguggcauc ccugugaccc cuccccagug ccucuccugg cccuggaagu ugccacucca 60
gugcccacca gccuuguccu aauaaaauua aguugcauca aagcu 105

<210> SEQ ID NO 9
<211> LENGTH: 800
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: misc_feature
<222> LOCATION: (1)..(800)
<223> OTHER INFORMATION: This sequence may encompass 300-800 nucleotides

<400> SEQUENCE: 9
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa 800

<210> SEQ ID NO 10
<211> LENGTH: 300
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 10
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300

<210> SEQ ID NO 11
<211> LENGTH: 200
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: misc_feature
<222> LOCATION: (1)..(200)
<223> OTHER INFORMATION: This sequence may encompass 10-200 nucleotides

<400> SEQUENCE: 11
cccccccccc cccccccccc cccccccccc cccccccccc cccccccccc cccccccccc 60
cccccccccc cccccccccc cccccccccc cccccccccc cccccccccc cccccccccc 120
cccccccccc cccccccccc cccccccccc cccccccccc cccccccccc cccccccccc 180
cccccccccc cccccccccc 200

<210> SEQ ID NO 12
<211> LENGTH: 2253
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 12
augcugcggg ccaagaacca gcuguuccug cugagcccuc acuaccugcg gcaggugaag 60
gagagcagcg gcagccggcu gauccagcag cggcugcugc accagcagca gccccugcac 120
cccgaguggg ccgcccuggc caagaagcag cugaagggca agaaccccga ggaccugauc 180
uggcacacgc ccgagggcau cagcaucaag ccccuguaca gcaagcggga caccauggac 240
cugcccgagg agcugcccgg cgugaagccc uucacccggg gccccuaccc caccauguac 300
accuuccggc ccuggaccau ccggcaguac gccggcuuca gcaccgugga ggagagcaac 360
aaguucuaca aggacaacau caaggccggc cagcagggcc ugagcguggc cuucgaccug 420
gccacccacc ggggcuacga cagcgacaac ccacgggugc ggggcgacgu gggcauggcc 480
ggcguggcca ucgacaccgu ggaggacacc aagauccugu ucgacggcau cccucuggag 540
aagaugagcg ugagcaugac caugaacggc gccgugaucc ccgugcuggc caacuucauc 600
gugaccggcg aggagcaggg cgugcccaag gagaagcuga ccggcaccau ccagaacgac 660

-continued

```
auccugaagg aguucauggu gcggaacacc uacaucuucc cucccgagcc cagcaugaag    720

aucaucgccg acaucuucga guacaccgcc aagcacaugc ccaaguucaa cagcaucagc    780

aucagcggcu accacaugca ggaggccggc gccgacgcca uccuggagcu ggccuacacc    840

cuggccgacg gccuggagua cagccggacc ggccugcagg ccggccugac caucgacgag    900

uucgcgcccc ggcugagcuu cuucuggggc aucggcauga acuucuacau ggagaucgcc    960

aagaugcggg ccggccggcg gcugugggcc caccugaucg agaagauguu ccagcccaag   1020

aacagcaaga gccugcugcu gcgggcccac ugccagacca gcggcuggag ccugaccgag   1080

caggaccccu acaacaacau cgugcggacc gccaucgagg ccauggccgc cguguucggc   1140

ggcacccaga gccugcacac caacagcuuc gacgaggccc ugggccugcc caccgugaag   1200

agcgcccgga ucgcccggaa cacccagauc aucauccagg aggagagcgg cauccccaag   1260

guggccgacc ccuggggcgg cagcuacaug auggagugcc ugaccaacga cguguacgac   1320

gccgcccuga agcugaucaa cgagaucgag gagaugggcg gcauggccaa ggccguggcc   1380

gagggcaucc ccaagcugcg gaucgaggag ugcgccgccc ggcggcaggc ccggaucgac   1440

agcggcagcg aggugaucgu gggcgugaac aaguaccagc uggagaagga ggacgccgug   1500

gaggugcugg ccaucgacaa caccagcgug cggaaccggc agaucgagaa gcugaagaag   1560

aucaagagca gccgggacca ggcccuggcc gagcggugcc uggccgcccu gaccgagugc   1620

gccgccagcg gcgacggcaa cauccuggcc cuggccgugg acgccagccg ggcccggugc   1680

accgugggcg agaucaccga cgcccugaag aagguguucg gcgagcacaa ggccaacgac   1740

cggauggaga gcggcgccua ccggcaggag uucggcgaga gcaaggagau caccagcgcc   1800

aucaagcggg ugcacaaguu cauggagcgg gagggccggc ggccccggcu gcugguggcc   1860

aagaugggcc aggacggcca cgaccggggc gccaagguga ucgccaccgg cuucgccgac   1920

cugggcuucg acguggacau cggcccacug uuccagacgc cccgggaggu ggcccagcag   1980

gccguggacg ccgacgugca cgccgugggc gugagcaccc uggccgccgg ccacaagacc   2040

cuggugcccg agcugaucaa ggagcugaac agccugggcc ggcccgacau ccuggugaug   2100

ugcggcggcg ugaucccgcc ccaggacuac gaguuccugu ucgagguggg cgugagcaac   2160

guguucggcc ccggcacccg gaucccccaag gccgccgugc aggugcugga cgacaucgag   2220

aagugccugg agaagaagca gcagagcgug uga                                2253
```

<210> SEQ ID NO 13
<211> LENGTH: 800
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 13

```
aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa aaaaaaaaaa aaaaaaaaaa    420
```

-continued

```
aaaaaaaaaa aaaaaaaaaa aaaaaaaaaa aaaaaaaaaa aaaaaaaaaa aaaaaaaaaa    480

aaaaaaaaaa aaaaaaaaaa aaaaaaaaaa aaaaaaaaaa aaaaaaaaaa aaaaaaaaaa    540

aaaaaaaaaa aaaaaaaaaa aaaaaaaaaa aaaaaaaaaa aaaaaaaaaa aaaaaaaaaa    600

aaaaaaaaaa aaaaaaaaaa aaaaaaaaaa aaaaaaaaaa aaaaaaaaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaaaaa aaaaaaaaaa aaaaaaaaaa aaaaaaaaaa    780

aaaaaaaaaa aaaaaaaaaa                                                800


<210> SEQ ID NO 14
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 14

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa                          100
```

METHODS FOR TREATMENT OF METHYLMALONIC ACIDEMIA

CROSS-REFERENCE TO RELATED APPLICATIONS

This application is a 35 U.S.C. § 371 National Stage Application of International Application No. PCT/US19/51060, filed on Sep. 13, 2019, which claims priority to, and the benefit of, U.S. 62/731,481 filed on Sep. 26, 2019, and U.S. 62/793,221 filed on Jan. 16, 2019, the content of each of which is hereby incorporated by reference in its entirety.

INCORPORATION-BY-REFERENCE OF SEQUENCE LISTING

The present specification makes reference to a Sequence Listing submitted electronically as a .txt file named "MRT-2014US1_SL.txt" on Jun. 9, 2022, and is 27,277 bytes in size. The entire contents of the Sequence Listing are herein incorporated by reference.

BACKGROUND

Methylmalonic acidemia (MMA) is an autosomal recessive metabolic disorder characterized by an inability to convert methylmalonyl-CoA into succinyl-CoA. It is one of the most common forms of organic acidemia, with an incidence of 1 in 50,000 to 1 in 100,000. Symptoms usually present within the first year of life and can result in brain damage, coma and death if left untreated. MMA patients may experience metabolic crises, presenting with poor appetite, vomiting, extreme sleepiness or lack of energy and low muscle tone. MMA is a progressive condition that can lead to learning disabilities, delays in walking and motor skills, abnormal involuntary movements, poor growth, osteoporosis and kidney disease or failure.

The most common cause of MMA is a mutation in the MUT gene that encodes the methylmalonyl-CoA mutase protein. The inability to convert methylmalonyl-CoA into succinyl-CoA results in an accumulation of methylmalonic acid in the blood. Methylmalonic acid is toxic to all types of body cells. Patients lacking the MUT gene have elevated levels of methylmalonic acid in their blood (100-1,000 μmol/L) and urine (1,000-10,000 mmol/mol creatinine).

There is currently no cure for MMA. Patients are treated primarily with a low-protein diet, medications (including B12 injections in the form of hydroxocobalamin or cyanocobalamin) and diet supplementation. For some patients, liver transplantation may be considered. Each patient requires a personalised diet and medication regimen. Gene therapy, and more recently mRNA replacement therapy, have been studied to address the urgent need for new, more effective treatments of MMA.

An et al. (2017, Cell Reports 21, 3548-3558) demonstrate that a 1-methylpseudouridine-substituted, codon-optimized mRNA encoding human methylmalonyl-CoA mutase (hMUT) can be used for in vivo hMUT protein expression in wild type and $Mut^{-/-}$ mice. $Mut^{-/-};^{TgINS\text{-}MCK\text{-}Mut}$ mice were used as a disease model for severe MMA. An et al. demonstrate that treatment of $Mut^{-/-};^{TgINS\text{-}MCK\text{-}Mut}$ mice with hMUT mRNA reduces the methylmalonic acid concentration in plasma and various tissues, prolongs survival and increases body weight relative to untreated controls. An mRNA dose range of 0.2-1.0 mg/kg was shown to be therapeutically useful in $Mut^{-/-};^{TgINS\text{-}MCK\text{-}Mut}$ mice. Weekly dosing with 0.2 mg/kg hMUT mRNA improved survival and resulted in a 62-89% reduction in plasma methylmalonic acid levels relative to untreated $Mut^{-/-};^{TgINS\text{-}MCK\text{-}Mut}$ mice.

It is widely published that nucleobase modifications enhance the properties of mRNA by reducing the immunogenicity and increasing the stability of the RNA molecule. In addition, it has been shown that certain nucleobase modifications have a beneficial effect on translation of the mRNA-encoded protein. For example, Kariko et al. (2008, Mol Ther. 16(11), 1833-1840) observed that pseudouridine-modified mRNA encoding a luciferase reporter gene, when administered to mice at a dose of 0.015-0.150 mg/kg, resulted in luciferase levels that were 12- to 78-fold higher compared to treatment with the corresponding unmodified mRNA. Notably, Andries et al. (2017, J Controlled Release 217, 337-344) demonstrated that luciferase mRNA modified with 1-methylpseudouridine translated 13-fold more than a corresponding pseudouridine-modified mRNA when administered to mice.

These data suggest that modification of mRNA with pseudouridine and, in particular 1-methylpseudouridine, could result in adequate expression of the encoded protein at reduced doses, potentially outweighing the expense of using modified nucleotides in the production of mRNA for therapy. Going against this emerging paradigm, the inventors demonstrate in the present application that unmodified nucleotides can be used to produce mRNA formulations that are non-inferior in an in vivo mouse model.

Specifically, the present application is based on the discovery that various optimisation strategies can result in mRNA constructs that perform similarly to or better than 1-methylpseudouridine-modified mRNA in vivo, both in terms of stability of the mRNA and quantity of the protein expressed from it. Specific optimization steps include extending the length of the poly(A) tail, encapsulating the mRNA in a liposome and codon-optimizing the sequence of the encoded gene.

Codon optimization has previously been used to prepare high-expression constructs of the MUT gene in an effort to provide a gene therapy vector for the treatment of MMA. For example, WO 2014/143884 discloses a codon-optimized MUT gene. This synthetic gene was engineered from the naturally occurring MUT cDNA (NCBI reference sequence NM_000255.3) using OptimumGene™ codon optimization software (Genscript Inc.). For further study, a nucleic acid sequence was selected that had the maximal divergence from the MUT cDNA at the nucleotide level yet retained optimally utilized codons at each position. The codon-optimized gene sequence and its wild-type counterpart were cloned into an expression vector and their expression was compared by transfecting HEK-293 cells. Disappointingly, levels of protein expression from the codon-optimized gene sequence were similar to that of the wild-type gene sequence 48 hours post transfection.

WO 2017/106799 also discloses a codon-optimized MUT gene sequence. No data comparing expression of the codon-optimized gene sequence relative to the wild-type MUT gene sequence are provided. The codon-optimized gene sequence was used to prepare an mRNA that contained 100% 1-methyl-pseudouridine instead of uridine, a 100-nucleotide long poly-A tail (SEQ ID NO: 14) and a Cap1 structure. The resulting mRNA was encapsulated in a liposome.

The inventors discovered that, among other measures, further optimization of the MUT gene sequence can obviate the need to use 100% 1-methyl-pseudouridine to achieve stable and consistently high mRNA expression in vivo.

SUMMARY OF THE INVENTION

The present invention provides, among other things, methods and compositions for use in the treatment of methylmalonic acidemia (MMA).

In one embodiment, the present invention provides methods of treating MMA in a mammal, comprising administering to a subject in need of treatment a composition comprising an mRNA comprising a methylmalonyl-CoA mutase (MUT) coding sequence at an effective dose and an administration level such that the level of at least one symptom or feature associated with MMA is reduced in intensity, severity, or frequency or is delayed in onset, wherein the nucleotides of the mRNA are unmodified. In some embodiments, the mRNA is encapsulated within a liposome. In some embodiments, the MUT coding sequence is codon-optimized.

The present invention also provides a composition comprising an mRNA encoding a codon-optimized methylmalonyl-CoA mutase (MUT) coding sequence, wherein the mRNA is encapsulated within a liposome and the nucleotides of the mRNA are unmodified.

In some embodiments, the liposome comprises one or more cationic lipids, one or more non-cationic lipids, one or more cholesterol-based lipids and one or more PEG-modified lipids. In some embodiments, the composition comprises one or more cationic lipids selected from the group consisting of cKK-E12, OF-02, C12-200, MC3, DLinDMA, DLinkC2DMA, ICE (Imidazol-based), HGT5000, HGT5001, HGT4003, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, DLin-SSDMA, KLin-K-DMA, DLin-K-XTC2-DMA, 3-(4-(bis(2-hydroxydodecyl)amino)butyl)-6-(4-((2-hydroxydodecyl)(2-hydroxyundecyl)amino)butyl)-1,4-dioxane-2,5-dione (Target 23), 3-(5-(bis(2-hydroxydodecyl)amino)pentan-2-yl)-6-(5-((2-hydroxydodecyl)(2-hydroxyundecyl)amino) pentan-2-yl)-1,4-dioxane-2,5-dione (Target 24), ccBene, ML7 and combinations thereof. In some embodiments, the one or more cationic lipids comprise cKK-E12.

In some embodiments, the one or more non-cationic lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero phospho-(1'-rac-glycerol)) and combinations thereof.

In some embodiments, the one or more cholesterol-based lipids are cholesterol and/or PEGylated cholesterol.

In some embodiments, the one or more PEG-modified lipids comprise a poly(ethylene) glycol chain of up to 5 kDa in length covalently attached to a lipid with alkyl chain(s) of C6-C20 length.

In some embodiments, the cationic lipid constitutes about 30-60% of the liposome by molar ratio. In some embodiments, the cationic lipid constitutes about 30%, 40%, 50%, or 60% of the liposome by molar ratio.

In some embodiments, the ratio of cationic lipids:non-cationic lipids:cholesterol lipids:PEGylated lipids is approximately 40:30:20:10 by molar ratio. In some embodiments, the ratio of cationic lipids:non-cationic lipids:cholesterol lipids:PEGylated lipids is approximately 40:30:25:5 by molar ratio. In some embodiments, the ratio of cationic lipids:non-cationic lipids:cholesterol lipids:PEGylated lipids is approximately 40:32:25:3 by molar ratio. In some embodiments, the ratio of cationic lipids:non-cationic lipids:cholesterol lipids:PEGylated lipids is approximately 50:25:20:5 by molar ratio.

In some embodiments, the liposome comprises cKK-E12, DOPE, cholesterol and DMG-PEG2K.

In some embodiments, the liposome has a size of about 80 nm to 200 nm. In some embodiments, the liposome has a size of about 100 nm or less than 100 nm.

In some embodiments, the mRNA is administered at an effective dose ranging from about 0.03-3.0 mg/kg body weight, or 0.03-1.0 mg/kg body weight. In certain embodiments, the mRNA is administered at an effective dose ranging from about 0.1-3.0 mg/kg body weight, or 0.1-1.0 mg/kg body weight.

In some embodiments, the composition is administered intravenously. In other embodiments, the composition is administered subcutaneously.

In some embodiments, the composition is administered once a week, once every two weeks, twice a month or once a month.

In some embodiments, administering of the composition results in MUT expression detectable in liver.

In some embodiments, administering of the composition results in MUT expression in the liver at or above about 100 ng/mg of total protein, or at or above about 150 ng/mg total protein.

In some embodiments, the administering of the composition results in a decreased level of methylmalonic acid level in plasma and/or urine as compared to the baseline methylmalonic acid level before the treatment. In some embodiments, the administering of the composition results in an at least 50% reduction of methylmalonic acid level in plasma and/or urine. In some embodiments, the administering of the composition results in reduction of methylmalonic acid levels to about 200 μmol/L or less, about 100 μmol/L or less or about 50 μmol/L or less in the plasma and/or to about 1000 mmol/mol creatinine or less, 500 mmol/mol creatinine or less or 200 mmol/mol creatinine or less in urine.

In some embodiments, the codon-optimized MUT coding sequence comprises or consists of a nucleic acid sequence 85%, 90%, 95% or 99% identical to SEQ ID NO: 4 or 85%, 90%, 95% or 99% identical to SEQ ID NO: 5. In some embodiments, the mRNA encoding the methylmalonyl-CoA mutase protein comprises SEQ ID NO: 4. In some embodiments, the mRNA encoding the methylmalonyl-CoA mutase protein comprises SEQ ID NO: 5.

In some embodiments, the mRNA encodes a MUT protein with an amino acid sequence that is identical to SEQ ID NO: 3.

In some embodiments, the mRNA comprises the 5' UTR sequence of SEQ ID NO:6 and/or the 3' UTR sequence of SEQ ID NO:7 or SEQ ID NO:8. In some embodiments, the mRNA comprises a 3' poly(A) tail structure that is at least 300 nucleotides long (SEQ ID NO: 10) or is 300-800 nucleotides long £SEQ ID NO: 9).

In some embodiments, the compositions of the invention are for use in a method of treating methylmalonic acidemia (MMA).

The invention also provides a composition comprising an mRNA encoding a methylmalonyl-CoA mutase (MUT) coding sequence at least 85% identical to SEQ ID NO:4 or SEQ ID NO:5. In some embodiments, MUT coding sequence comprising a nucleic acid sequence at least 90%, 95% or 99% identical to SEQ ID NO: 4 or a nucleic acid sequence at least 90%, 95% or 99% identical to SEQ ID NO: 5. In some embodiments, the MUT coding sequence comprises or consists of SEQ ID NO: 4 or SEQ ID NO: 5.

In some embodiments, the mRNA is encapsulated within a liposome for use in treating methylmalonic acidemia (MMA). In some embodiments, the liposome comprises one or more cationic lipids, one or more non-cationic lipids, one or more cholesterol-based lipids and one or more PEG-modified lipids. In some embodiments, the mRNA comprises a 3' poly(A) tail structure that is at least 300 nucleotides long (SEQ ID NO: 10), or 300-800 nucleotides long (SEQ ID NO: 9).

The invention also provides an mRNA comprising in 5'→3' order: a 5' cap structure, a coding sequence at least 85% identical to SEQ ID NO:4 or SEQ ID NO:5, and 3' poly(A) tail structure. In some embodiments, MUT coding sequence comprising a nucleic acid sequence at least 90%, 95% or 99% identical to SEQ ID NO: 4 or a nucleic acid sequence at least 90%, 95% or 99% identical to SEQ ID NO: 5. In some embodiments, the MUT coding sequence comprises or consists of SEQ ID NO: 4 or SEQ ID NO: 5. In some embodiments, the nucleotides of the mRNA are unmodified. In some embodiments, the mRNA comprises a 3' poly(A) tail structure that is at least 300 nucleotides long (SEQ ID NO: 10), or 300-800 nucleotides long (SEQ ID NO: 9).

The invention further provides a nucleic acid comprising a nucleic acid sequence at least 85%, 90%, 95% or 99% identical to SEQ ID NO:4 or SEQ ID NO:5. The invention also provides a nucleic acid comprising or consisting of SEQ ID NO:4 or SEQ ID NO: 5.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWINGS

The drawings are for illustration purposes only, not for limitation.

FIG. 1 shows hMUT expression per mg of total protein in mouse livers 24 hours after administration of a 1.0 mg/kg dose of an MRT-1, MRT-2 or MRT-0 formulation, plotted in two different formats.

FIG. 3 shows hMUT expression kinetics following administration of a 1.0 mg/kg dose of an MRT-1, plotted in two different formats.

DEFINITIONS

Figure 2A:
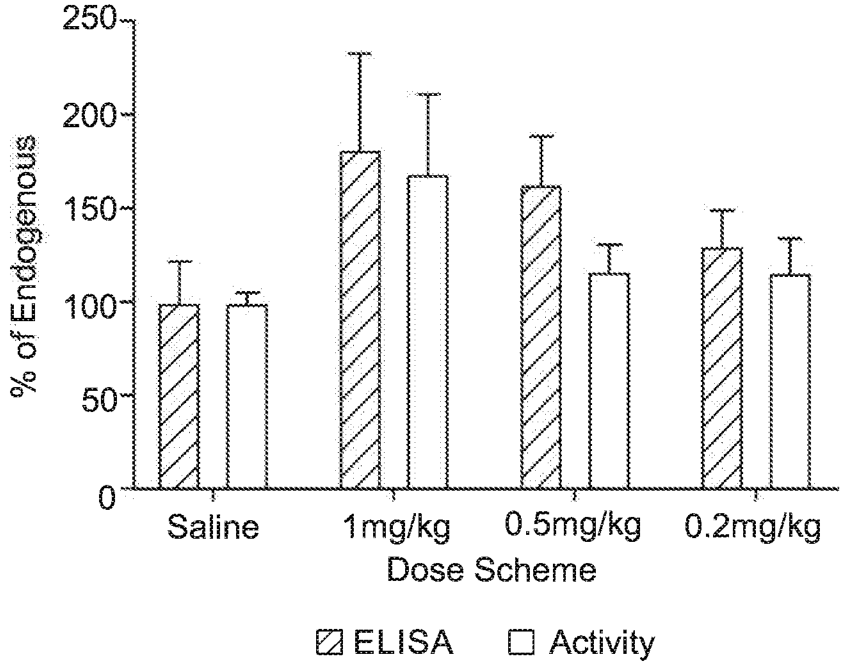
FIG. 2A shows MUT protein expression and activity detected in mouse livers 24 hours after administration of a 0.2 mg/kg, 0.5 mg/kg or 1.0 mg/kg dose of an MRT-1 formulation.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Alkyl: As used herein, "alkyl" refers to a radical of a straight-chain or branched saturated hydrocarbon group having from 1 to 15 carbon atoms ("C1-15 alkyl"). In some embodiments, an alkyl group has 1 to 3 carbon atoms ("C1-3 alkyl"). Examples of C1-3 alkyl groups include methyl (C1), ethyl (C2), n-propyl (C3), and isopropyl (C3). In some embodiments, an alkyl group has 8 to 12 carbon atoms ("C8-12 alkyl"). Examples of C8-12 alkyl groups include, without limitation, n-octyl (C8), n-nonyl (C9), n-decyl (C10), n-undecyl (C11), n-dodecyl (C12) and the like. The prefix "n-" (normal) refers to unbranched alkyl groups. For example, n-C8 alkyl refers to (CH2)7CH3, n-C10 alkyl refers to (CH2)9CH3, etc.

Amino acid: As used herein, term "amino acid," in its broadest sense, refers to any compound and/or substance that can be incorporated into a polypeptide chain. In some embodiments, an amino acid has the general structure $H_2N—C(H)(R)—COOH$. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Typically, the term "approximately" or "about" refers to a range of values that within 10%, or more typically 1%, of the stated reference value.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active.

Codon-optimized: As used herein, the term describes a nucleic acid in which one or more of the nucleotides present in a naturally occurring nucleic acid sequence (also referred to as 'wild-type' sequence) has been substituted with an alternative nucleotide to optimize protein expression without changing the amino acid sequence of the polypeptide encoded by the naturally occurring nucleic acid sequence. For example, the codon AAA may be altered to become AAG without changing the identity of the encoded amino acid (lysine). In some embodiments, the nucleic acids of the invention are codon optimized to increase protein expression of the protein encoded by the nucleic acid.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

Dosing interval: As used herein dosing interval in the context of a method for treating a disease is the frequency of administering a therapeutic composition in a subject (mammal) in need thereof, for example an mRNA composition, at an effective dose of the mRNA, such that one or more symptoms associated with the disease is reduced; or one or more biomarkers associated with the disease is reduced, at least for the period of the dosing interval. Dosing frequency and dosing interval may be used interchangeably in the current disclosure.

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Effective dose: As used herein, an effective dose is a dose of the mRNA in the pharmaceutical composition which when administered to the subject in need thereof, hereby a mammalian subject, according to the methods of the invention, is effective to bring about an expected outcome in the subject, for example reduce a symptom associated with the disease.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

messenger RNA (mRNA): As used herein, the term "messenger RNA (mRNA)" refers to a polyribonucleotide that encodes at least one polypeptide. mRNA may contain one or more coding and non-coding regions. mRNA can be purified from natural sources, produced using recombinant expression systems and optionally purified, in vitro transcribed, chemically synthesized, etc. An mRNA sequence is presented in the 5' to 3' direction unless otherwise indicated. Typically, the mRNA of the present invention is synthesized from adenosine, guanosine, cytidine and uridine nucleotides that bear no modifications. Such mRNA is referred to herein as mRNA with unmodified nucleotides or 'unmodified mRNA' for short. Typically, this means that the mRNA of the present invention does not comprise any of the following nucleoside analogs: 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine. An mRNA suitable for practising the claimed invention commonly does not comprise nucleosides comprising chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in J. Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4 alkyl)4 salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, methods and compositions for treating methylmalonic academia (MMA) based on mRNA therapy. Messenger RNA therapy is a safe and effective mode of introducing a genetic material which can stably produce the encoded protein in vivo for a period of time.

In some embodiments, a method of treatment of the invention encompasses administering to a subject in need of treatment a composition comprising an unmodified mRNA comprising a methymalonyl-CoA mutase (MUT) coding sequence at an effective dose and an administration interval such that at least one symptom or feature of MMA is reduced in intensity, severity, or frequency or has a delayed onset. Typically, the encoded mRNA comprises a codon-optimized MUT coding sequence. The mRNA is commonly provided in a delivery vehicle, typically a lipid formulation, for improved delivery of the mRNA and sustained in vivo function. Sustained in vivo expression of the MUT coding sequence may be achieved by providing the mRNA with a longer than normal 3' poly(A) tail. Typically, a modified 5' cap structure is also included in the mRNA.

MMA is marked by increased accumulation of methylmalonic acid in the tissues and serum of the patient. The present invention therefore provides methods of treating MUT deficiency comprising administering to a subject in need of treatment a therapeutically effective amount of a composition comprising an mRNA encoding MUT such that plasma methylmalonic acid levels are reduced.

Suitable lipid formulations include those in which the mRNA is encapsulated within one or more liposomes. As used herein, the term "liposome" refers to any lamellar or multilamellar nanoparticle vesicle. Typically, a liposome as used herein can be formed by mixing one or more lipids or by mixing one or more lipids and polymer(s). In some embodiments, a liposome suitable for the present invention contains cationic, non-cationic lipid(s), cholesterol-based lipid(s) and PEG-modified lipid(s).

Methylmalonic Acidemia (MMA)

Methylmalonic acidemia (MMA, also called methylmalonic aciduria) is an autosomal recessive metabolic disorder characterized by an inability to convert methylmalonyl-CoA into succinyl-CoA. The most common cause of MMA is a mutation in the MUT gene that encodes the mitochondrial methylmalonyl-CoA mutase protein. Over 100 different mutations in the MUT gene have been identified in patients with MMA.

Mutations in the MUT gene eliminate or reduce the ability of the MUT enzyme to catalyze the conversion of methylmalonyl-CoA into succinyl-CoA. As a result, toxic methylmalonic acid accumulates in the blood and body tissues, resulting in the symptoms associated with MMA. Untreated MMA can lead to brain damage, coma and death. Long term survivors suffer from chronic renal failure and neurological complications. Mutations that abolish methylmalonyl-CoA mutase activity completely have a greater occurrence of mortality, morbidity and long-term complications, while mutations leading to decreased methylmalonyl-CoA mutase activity result in a milder phenotype.

Methylmalonyl-CoA Mutase (MUT) Gene and Protein Sequence

In some embodiments, the present invention provides methods and compositions for delivering mRNA encoding MUT to a subject for the treatment of MMA. A suitable MUT mRNA encodes any full length, fragment or portion of an MUT protein which can be substituted for naturally-occurring MUT protein activity and/or reduce the intensity, severity, and/or frequency of one or more symptoms associated with MMA.

In some embodiments, a suitable mRNA sequence is an mRNA sequence encoding a human MUT protein. The naturally-occurring human MUT mRNA coding sequence and the corresponding amino acid sequence are shown in Table 1:

TABLE 1

| Human MUT | |
|---|---|
| Human | (SEQ ID NO: 1) |
| MUT | **AUG**UUAAGAGCUAAGAAUCAGCUUUUUUUACUUUCACCUCAUUACCU |
| (mRNA | GAGGCAGGUAAAAGAAUCAUCAGGCUCCAGGCUCAUACAGCAACGAC |

TABLE 1-continued

| Human MUT | |
|---|---|
| coding<br>sequence) | UUCUACACCAGCAACAGCCCCUUCACCCAGAAUGGGCUGCCCUGGCUA<br>AAAAGCAGCUGAAAGGCAAAAACCCAGAAGACCUAAUAUGGCACACCC<br>CGGAAGGGAUCUCUAUAAAACCCUUGUAUUCCAAGAGAGAUACUAUG<br>GACUUACCUGAAGAACUUCCAGGAGUGAAGCCAUUCACACGUGGACCA<br>UAUCCUACCAUGUAUACCUUUAGGCCCUGGACCAUCCGCCAGUAUGCU<br>GGUUUUAGUACUGUGGAAGAAAGCAAUAAGUUCUAUAAGGACAACAU<br>UAAGGCUGGUCAGCAGGGAUUAUCAGUUGCCUUUGAUCUGGCGACAC<br>AUCGUGGCUAUGAUUCAGACAACCCUCGAGUUCGUGGUGAUGUUGGA<br>AUGGCUGGAGUUGCUAUUGACACUGUGGAAGAUACCAAAAUUCUUUU<br>UGAUGGAAUUCCUUUAGAAAAAAUGUCAGUUUCCAUGACUAUGAAUG<br>GAGCAGUUAUUCCAGUUCUUGCAAAUUUUAUAGUAACUGGAGAAGAA<br>CAAGGUGUACCUAAAGAGAAGCUUACUGGUACCAUCCAAAAUGAUAU<br>ACUAAAGGAAUUUAUGGUUCGAAAUACAUACAUUUUUCCUCCAGAAC<br>CAUCCAUGAAAAUUAUUGCUGACAUAUUUGAAUAUACAGCAAAGCAC<br>AUGCCAAAAUUUAAUUCAAUUUCAAUUAGUGGAUACCAUAUGCAGGA<br>AGCAGGGGCUGAUGCCAUUCUGGAGCUGGCCUAUACUUUAGCAGAUG<br>GAUUGGAGUACUCUAGAACUGGACUCCAGGCUGGCCUGACAAUUGAU<br>GAAUUUGCACCAAGGUUGUCUUUCUUCUGGGGAAUUGGAAUGAAUUU<br>CUAUAUGGAAAUAGCAAAGAUGAGAGCUGGUAGAAGACUCUGGGCUC<br>ACUUAAUAGAGAAAAUGUUUCAGCCUAAAAACUCAAAAUCUCUUCUU<br>CUAAGAGCACACUGUCAGACAUCUGGAUGGUCACUUACUGAGCAGGA<br>UCCCUACAAUAAUAUUGUCCGUACUGCAAUAGAAGCAAUGGCAGCAG<br>UAUUUGGAGGGACUCAGUCUUUGCACACAAAUUCUUUUGAUGAAGCU<br>UUGGGUUUGCCAACUGUGAAAAGUGCUCGAAUUGCCAGGAACACACA<br>AAUCAUCAUUCAAGAAGAAUCUGGGAUUCCCAAAGUGGCUGAUCCUU<br>GGGGAGGUUCUUACAUGAUGGAAUGUCUCACAAAUGAUGUUUAUGAU<br>GCUGCUUUAAAGCUCAUUAAUGAAAUUGAAGAAAUGGGUGGAAUGGC<br>CAAAGCUGUAGCUGAGGGAAUACCUAAACUUCGAAUUGAAGAAUGUG<br>CUGCCCGAAGACAAGCUAGAAUAGAUUCUGGUUCUGAAGUAAUUGUU<br>GGAGUAAAUAAGUACCAGUUGGAAAAAGAAGACGCUGUAGAAGUUCU<br>GGCAAUUGAUAAUACUUCAGUGCGAAACAGGCAGAUUGAAAAACUUA<br>AGAAGAUCAAAUCCAGCAGGGAUCAAGCUUUGGCUGAACGUUGUCUU<br>GCUGCACUAACCGAAUGUGCUGCUAGCGGAGAUGGAAAUAUCCUGGC<br>UCUUGCAGUGGAUGCAUCUCGGGCAAGAUGUACAGUGGGAGAAAUCA<br>CAGAUGCCCUGAAAAAGGUAUUUGGUGAACAUAAAGCGAAUGAUCGA<br>AUGGUGAGUGGAGCAUAUCGCCAGGAAUUUGGAGAAAGUAAAGAGAU<br>AACAUCUGCUAUCAAGAGGGUUCAUAAAUUCAUGGAACGUGAAGGUC<br>GCAGACCUCGUCUUCUUGUAGCAAAAAUGGGACAAGAUGGCCAUGAC<br>AGAGGAGCAAAAGUUAUUGCUACAGGAUUUGCUGAUCUUGGUUUUGA<br>UGUGGACAUAGGCCCUCUUUUCCAGACUCCUCGUGAAGUGGCCCAGCA<br>GGCUGUGGAUGCGGAUGUGCAUGCUGUGGGCAUAAGCACCCUCGCUG<br>CUGGUCAUAAAACCCUAGUUCCUGAACUCAUCAAAGAACUUAACUCCC<br>UUGGACGGCCAGAUAUUCUUGUCAUGUGUGGAGGGGUGAUACCACCU<br>CAGGAUUAUGAAUUUCUGUUUGAAGUUGGUGUUUCCAAUGUAUUUGG<br>UCCUGGGACUCGAAUUCCAAAGGCUGCCGUUCAGGUGCUUGAUGAUA<br>UUGAGAAGUGUUUGGAAAAGAAGCAGCAAUCUGUA**UAA** |
| Human<br>MUT<br>(DNA<br>Sequence) | (SEQ ID NO: 2)<br>**ATG**TTAAGAGCTAAGAATCAGCTTTTTTTACTTTCACCTCATTACCTGAG<br>GCAGGTAAAAGAATCATCAGGCTCCAGGCTCATACAGCAACGACTTCTA<br>CACCAGCAACAGCCCCTTCACCCAGAATGGGCTGCCCTGGCTAAAAAGC<br>AGCTGAAAGGCAAAAACCCAGAAGACCTAATATGGCACACCCCGGAAG<br>GGATCTCTATAAAACCCTTGTATTCCAAGAGAGATACTATGGACTTACCT<br>GAAGAACTTCCAGGAGTGAAGCCATTCACACGTGGACCATATCCTACCA<br>TGTATACCTTTAGGCCCTGGACCATCCGCCAGTATGCTGGTTTTAGTACT<br>GTGGAAGAAAGCAATAAGTTCTATAAGGACAACATTAAGGCTGGTCAGC<br>AGGGATTATCAGTTGCCTTTGATCTGGCGACACATCGTGGCTATGATTCA<br>GACAACCCTCGAGTTCGTGGTGATGTTGGAATGGCTGGAGTTGCTATTG<br>ACACTGTGGAAGATACCAAAATTCTTTTTGATGGAATTCCTTTAGAAAAA<br>ATGTCAGTTTCCATGACTATGAATGGAGCAGTTATTCCAGTTCTTGCAAA<br>TTTTATAGTAACTGGAGAAGAACAAGGTGTACCTAAAGAGAAGCTTACT<br>GGTACCATCCAAAATGATATACTAAAGGAATTTATGGTTCGAAATACAT<br>ACATTTTTCCTCCAGAACCATCCATGAAAATTATTGCTGACATATTTGAA<br>TATACAGCAAAGCACATGCCAAAATTTAATTCAATTTCAATTAGTGGAT<br>ACCATATGCAGGAAGCAGGGGCTGATGCCATTCTGGAGCTGGCCTATAC<br>TTTAGCAGATGGATTGGAGTACTCTAGAACTGGACTCCAGGCTGGCCTG<br>ACAATTGATGAATTTGCACCAAGGTTGTCTTTCTTCTGGGGAATTGGAAT<br>GAATTTCTATATGGAAATAGCAAAGATGAGAGCTGGTAGAAGACTCTGG<br>GCTCACTTAATAGAGAAAATGTTTCAGCCTAAAAACTCAAAATCTCTTCT<br>TCTAAGAGCACACTGTCAGACATCTGGATGGTCACTTACTGAGCAGGAT<br>CCCTACAATAATATTGTCCGTACTGCAATAGAAGCAATGGCAGCAGTAT<br>TTGGAGGGACTCAGTCTTTGCACACAAATTCTTTTGATGAAGCTTTGGGT<br>TTGCCAACTGTGAAAAGTGCTCGAATTGCCAGGAACACACAAATCATCA<br>TTCAAGAAGAATCTGGGATTCCCAAAGTGGCTGATCCTTGGGGAGGTTC<br>TTACATGATGGAATGTCTCACAAATGATGTTTATGATGCTGCTTTAAAGC<br>TCATTAATGAAATTGAAGAAATGGGTGGAATGGCCAAAGCTGTAGCTGA<br>GGGAATACCTAAACTTCGAATTGAAGAATGTGCTGCCCGAAGACAAGCT<br>AGAATAGATTCTGGTTCTGAAGTAATTGTTGGAGTAAATAAGTACCAGT |

TABLE 1-continued

| | Human MUT |
|---|---|
| | TGGAAAAAGAAGACGCTGTAGAAGTTCTGGCAATTGATAATACTTCAGT<br>GCGAAACAGGCAGATTGAAAAACTTAAGAAGATCAAATCCAGCAGGGA<br>TCAAGCTTTGGCTGAACGTTGTCTTGCTGCACTAACCGAATGTGCTGCTA<br>GCGGAGATGGAAATATCCTGGCTCTTGCAGTGGATGCATCTCGGGCAAG<br>ATGTACAGTGGGAGAAATCACAGATGCCCTGAAAAAGGTATTTGGTGAA<br>CATAAAGCGAATGATCGAATGGTGAGTGGAGCATATCGCCAGGAATTTG<br>GAGAAAGTAAAGAGATAACATCTGCTATCAAGAGGGTTCATAAATTCAT<br>GGAACGTGAAGGTCGCAGACCTCGTCTTCTTGTAGCAAAAATGGGACAA<br>GATGGCCATGACAGAGGAGCAAAAGTTATTGCTACAGGATTTGCTGATC<br>TTGGTTTTGATGTGGACATAGGCCCTCTTTTCCAGACTCCTCGTGAAGTG<br>GCCCAGCAGGCTGTGGATGCGGATGTGCATGCTGTGGGCATAAGCACCC<br>TCGCTGCTGGTCATAAAACCCTAGTTCCTGAACTCATCAAAGAACTTAAC<br>TCCCTTGGACGGCCAGATATTCTTGTCATGTGTGGAGGGGTGATACCACC<br>TCAGGATTATGAATTTCTGTTTGAAGTTGGTGTTTCCAATGTATTTGGTCC<br>TGGGACTCGAATTCCAAAGGCTGCCGTTCAGGTGCTTGATGATATTGAG<br>AAGTGTTTGGAAAAGAAGCAGCAATCTGTA**TAA** |
| Human MUT Protein Sequence | (SEQ ID NO: 3)<br>MLRAKNQLFLLSPHYLRQVKESSGSRLIQQRLLHQQQPLHPEWAALAKKQL<br>KGKNPEDLIWHTPEGISIKPLYSKRDTMDLPEELPGVKPFTRGPYPTMYTFRP<br>WTIRQYAGFSTVEESNKFYKDNIKAGQQGLSVAFDLATHRGYDSDNPRVRG<br>DVGMAGVAIDTVEDTKILFDGIPLEKMSVSMTMNGAVIPVLANFIVTGEEQ<br>GVPKEKLTGTIQNDILKEFMVRNTYIFPPEPSMKIIADIFEYTAKHMPKFNSISI<br>SGYHMQEAGADAILELAYTLADGLEYSRTGLQAGLTIDEFAPRLSFFWGIG<br>MNFYMEIAKMRAGRRLWAHLIEKMFQPKNSKSLLLRAHCQTSGWSLTE<br>QDPYNNIVRTAIEAMAAVFGGTQSLHTNSFDEALGLPTVKSARIARNTQIIIQ<br>EESGIPKVADPWGGSYMMECLTNDVYDAALKLINEIEEMGGMAKAVAEGI<br>PKLRIEECAARRQARIDSGSEVIVGVNKYQLEKEDAVEVLAIDNTSVRNRQI<br>EKLKKIKSSRDQALAERCLAALTECAASGDGNILALAVDASRARCTVGEITD<br>ALKKVFGEHKANDRMVSGAYRQEFGESKEITSAIKRVHKFMEREGRRPRLL<br>VAKMGQDGHDRGAKVIATGFADLGFDVDIGPLFQTPREVAQQAVDADVH<br>AVGISTLAAGHKTLVPELIKELNSLGRPDILVMCGGVIPPQDYEFLFEVGVSN<br>VFGPGTRIPKAAVQVLDDIEKCLEKKQQSV |

In some embodiments, a suitable mRNA is a wild-type human MUT mRNA of sequence (SEQ ID NO: 1). In some embodiments, a suitable therapeutic candidate mRNA may be a codon-optimized hMUT sequence that can encode an MUT amino acid sequence shown in Table 1 as SEQ ID NO: 3 or an amino acid sequence at least 70%, 75%, 80%, 85%, 90%, 95%, 96%, 97%, 98%, or 99% identical to SEQ ID NO: 3. Typically, an mRNA according to the present invention encodes a MUT protein with an amino acid sequence that is identical to SEQ ID NO: 3.

Codon Optimization

According to an increasing amount of research, mRNAs contain numerous layers of information that overlap the amino acid code. Traditionally, codon optimization has been used to remove rare codons which were thought to be rate-limiting for protein expression. While fast growing bacteria and yeast both exhibit strong codon bias in highly expressed genes, higher eukaryotes exhibit much less codon bias, making it more difficult to discern codons that may be rate-limiting. In addition, it has been found that codon bias per se does not necessarily yield high expression but requires other features.

For example, rare codons have been implicated in slowing translation and forming pause sites, which may be required for correct protein folding. Therefore, variations in codon usage may provide a mechanism to fine-tune the temporal pattern of elongation and thus increase the time available for a protein to take on its correct confirmation. Codon optimization can interfere with this fine-tuning mechanism, resulting in less efficient protein translation or an increased amount of incorrectly folded proteins. Similarly, codon optimization may disrupt the normal patterns of cognate and wobble tRNA usage, thereby affecting protein structure and function because wobble-dependent slowing of elongation may likewise have been selected as a mechanism for achieving correct protein folding.

Despite these obstacles, the inventors have arrived at a codon-optimized hMUT sequence that improves expression of the MUT protein at least threefold over the coding sequence of the wild type gene. The increase in expression is not limited to cell cultures of mammalian cells but was also observed in vivo in a mouse model. It is expected that the observed improvement in expression of the codon-optimised MUT coding sequence will result in an improved, more cost-effective mRNA replacement therapy for patients suffering from MMA, because it does not require the use of modified nucleotides for the preparation of the mRNA and allows treatment with a reduced dose and/or at extended dosing intervals.

Exemplary Suitable Codon Optimized MUT mRNA Sequences

In some embodiments, a suitable mRNA may be a codon-optimized sequence, as shown in SEQ ID NO: 4:

(SEQ ID NO: 4)

AUGCUUAGGGCAAAGAAUCAACUCUUUCUGCUGAGCCCACACUAUUUGCG

CCAGGUGAAAGAGAGCUCCGGCUCAAGGCUGAUCCAGCAGCGUCUUUUGC

AUCAGCAGCAGCCACUGCACCCGGAAUGGGCCGCUCUCGCGAAGAAGCAG

CUGAAGGGAAAGAACCCGGAAGAUCUGAUCUGGCACACUCCGGAGGGAAU

CUCAAUCAAGCCACUGUACUCUAAGAGAGACACCAUGGACCUUCCCGAAG

AACUGCCCGGGGUGAAGCCCUUCACCCGGGGACCGUACCCGACCAUGUAC

ACCUUUAGACCGUGGACGAUCCGCCAGUACGCAGGCUUCUCGACGGUCGA

AGAAAGCAACAAAUUCUAUAAAGACAACAUUAAGGCCGGACAACAGGGAC

UGUCCGUCGCAUUCGACCUCGCCACCCACCGCGGAUACGAUUCGGACAAU

-continued

CCAAGGGUGAGAGGUGACGUCGGAAUGGCCGGAGUGGCUAUUGAUACCGU

GGAGGACACGAAGAUCCUGUUCGACGGCAUCCCCUUGGAGAAGAUGUCCG

UGAGCAUGACUAUGAAUGGCGCUGUGAUUCCUGUGCUCGCCAACUUCAUC

GUGACCGGAGAGGAACAAGGCGUGCCGAAGGAAAAGCUCACUGGCACUAU

CCAAAACGACAUCCUCAAAGAAUUCAUGGUCCGCAACACUUACAUUUUUC

CUCCCGAACCUUCGAUGAAGAUCAUCGCCGAUAUCUUUGAGUACACGGCA

AAACACAUGCCGAAGUUCAAUUCGAUCUCGAUCUCCGGAUACCAUAUGCA

AGAGGCUGGGGCCGACGCGAUCCUCGAACUGGCUUACACCCUGGCCGACG

GACUGGAAUACUCACGCACUGGGCUGCAGGCCGGUCUGACCAUCGACGAG

UUCGCGCCGAGACUGUCCUUCUUCUGGGGCAUUGGUAUGAACUUCUACAU

GGAGAUCGCCAAAAUGCGAGCAGGCCGCAGGCUCUGGGCACACCUCAUCG

AGAAAAUGUUCCAGCCGAAGAAUUCUAAGUCGCUCCUGCUGCGCGCCCAC

UGCCAGACUAGCGGAUGGAGCUUGACUGAACAGGACCCGUACAACAAUAU

CGUGCGGACUGCCAUCGAAGCGAUGGCCGCAGUGUUCGGAGGAACCCAGU

CACUGCAUACCAACAGCUUUGACGAAGCCCUCGGCUUGCCAACUGUGAAA

AGCGCGCGGAUCGCAAGGAACACUCAGAUCAUUAUCCAAGAAGAAUCCGG

UAUCCCUAAGGUGGCCGAUCCGUGGGGCGGAUCCUACAUGAUGGAGUGCC

UGACCAAUGACGUCUACGAUGCCGCGCUGAAACUGAUCAACGAGAUUGAA

GAGAUGGGAGGAAUGGCUAAGGCCGUUGCAGAAGGGAUCCCGAAGCUGCG

GAUUGAGGAAUGUGCGGCCCGGCGCCAGGCCCGAAUCGAUAGCGGCUCAG

AAGUUAUCGUGGGUGUCAACAAGUACCAGCUUGAGAAGGAAGAUGCAGUG

GAGGUCCUCGCAAUUGAUAAUACCUCCGUCCGGAAUAGACAAAUCGAAAA

ACUGAAAAAGAUCAAGAGCUCCCGCGACCAAGCCCUGGCGGAAAGAUGCU

UGGCGGCCCUGACCGAGUGCGCUGCCUCAGGCGACGGAAACAUCCUGGCA

CUCGCAGUCGAUGCCUCGCGGGCGCGCUGCACUGUGGGUGAGAUCACCGA

CGCCCUCAAGAAGGUCUUUGGAGAGCAUAAGGCGAACGACAGAAUGGUGU

CGGGAGCAUACCGGCAGGAGUUCGGCGAAUCCAAAGAGAUCACUUCGGCG

AUCAAACGCGUGCACAAGUUCAUGGAACGGGAGGGGCGGCGGCCGCGCCU

UCUCGUGGCGAAGAUGGGGCAGGAUGGACAUGACCGCGGAGCUAAGGUGA

UCGCCACCGGGUUCGCUGAUCUCGGGUUCGACGUGGACAUCGGCCCUCUG

UUCCAAACCCCUAGAGAAGUGGCGCAACAAGCUGUGGAUGCUGAUGUGCA

UGCGGUCGGAAUCUCCACCCUCGCAGCCGGACAUAAAACUCUGGUGCCCG

AGCUCAUAAAGGAACUGAACUCGCUGGGCCGGCCAGAUAUCCUGGUCAUG

UGCGGUGGAGUGAUCCCACCUCAAGAUUACGAGUUCCUGUUUGAAGUCGG

AGUGUCAAACGUGUUUGGACCGGGAACUCGCAUCCCAAAGGCGGCCGUGC

AAGUCCUUGAUGACAUUGAAAAGUGUCUGGAGAAAAAGCAGCAGAGCGUG

UAG

In some embodiments, a suitable mRNA may be a codon-optimized sequence, as shown in SEQ ID NO: 5:

(SEQ ID NO: 5)

AUGCUGCGGGCCAAGAACCAGCUGUUCCUCCUUUCCCCCCACUACCUGAG

ACAAGUCAAAGAAUCCUCCGGAUCAAGAUUGAUUCAGCAACGCCUGUUGC

AUCAGCAACAGCCAUUGCACCCUGAAUGGGCCGCCCUGGCUAAGAAGCAG

CUUAAGGGAAAGAACCCGGAAGAUCUGAUCUGGCACACCCCGGAAGGCAU

CUCUAUCAAGCCUCUGUACUCCAAGAGAGACACCAUGGAUCUCCCUGAGG

AACUGCCGGGAGUCAAGCCUUUUACCCGCGGUCCGUACCCUACCAUGUAC

ACGUUCCGCCCGUGGACCAUCAGGCAGUACGCCGGAUUCAGCACGGUGGA

AGAGAGCAACAAGUUCUACAAGGACAACAUAAAGGCCGGACAGCAGGGAC

UGUCCGUGGCCUUCGACCUGGCCACCCAUCGGGGCUAUGACUCGGACAAC

CCUCGCGUGCGCGGGGAUGUCGGAAUGGCCGGAGUGGCGAUUGACACUGU

CGAGGACACUAAGAUCCUGUUCGAUGGCAUUCCCCUGGAAAAGAUGUCCG

UGAGCAUGACUAUGAACGGCGCAGUGAUCCCAGUGCUGGCUAACUUCAUC

GUGACUGGAGAGGAGCAAGGGGUGCCCAAAGAGAAGCUGACUGGAACUAU

CCAGAACGAUAUUCUGAAGGAGUUUAUGGUCCGGAACACUUACAUUUUCC

CGCCCGAGCCCUCGAUGAAGAUCAUCGCGGACAUUUUCGAGUACACCGCC

AAGCAUAUGCCUAAGUUCAACUCCAUCUCGAUCUCCGGAUACCACAUGCA

GGAAGCCGGAGCGGACGCGAUCCUUGAACUGGCGUACACUCUGGCCGAUG

GCCUGGAAUACUCCCGCACGGGCUUGCAGGCCGGUCUGACCAUCGACGAA

UUUGCCCCGCGGUUGUCCUUCUUUUGGGGAAUCGGCAUGAAUUUCUACAU

GGAAAUCGCCAAGAUGAGAGCGGGCCGGAGACUGUGGGCCCACCUGAUCG

AGAAGAUGUUCCAGCCCAAGAACUCGAAAAGCCUCCUCCUGCGGGCGCAC

UGCCAGACCUCCGGAUGGUCCCUGACCGAGCAGGACCCGUACAACAACAU

CGUCCGAACCGCUAUUGAGGCCAUGGCCGCCGUGUUUGGGGGAACUCAGU

CACUCCAUACUAAUUCCUUCGAUGAAGCCCUGGGGCUUCCUACCGUCAAG

AGCGCCCGGAUCGCCAGGAAUACCCAGAUCAUCAUUCAAGAAGAGUCAGG

CAUCCCUAAAGUGGCCGACCCCUGGGGGGAAGCUACAUGAUGGAAUGUU

UGACCAACGACGUCUACGACGCCGCCCUGAAGCUCAUCAACGAAAUUGAA

GAAAUGGGCGGCAUGGCCAAGGCCGUGGCAGAGGGGAUCCCUAAGCUGCG

GAUUGAGGAAUGCGCCGCCAGACGCCAGGCCCGAAUCGACUCCGGUUCCG

AAGUCAUCGUGGGCGUGAACAAGUACCAGCUGGAGAAGGAAGAUGCCGUG

GAAGUGCUGGCCAUUGAUAACACCUCCGUGCGCAACCGCCAGAUCGAAAA

GCUGAAAAAGAUUAAGUCGUCGCGCGACCAGGCACUGGCGGAGAGAUGCC

UGGCUGCACUGACCGAGUGCGCGGCGUCUGGGGACGGCAAUAUCCUGGCA

CUGGCUGUGGACGCGAGCCGGGCCCGCUGCACUGUGGGAGAGAUCACUGA

UGCCCUCAAGAAAGUGUUCGGAGAACACAAGGCCAACGACAGAAUGGUGU

CGGGGGCCUAUCGCCAAGAAUUCGGGGAGUCGAAGGAAAUCACCAGCGCC

AUUAAGCGGGUGCACAAGUUCAUGGAAAGGGAAGGACGCCGGCCACGCCU

CCUGGUGGCAAAGAUGGGACAGGACGGUCACGACAGGGGCGCAAAGGUCA

-continued

UCGCGACCGGAUUCGCCGACCUCGGCUUCGAUGUGGACAUUGGACCCCUU

UUCCAAACCCCUCGGGAGGUCGCCCAACAAGCUGUGGAUGCCGACGUGCA

UGCUGUGGGAAUUUCGACCCUGGCCGCCGGUCACAAGACCCUGGUGCCCG

AACUGAUUAAGGAGCUGAACUCACUGGGAAGGCCUGAUAUUCUCGUGAUG

UGUGGCGGAGUGAUCCCGCCGCAAGACUACGAAUUCCUGUUCGAAGUCGG

CGUGUCCAACGUGUUCGGGCCCGGCACACGGAUCCCGAAAGCCGCGGUCC

AAGUGCUCGAUGAUAUUGAGAAGUGUCUCGAAAAGAAACAGCAGUCCGUC

UAG

In some embodiments a suitable mRNA may be a codon-optimized sequence, as shown in SEQ ID NO: 12:

(SEQ ID NO: 12)

AUGCUGCGGGCCAAGAACCAGCUGUUCCUGCUGAGCCCUCACUACCUGCG

GCAGGUGAAGGAGAGCAGCGGCAGCCGGCUGAUCCAGCAGCGGCUGCUGC

ACCAGCAGCAGCCCCUGCACCCCGAGUGGGCCGCCCUGGCCAAGAAGCAG

CUGAAGGGCAAGAACCCCGAGGACCUGAUCUGGCACACGCCCGAGGGCAU

CAGCAUCAAGCCCCUGUACAGCAAGCGGGACACCAUGGACCUGCCCGAGG

AGCUGCCCGGCGUGAAGCCCUUCACCCGGGGCCCCUACCCCACCAUGUAC

ACCUUCCGGCCCUGGACCAUCCGGCAGUACGCCGGCUUCAGCACCGUGGA

GGAGAGCAACAAGUUCUACAAGGACAACAUCAAGGCCGGCCAGCAGGGCC

UGAGCGUGGCCUUCGACCUGGCCACCCACCGGGGCUACGACAGCGACAAC

CCACGGGUGCGGGGCGACGUGGGCAUGGCCGGCGUGGCCAUCGACACCGU

GGAGGACACCAAGAUCCUGUUCGACGGCAUCCCUCUGGAGAAGAUGAGCG

UGAGCAUGACCAUGAACGGCGCCGUGAUCCCCGUGCUGGCCAACUUCAUC

GUGACCGGCGAGGAGCAGGGCGUGCCCAAGGAGAAGCUGACCGGCACCAU

CCAGAACGACAUCCUGAAGGAGUUCAUGGUGCGGAACACCUACAUCUUCC

CUCCCGAGCCCAGCAUGAAGAUCAUCGCCGACAUCUUCGAGUACACCGCC

AAGCACAUGCCCAAGUUCAACAGCAUCAGCAUCAGCGGCUACCACAUGCA

GGAGGCCGGCGCCGACGCCAUCCUGGAGCUGGCCUACACCCUGGCCGACG

GCCUGGAGUACAGCCGGACCGGCCUGCAGGCCGGCCUGACCAUCGACGAG

UUCGCGCCCCGGCUGAGCUUCUUCUGGGGCAUCGGCAUGAACUUCUACAU

GGAGAUCGCCAAGAUGCGGGCCGGCCGGCGGCUGUGGGCCCACCUGAUCG

AGAAGAUGUUCCAGCCCAAGAACAGCAAGAGCCUGCUGCUGCGGGCCCAC

UGCCAGACCAGCGGCUGGAGCCUGACCGAGCAGGACCCCUACAACAACAU

CGUGCGGACCGCCAUCGAGGCCAUGGCCGCCGUGUUCGGCGGCACCCAGA

GCCUGCACACCAACAGCUUCGACGAGGCCCUGGGCCUGCCCACCGUGAAG

AGCGCCCGGAUCGCCCGGAACACCCAGAUCAUCAUCCAGGAGGAGAGCGG

CAUCCCCAAGGUGGCCGACCCCUGGGGCGGCAGCUACAUGAUGGAGUGCC

UGACCAACGACGUGUACGACGCCGCCCUGAAGCUGAUCAACGAGAUCGAG

GAGAUGGGCGGCAUGGCCAAGGCCGUGGCCGAGGGCAUCCCCAAGCUGCG

GAUCGAGGAGUGCGCCGCCCGGCGGCAGGCCCGGAUCGACAGCGGCAGCG

AGGUGAUCGUGGGCGUGAACAAGUACCAGCUGGAGAAGGAGGACGCCGUG

-continued

GAGGUGCUGGCCAUCGACAACACCAGCGUGCGGAACCGGCAGAUCGAGAA

GCUGAAGAAGAUCAAGAGCAGCCGGGACCAGGCCCUGGCCGAGCGGUGCC

UGGCCGCCCUGACCGAGUGCGCCGCCAGCGGCGACGGCAACAUCCUGGCC

CUGGCCGUGGACGCCAGCCGGGCCCGGUGCACCGUGGGCGAGAUCACCGA

CGCCCUGAAGAAGGUGUUCGGCGAGCACAAGGCCAACGACCGGAUGGUGA

GCGGCGCCUACCGGCAGGAGUUCGGCGAGAGCAAGGAGAUCACCAGCGCC

AUCAAGCGGGUGCACAAGUUCAUGGAGCGGGAGGGCCGGCGGCCCCGGCU

GCUGGUGGCCAAGAUGGGCCAGGACGGCCACGACCGGGGCGCCAAGGUGA

UCGCCACCGGCUUCGCCGACCUGGGCUUCGACGUGGACAUCGGCCCACUG

UUCCAGACGCCCCGGGAGGUGGCCCAGCAGGCCGUGGACGCCGACGUGCA

CGCCGUGGGCGUGAGCACCCUGGCCGCCGGCCACAAGACCCUGGUGCCCG

AGCUGAUCAAGGAGCUGAACAGCCUGGGCCGGCCCGACAUCCUGGUGAUG

UGCGGCGGCGUGAUCCCGCCCCAGGACUACGAGUUCCUGUUCGAGGUGGG

CGUGAGCAACGUGUUCGGCCCCGGCACCCGGAUCCCCAAGGCCGCCGUGC

AGGUGCUGGACGACAUCGAGAAGUGCCUGGAGAAGAAGCAGCAGAGCGUG

UGA

In some embodiments, a suitable mRNA sequence may be an mRNA sequence a homolog or an analog of human MUT protein. For example, a homolog or an analog of human MUT protein may be a modified human MUT protein containing one or more amino acid substitutions, deletions, and/or insertions as compared to a wild-type or naturally-occurring human MUT protein while retaining substantial MUT protein activity. In some embodiments, an mRNA suitable for the present invention encodes an amino acid sequence at least 70%, 75%, 80%, 85%, 90%, 91%, 92%, 93%, 94%, 95%, 96%, 97%, 98%, 99% or more homologous to SEQ ID NO: 3. In some embodiments, an mRNA suitable for the present invention encodes a protein substantially identical to human MUT protein. In some embodiments, an mRNA suitable for the present invention encodes an amino acid sequence at least 70%, 75%, 80%, 85%, 90%, 91%, 92%, 93%, 94%, 95%, 96%, 97%, 98%, 99% or more identical to SEQ ID NO: 3. Typically, an mRNA according to the present invention encodes a MUT protein with an amino acid sequence that is identical to SEQ ID NO: 3.

In some embodiments, an mRNA suitable for the present invention encodes a fragment or a portion of human MUT protein. In some embodiments, an mRNA suitable for the present invention encodes a fragment or a portion of human MUT protein, wherein the fragment or portion of the protein still maintains MUT activity similar to that of the wild-type protein.

In some embodiments, a suitable mRNA encodes a fusion protein comprising a full length, fragment or portion of an MUT protein fused to another protein (e.g., an N or C terminal fusion). In some embodiments, the protein fused to the mRNA encoding a full length, fragment or portion of an MUT protein encodes a signal or a cellular targeting sequence.

In some embodiments, an mRNA suitable for the present invention comprises a nucleotide sequence at least 85%, 90%, 91%, 92%, 93%, 94%, 95%, 96%, 97%, 98%, 99% or more identical to SEQ ID NO: 1, SEQ ID NO: 4 or SEQ ID NO: 5. More typically, an mRNA in accordance with the present invention comprises a nucleotide sequence at least 95% identical to SEQ ID NO: 4. Preferably, an mRNA according to the present invention comprises a nucleotide sequence at least 99% identical to SEQ ID NO: 4. For example, an mRNA according to the present invention comprises the nucleotide sequence of SEQ ID NO: 4.

Messenger RNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Typically, the mRNA according to the present invention is synthesized as unmodified mRNA. Accordingly, the mRNAs of the invention are synthesized from naturally occurring nucleotides including purines (adenine (A), guanine (G)) or pyrimidines (cytosine (C), uracil (U)).

Typically, mRNA synthesis includes the addition of a “cap” on the N-terminal (5') end, and a “tail” on the C-terminal (3') end. The presence of the cap is important in providing resistance to nucleases found in most eukaryotic cells. The presence of a “tail” serves to protect the mRNA from exonuclease degradation.

Thus, in some embodiments, mRNAs (e.g., MUT-encoding mRNAs) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

In some embodiments, mRNAs (e.g., MUT-encoding mRNAs) include a 3' poly(A) tail structure. A poly-A tail on the 3' terminus of mRNA typically includes about 10 to 800 adenosine nucleotides (e.g., about 300 to 500 adenosine nucleotides, about 300 to 800 adenosine nucleotides (SEQ ID NO: 9), about 10 to 500 adenosine nucleotides, about 10 to 300 adenosine nucleotides, about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). Typically, a poly-A tail in an mRNA in accordance with the invention is about 300 to about 800 adenosine nucleotides long (SEQ ID NO: 9). More commonly, the poly-A tail is about 300 adenosine nucleotides long (SEQ ID NO: 10). In some embodiments, the poly(A) tail structure comprises at least 85%, 90%, 95% or 100% adenosine.

In some embodiments, mRNAs include a 3' poly(C) tail structure. A suitable poly-C tail on the 3' terminus of mRNA typically include about 10 to 200 cytosine nucleotides (SEQ ID NO: 11) (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the mRNA further comprises a 5' untranslated region (5' UTR) comprising a nucleotide sequence and positioned between the 5' cap structure and coding sequence, and/or a 3' untranslated region (3' UTR) comprising a nucleotide sequence and positioned between the coding sequence and the poly(A) tail structure. In some embodiments, a 5' untranslated region includes one or more elements that affect an mRNA’s stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA’s stability of location in a cell, or one or more binding sites for miRNAs. In some embodiments, a 3' untranslated region may be between 50 and 500 nucleotides in length or longer.

Modified mRNA mRNAs according to the present invention are typically synthesized as unmodified mRNAs. In some embodiments, it may be advantageous to synthesize an mRNA encoding a codon-optimized MUT coding sequence of the present invention with one or more modified nucleotides. Typically, mRNAs are modified to enhance their stability or reduce their immunogenic properties, in particular when administered to a subject as naked mRNAs or in complexed form. Therefore, providing an mRNA encoding a codon-optimized MUT coding sequence of the present invention may have synergistic effects, resulting in sustained in vivo function that exceeds that observed with unmodified mRNAs.

Modifications of mRNA can include, for example, modifications of the nucleotides of the RNA. A modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs of the present invention may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs of the present invention may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-T-deoxyuridine 5'-triphosphate), 2'-deoxy-T-deamine-oligoribonucleotide (2'-amino-T-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-T-deoxycytidine 5'-triphosphate, 2'-azido-2'-deoxyuridine 5'-triphosphate).

In some embodiments, mRNAs of the present invention may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-tripho sphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, O6-methylguanosine 5'-triphosphate, pseudouridine 5'-triphosphate, puromycin 5'-triphosphate or xanthosine 5'-triphosphate.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of m7G(5')ppp(5')N, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is m7G(5')ppp(5')G, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form m7G(5')ppp(5')G ("m7GpppG") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —OCH3.

Additional cap analogs include, but are not limited to, a chemical structures selected from the group consisting of m7GpppG, m7GpppA, m7GpppC; unmethylated cap analogs (e.g., GpppG); dimethylated cap analog (e.g., m2,7GpppG), trimethylated cap analog (e.g., m2,2, 7GpppG), dimethylated symmetrical cap analogs (e.g., m7Gpppm7G), or anti reverse cap analogs (e.g., ARCA; m7,2'OmeGpppG, m72'dGpppG, m7,3'OmeGpppG, m7,3'dGpppG and their tetraphosphate derivatives) (see, e.g., Jemielity, J. et al., "Novel 'anti-reverse' cap analogs with superior translational properties", RNA, 9: 1108-1122 (2003)).

In some embodiments, a suitable cap is a 7-methyl guanylate ("m7G") linked via a triphosphate bridge to the 5'-end of the first transcribed nucleotide, resulting in m7G (5')ppp(5')N, where N is any nucleoside. A preferred embodiment of a m7G cap utilized in embodiments of the invention is m7G(5')ppp(5')G.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of m7G cap analogs are known in the art, many of which are commercially available. These include the m7GpppG described above, as well as the ARCA 3'-OCH3 and 2'-OCH3 cap analogs (Jemielity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly-A tail is thought to stabilize natural messengers and synthetic sense RNA. Therefore, in certain embodiments a long poly-A tail can be added to an mRNA molecule thus rendering the RNA more stable. Poly-A tails can be added using a variety of art-recognized techniques. For example, long poly-A tails can be added to synthetic or in vitro transcribed RNA using poly A polymerase (Yokoe, et al. Nature Biotechnology. 1996; 14: 1252-1256). A transcription vector can also encode long poly-A tails. In addition, poly-A tails can be added by transcription directly from PCR products. Poly-A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' poly(A) tail structure. Typically, the length of the poly-A tail can be at least about 10, 50, 100, 200, 300 (SEQ ID NO: 10), 400 or 500 nucleotides in length. In some embodiments, a poly-A tail on the 3' terminus of mRNA typically includes about 10 to 800 adenosine nucleotides (e.g., about 300 to 500 adenosine nucleotides, about 300 to 800 adenosine nucleotides (SEQ ID NO: 9), about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). Typically, a poly-A tail in an mRNA in accordance with the invention is about 300 to about 800 adenosine nucleotides long (SEQ ID NO: 9). More commonly, the poly-A tail is about 300 adenosine nucleotides long (SEQ ID NO: 10).

In some embodiments, mRNAs include a 3' poly(C) tail structure. A suitable poly-C tail on the 3' terminus of mRNA typically include about 10 to 200 cytosine nucleotides (SEQ ID NO: 11) (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' untranslated region (UTR). In some embodiments, mRNAs include a 3' untranslated region. In some embodiments, mRNAs include both a 5' untranslated region and a 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and 5' untranslated region sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

In certain embodiments, the codon-optimized MUT mRNA includes a coding region having a codon-optimized coding region flanked by 5' and 3' untranslated regions as represented as X and Y, respectively (vide infra)

X—Coding Region—Y where the coding region sequence is SEQ ID NO: 4 or a sequence 70%, 75%, 80%, 85%, 90%, 91%, 92%, 93%, 94%, 95%, 96%, 97%, 98%, 99% or more identical to SEQ ID NO: 4; or SEQ ID NO: 5 or a sequence 70%, 75%, 80%, 85%, 90%, 91%, 92%, 93%, 94%, 95%, 96%, 97%, 98%, 99% or more identical to SEQ ID NO: 5; and where X (5' UTR Sequence) is GGACAGAUCGCCUGGA-GACGCCAUCCACGCUGUUUUGACCUCCAUAGAA-GACACC GGGACCGAUCCAGCCUCCGCGGCCGG-GAACGGUGCAUUGGAACGCGGAUUCCCCG UGCCAAGAGUGACUCACCGUCCUUGACACG (SEQ ID NO: 6) or a sequence 70%, 75%, 80%, 85%, 90%, 91%, 92%, 93%, 94%, 95%, 96%, 97%, 98%, 99% or more identical to SEQ ID NO: 6; and where Y (3' UTR Sequence) is CGGGUGGCAUCCCUGUGACCCCUCCCCAGUGC-CUCUCCUGGCCCUGGAAGUUGCC ACUCCAGUGCCCACCAGCCUUGUCC-UAAUAAAAUUAAGUUGCAUCAAGCU (SEQ ID NO: 7) or a sequence 70%, 75%, 80%, 85%, 90%, 91%, 92%, 93%, 94%, 95%, 96%, 97%, 98%, 99% or more identical to SEQ ID NO: 7, or GGGUGGCAUCCCUGUGACCC-CUCCCCAGUGCCUCUCCUGGCCCUG-GAAGUUGCCA CUCCAGUGCCCACCAGCCUUGUC-CUAAUAAAAUUAAGUUGCAUCAAAGCU (SEQ ID NO: 8) or a sequence 70%, 75%, 80%, 85%, 90%, 91%, 92%, 93%, 94%, 95%, 96%, 97%, 98%, 99% or more identical to SEQ ID NO: 8.

In Vitro Transcription

In certain embodiments of the invention, a codon-optimized human methlmalonyl-CoA mutase messenger RNA (MUT mRNA) is synthesized by in vitro transcription from a plasmid DNA template encoding the gene, which is followed by the addition of a 5' cap structure (Fechter, P.; Brownlee, G. G. "Recognition of mRNA cap structures by viral and cellular proteins" J. Gen. Virology 2005, 86, 1239-1249) and a 3' poly(A) tail of approximately 100, 200, 250, 300 (SEQ ID NO: 10), 400, 500 or 800 nucleotides in length as determined by gel electrophoresis.

Delivery Vehicles

According to the present invention, mRNA encoding an MUT protein (e.g., a full length, fragment or portion of an MUT protein) as described herein may be delivered as naked RNA (unpackaged) or via delivery vehicles. As used herein, the terms "delivery vehicle," "transfer vehicle," "nanoparticle" or grammatical equivalent, are used interchangeably.

In some embodiments, mRNAs encoding an MUT protein may be delivered via a single delivery vehicle. In some embodiments, mRNAs encoding an MUT protein may be delivered via one or more delivery vehicles each of a different composition. According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

Liposomes

In some embodiments, a suitable delivery vehicle is a liposome. As used herein, liposomes are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphophilic polymers and surfactants (e.g., polymerosomes, niosomes, etc.). In the context of the present invention, liposome typically serves to transport a desired mRNA to a target cell or tissue. A typical liposome in accordance with the invention comprises one or more cationic lipids, one or more non-cationic lipids, one or more cholesterol-based lipids and one or more PEG-modified lipids.

Cationic Lipids

As used herein, the phrase "cationic lipids" refers to any of a number of lipid species that have a net positive charge at a selected pH, such as physiological pH.

Several cationic lipids have been described in the literature, many of which are commercially available. Suitable cationic lipids for use in the compositions and methods of the invention include the cationic lipids as described in International Patent Publication WO 2010/144740, which is incorporated herein by reference.

In certain embodiments, the compositions and methods of the present invention include a cationic lipid, (6Z,9Z,28Z,31Z)-heptatriaconta-6,9,28,31-tetraen-19-yl4-(dimethylamino) butanoate, having a compound structure of:

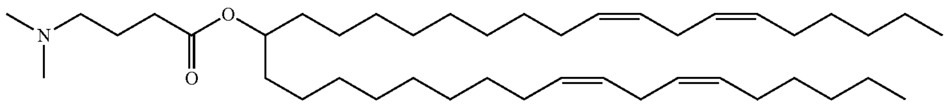 [SMILES: CCCCC/C=C\C/C=C\CCCCCCCCC(CCCCCCCC/C=C\C/C=C\CCCCC)OC(=O)CCCN(C)C]

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

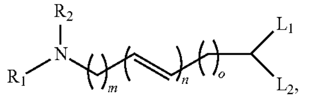

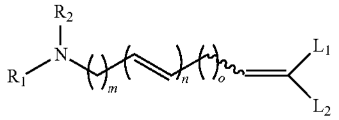

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z,18Z)—N,N-dimethyl-6-(9Z,12Z)-octadeca-9,12-dien-1-yl) tetracosa-15,18-dien-1-amine ("HGT5000"), having a compound structure of:

(HGT-5000)

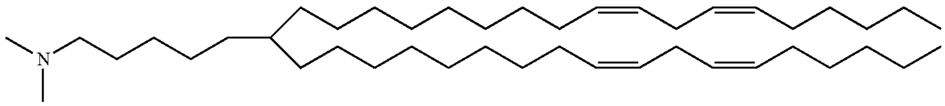

and pharmaceutically acceptable salts thereof. In certain embodiments, the compositions and methods of the present invention include the cationic lipid (15Z,18Z)-N,N-dimethyl-6-((9Z,12Z)-octadeca-9,12-dien-1-yl) tetracosa-4,15,18-trien-1-amine ("HGT5001"), having a compound structure of:

(HGT-5001)

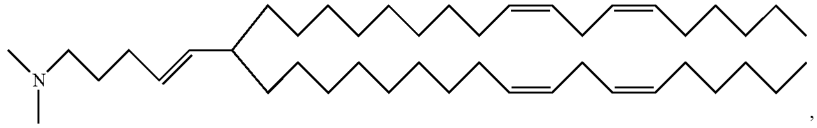

, and pharmaceutically acceptable salts thereof. In certain embodiments, the compositions and methods of the present invention include the cationic lipid and (15Z,18Z)-N,N-dimethyl-6-((9Z,12Z)-octadeca-9,12-dien-1-yl) tetracosa-5,15,18-trien-1-amine ("HGT5002"), having a compound structure of:

(HGT-5002)

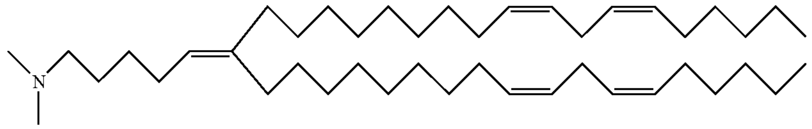

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

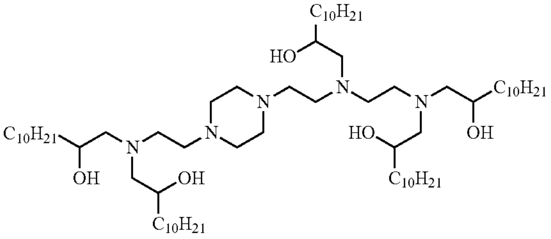

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

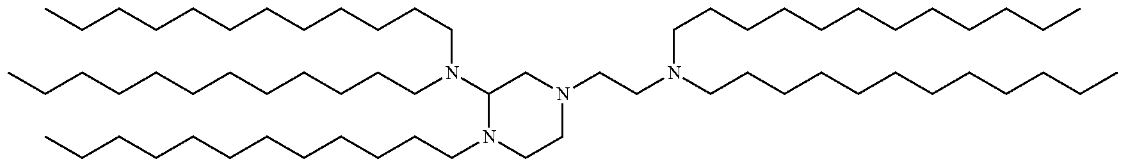 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

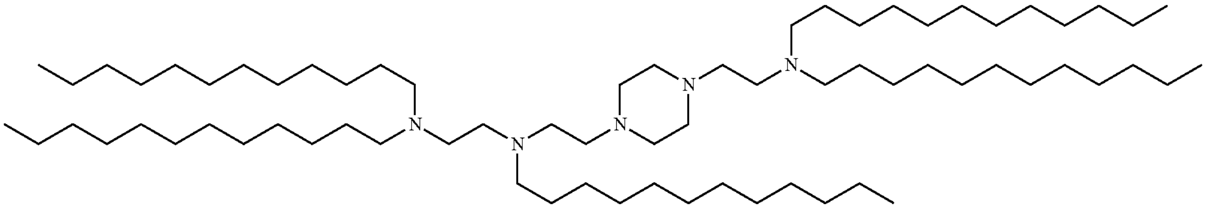 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

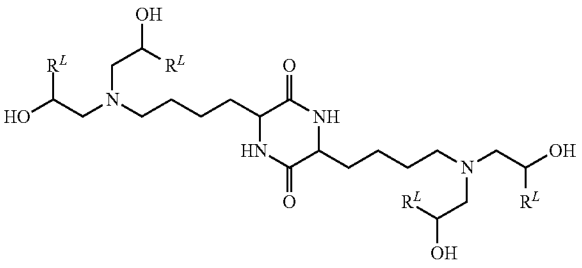

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

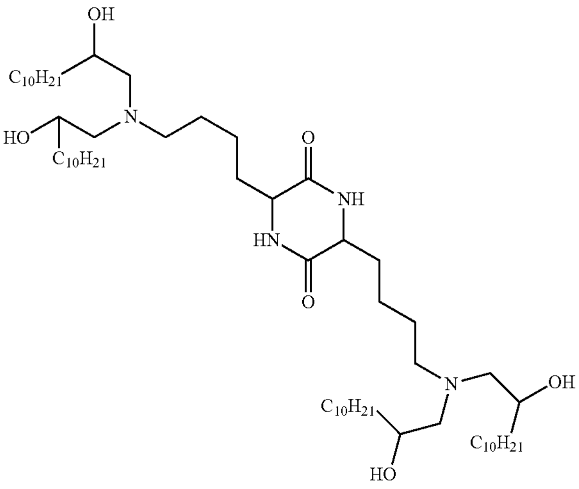

and pharmaceutically acceptable salts thereof. In certain embodiments, the compositions and methods of the present invention include a cationic lipid having a compound structure of:

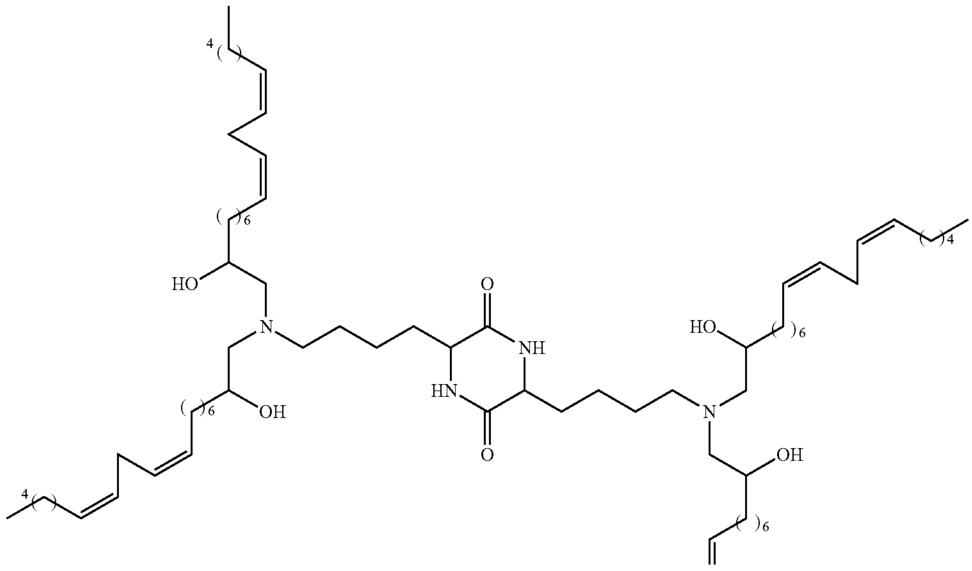

-continued

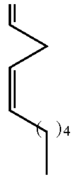

and pharmaceutically acceptable salts thereof. In certain embodiments, the compositions and methods of the present invention include a cationic lipid having a compound structure of:

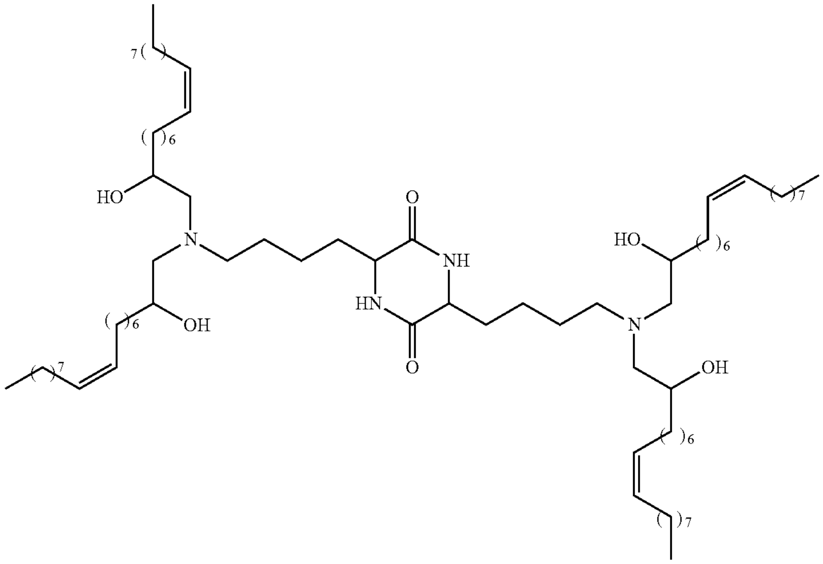

and pharmaceutically acceptable salts thereof. In certain embodiments, the compositions and methods of the present invention include a cationic lipid having a compound structure of:

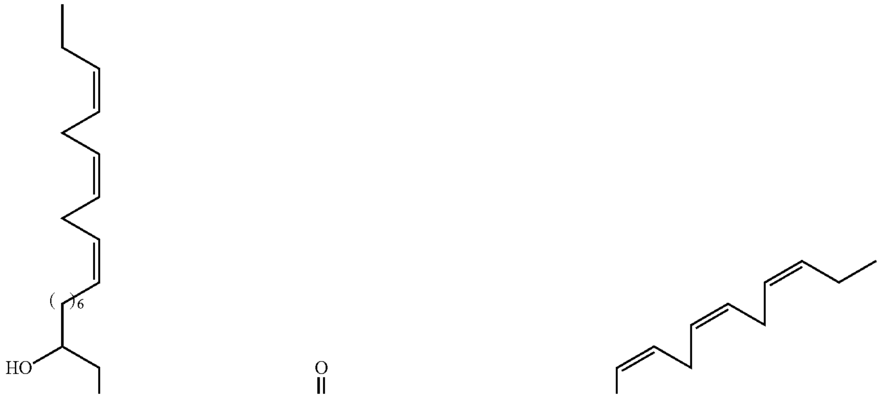

-continued

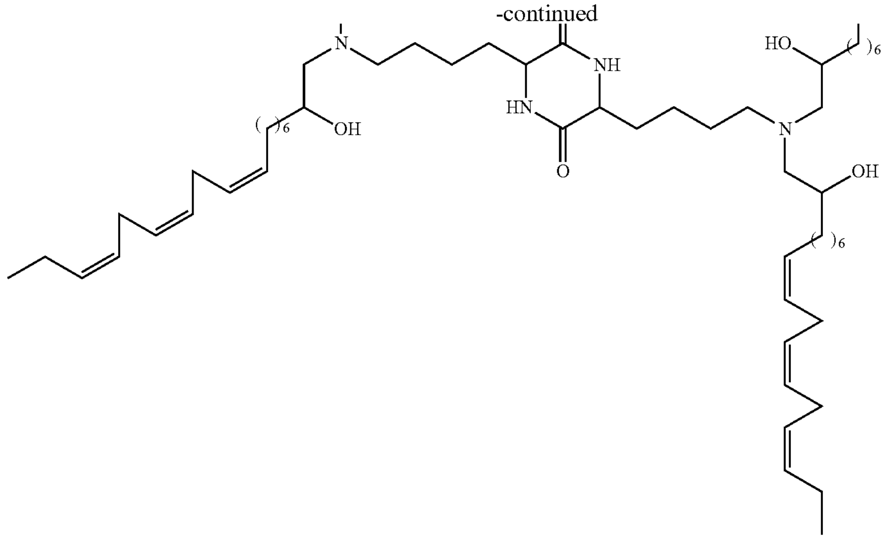

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

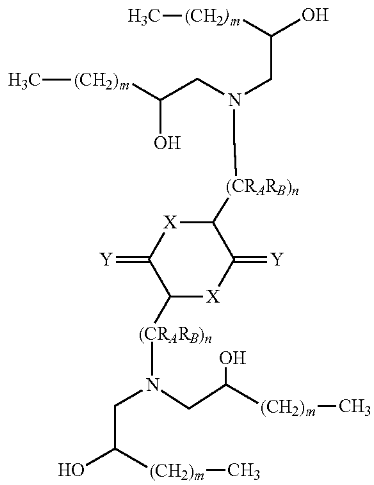

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each $R_B$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

(Target 23)

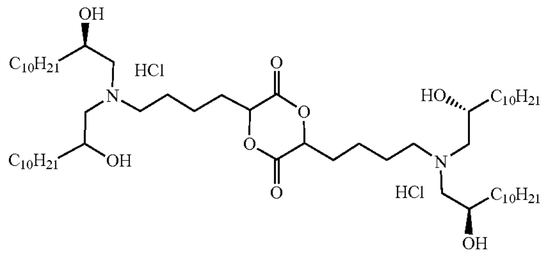

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

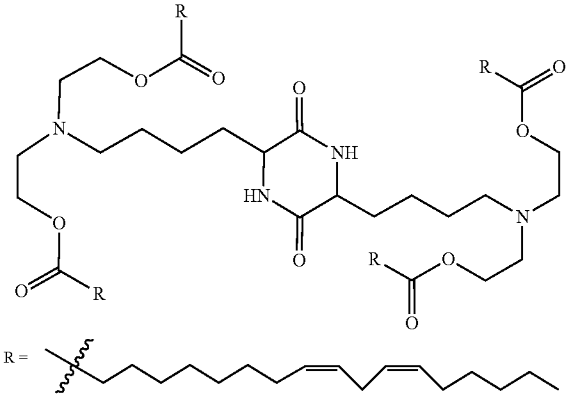

or a pharmaceutically acceptable salt thereof. In some embodiments, the compositions and methods of the present invention include a cationic lipid having the compound structure:

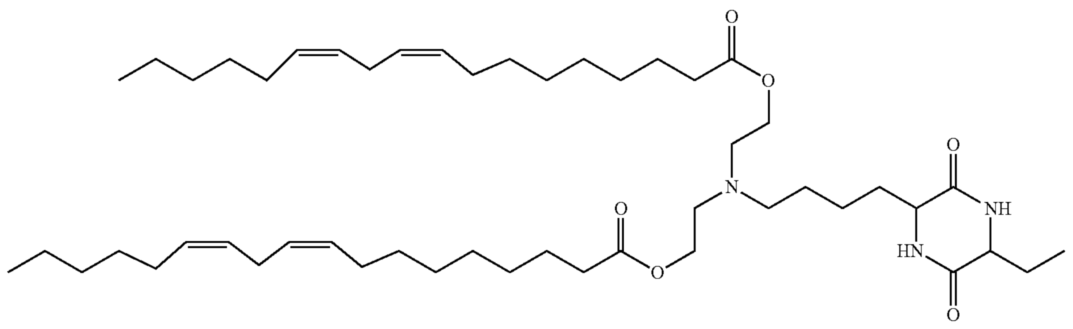 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

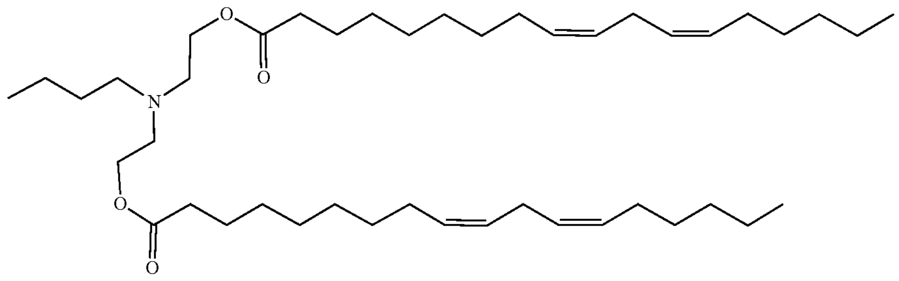 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

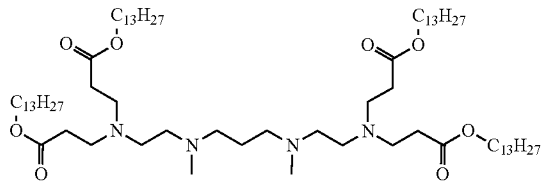

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

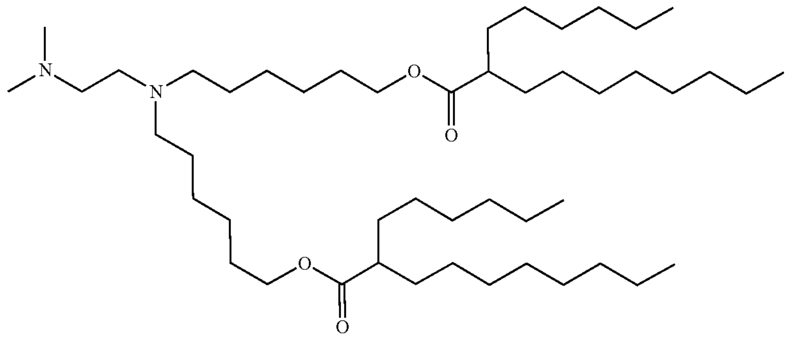 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

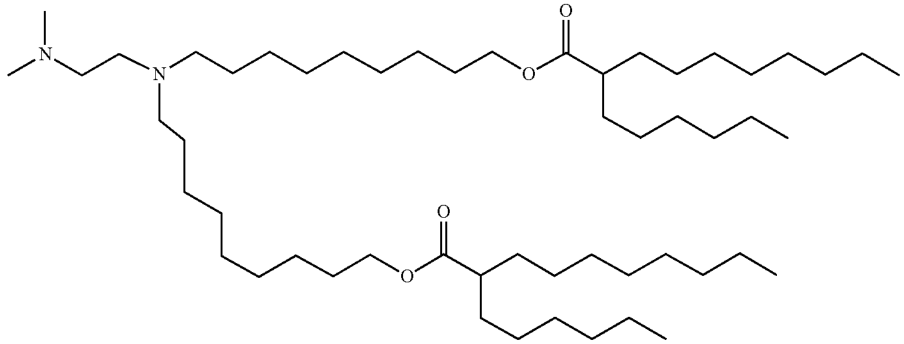 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

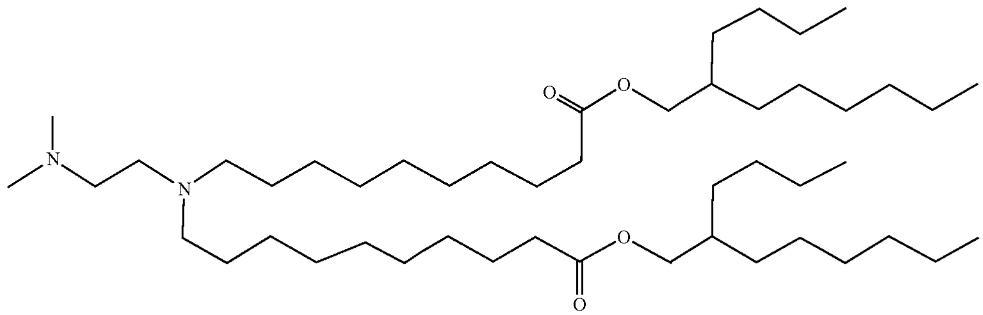 [SMILES: CCCCCCCCC(CCCC)C(C)OC(=O)CCCCCCCCCCCN(CCCCCCCCCC(=O)OCCC(CCCC)CCCCCCC)CCN(C)C]

and pharmaceutically acceptable salts thereof. In some embodiments, the compositions and methods of the present invention include a cationic lipid having the compound structure:

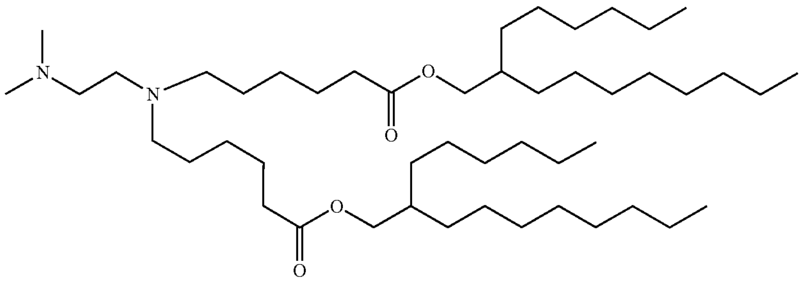 [SMILES: CCCCCCCCC(CCCCCC)COC(=O)CCCCCN(CCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

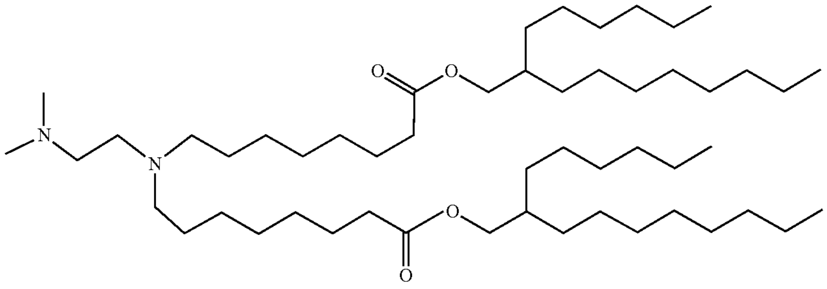

and pharmaceutically acceptable salts thereof. In some embodiments, the compositions and methods of the present invention include a cationic lipid having the compound structure:

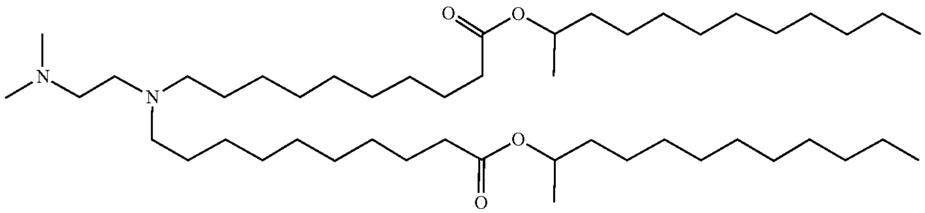 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

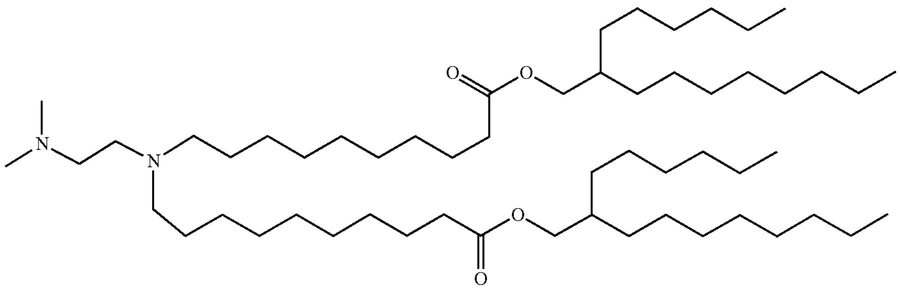 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

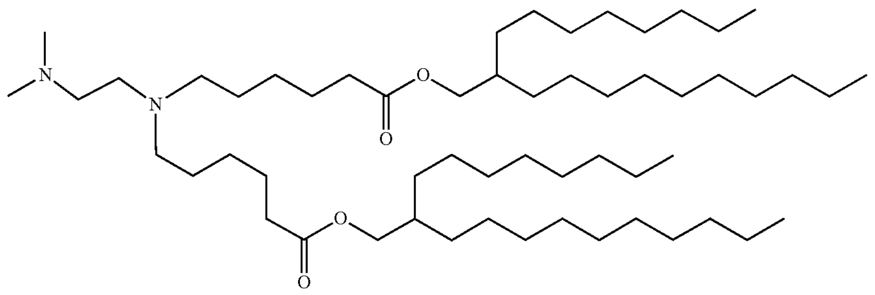 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

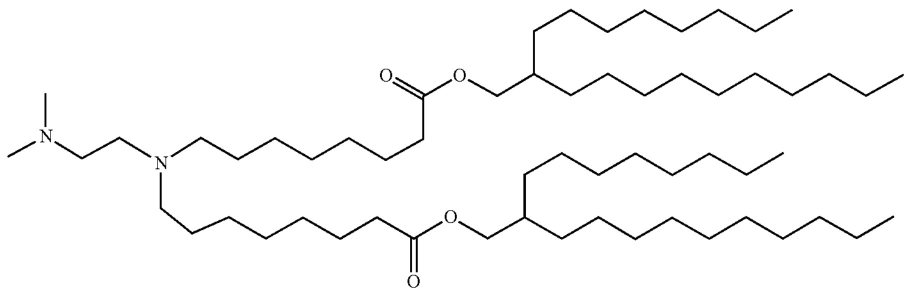 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

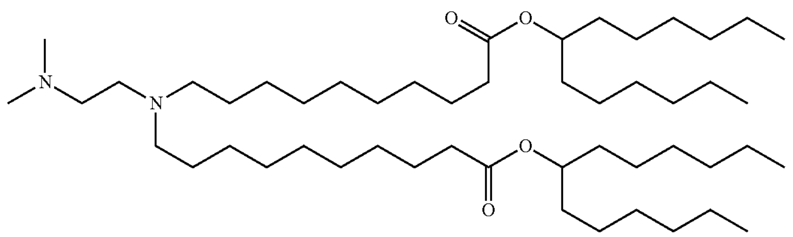 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

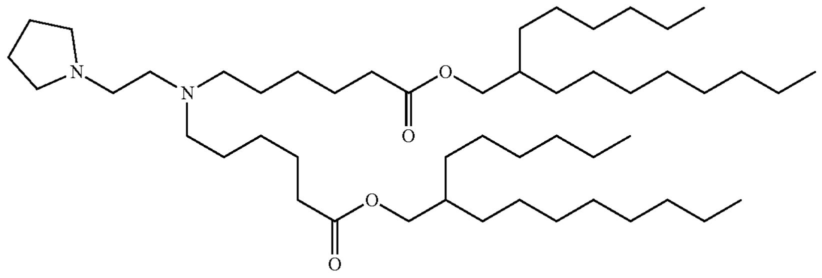 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

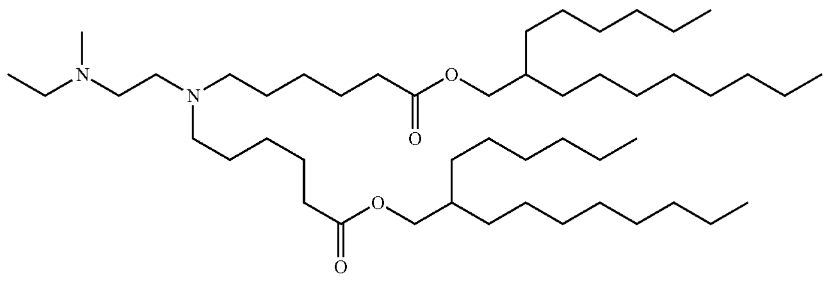 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

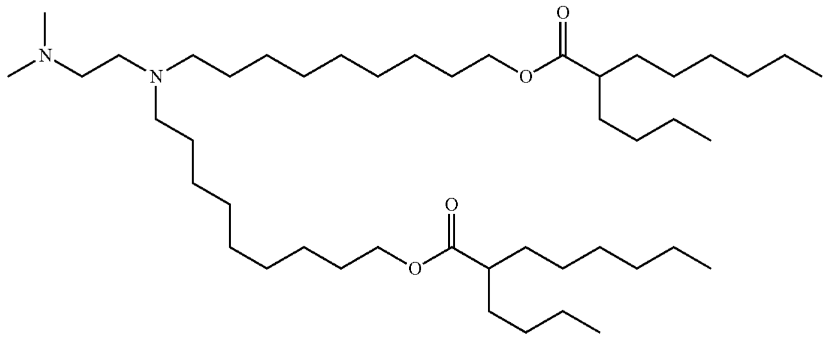 [SMILES: CCCCCCC(CCCC)C(=O)OCCCCCCCCCN(CCCCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

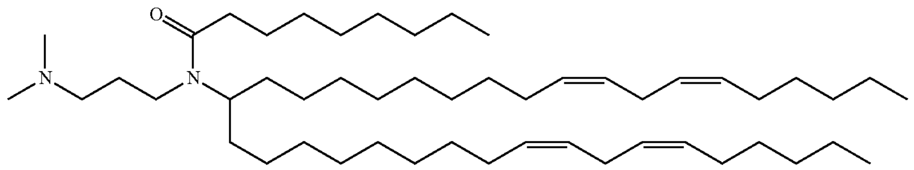 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

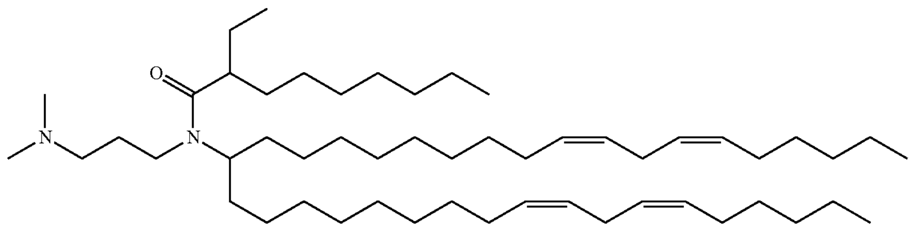 [SMILES: CCCCC/C=C\C/C=C\CCCCCCCCC(CCCCCCCC/C=C\C/C=C\CCCCC)N(CCCN(C)C)C(=O)C(CC)CCCCCCC]

and pharmaceutically acceptable salts thereof. In some embodiments, the compositions and methods of the present invention include a cationic lipid having the compound structure:

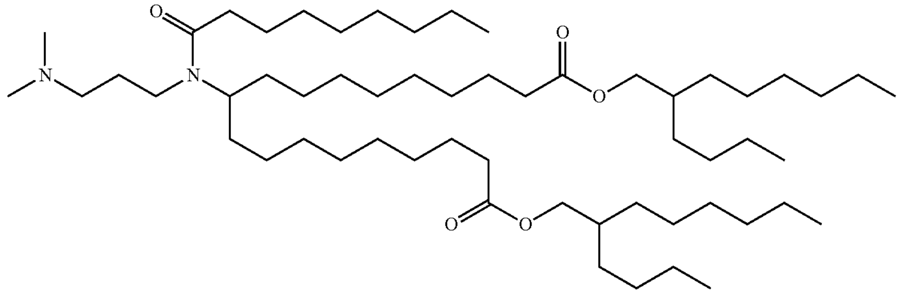 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

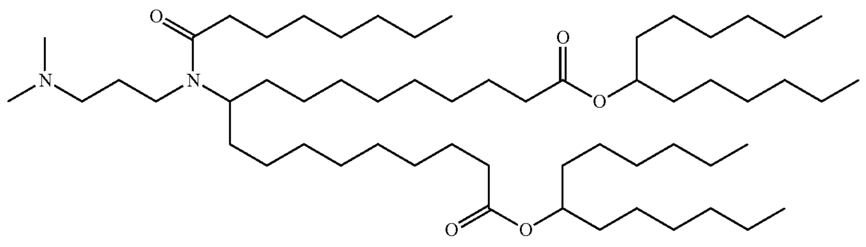 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

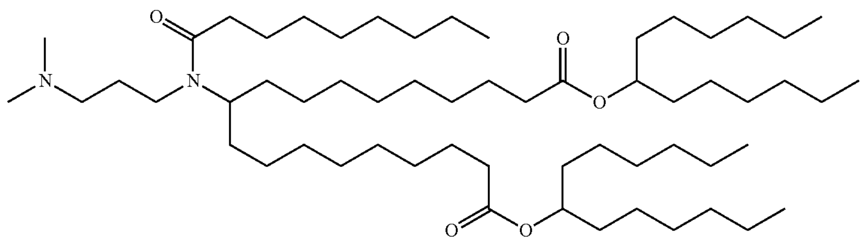 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

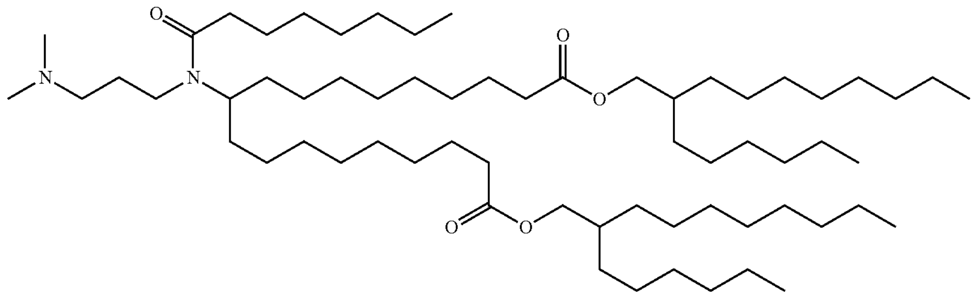 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

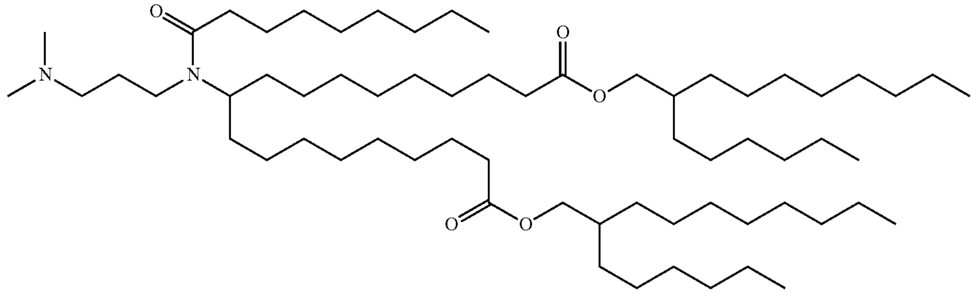 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

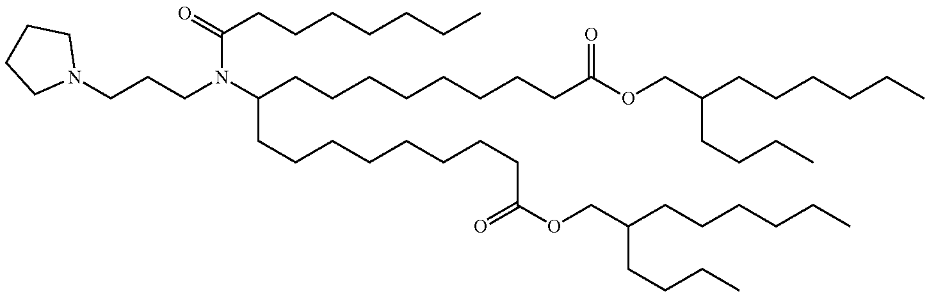 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

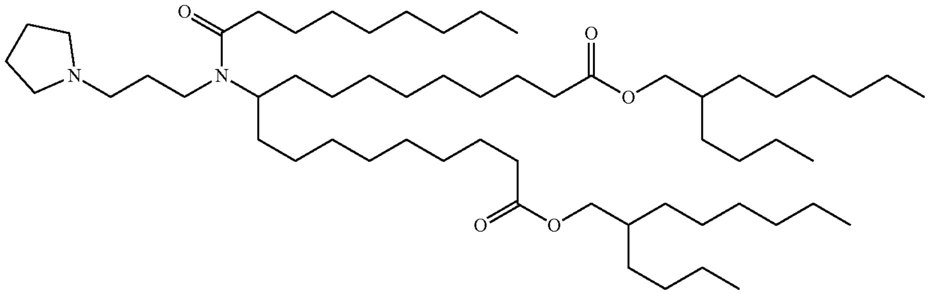 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

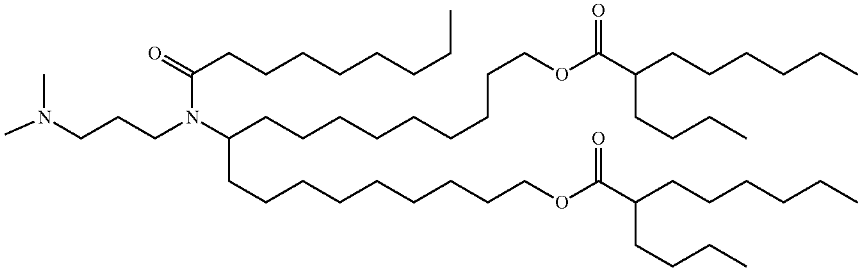 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

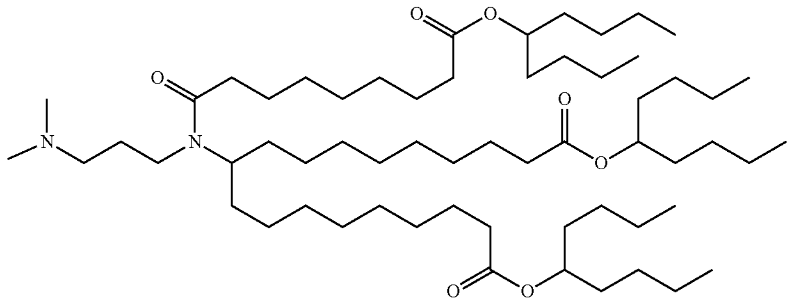 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

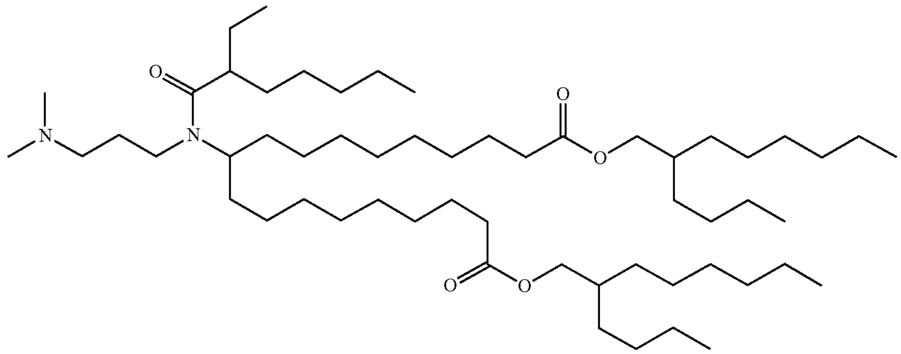 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

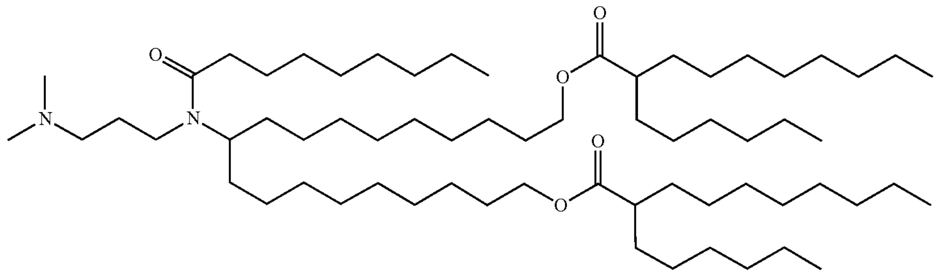 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

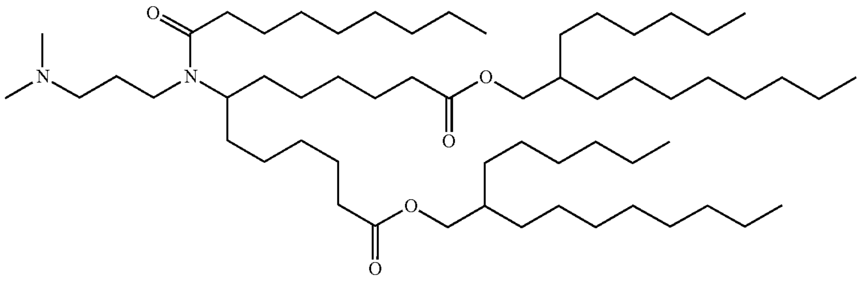 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

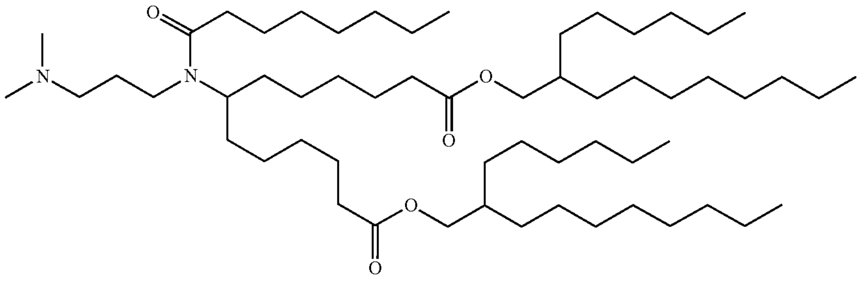 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

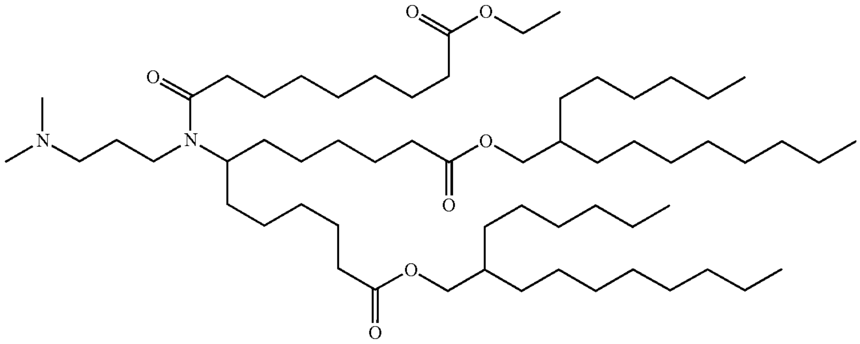 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

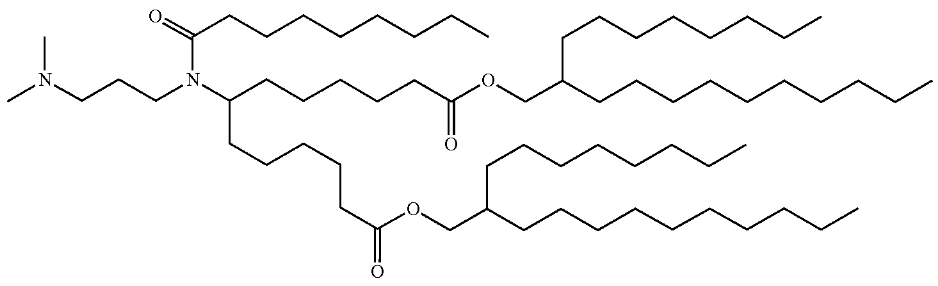 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

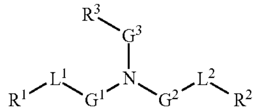

or a pharmaceutically acceptable salt thereof, wherein one of $L^1$ or $L^2$ is —O(C═O)—, —(C═O)O—, —C(═O)—, —O—, —S(O)$_x$, —S—S—, —C(═O)S—, —SC(═O)—, —NR$^a$C(═O)—, —C(═O)NR$^a$—, NR$^a$C(═O)NR$^a$—, —OC(═O)NR$^a$—, or —NR$^a$C(═O)O—; and the other of $L^1$ or $L^2$ is —O(C═O)—, —(C═O)O—, —C(═O)—, —O—, —S(O)$_x$, —S—S—, —C(═O)S—, SC(═O)—, —NR$^a$C(═O)—, —C(═O)NR$^a$—, NR$^a$C(═O)NR$^a$—, —OC(═O)NR$^a$— or —NR$^a$C(═O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; $R^3$ is H or $C_1$-$C_{12}$ alkyl; $R^1$ and $R^2$ are each independently $C_6$-$C_{24}$ alkyl or $C_6$-$C_{24}$ alkenyl; $R^3$ is H, $OR^5$, CN, —C(═O)$OR^4$, —OC(═O)$R^4$ or —$NR^5$ C(═O)$R^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

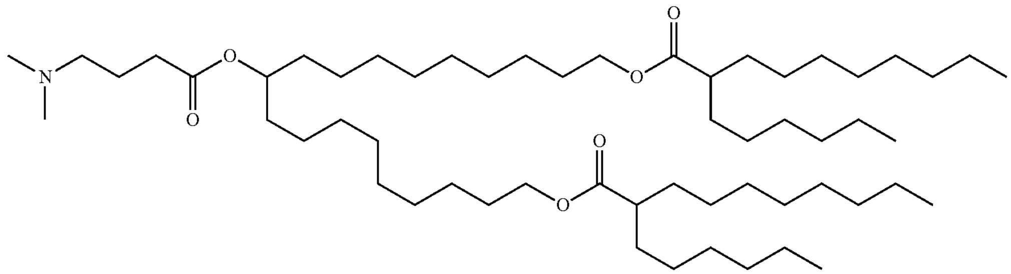 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

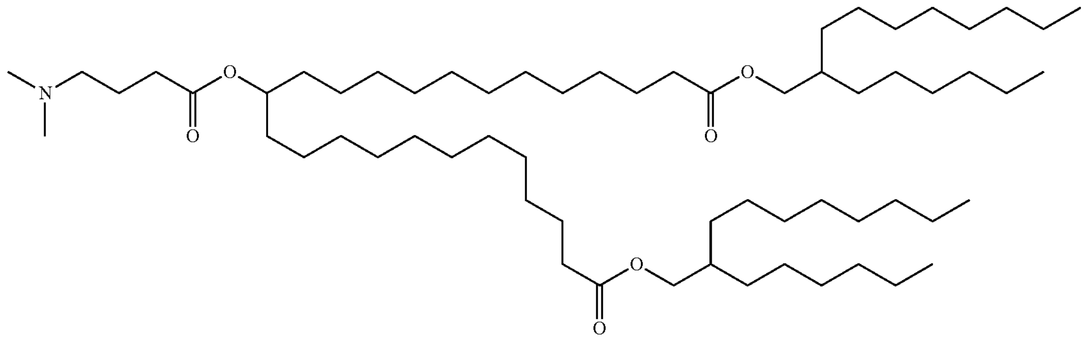 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

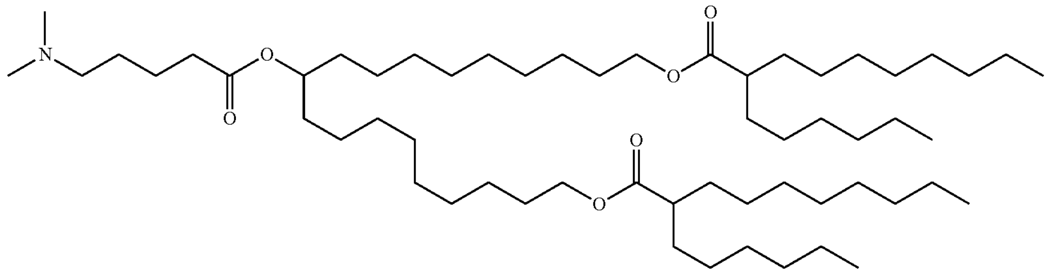 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

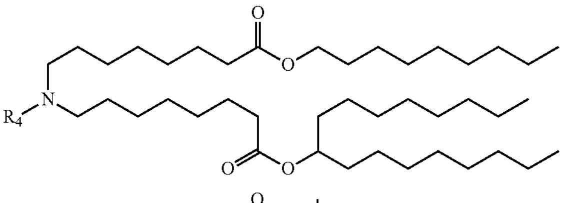

,

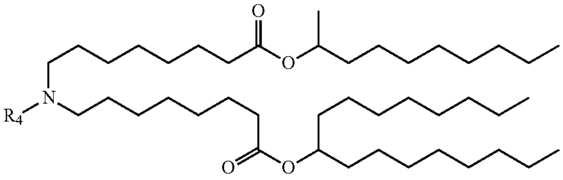

,

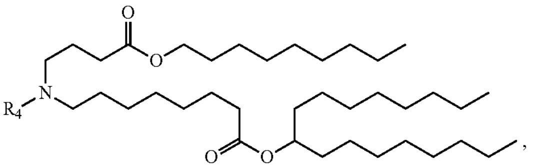

, and

-continued

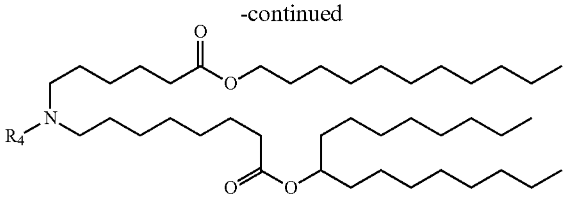

, and pharmaceutically acceptable salts thereof. For any one of these four formulas, $R_4$ is independently selected from $-(CH_2)_nQ$ and $-(CH_2)_nCHQR$; Q is selected from the group consisting of —OR, —OH, $-O(CH_2)_nN(R)_2$, —OC(O)R, $-CX_3$, —CN, —N(R)C(O)R, —N(H)C(O)R, $-N(R)S(O)_2R$, $-N(H)S(O)_2R$, $-N(R)C(O)N(R)_2$, $-N(H)C(O)N(R)_2$, —N(H)C(O)N(H)(R), $-N(R)C(S)N(R)_2$, $-N(H)C(S)N(R)_2$, —N(H)C(S)N(H)(R), and a heterocycle; and n is 1, 2, or 3. In certain embodiments, the compositions and methods of the present invention include a cationic lipid having a compound structure of:

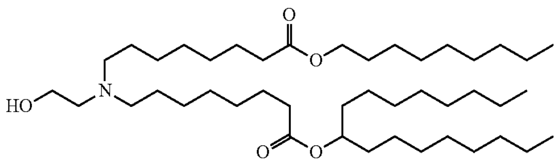 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

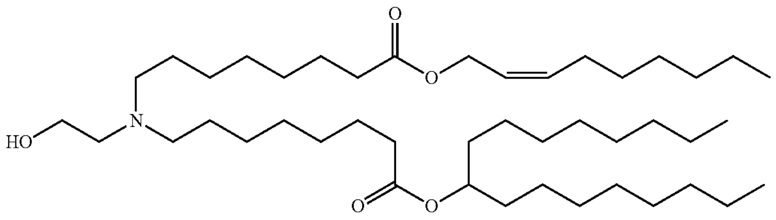 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

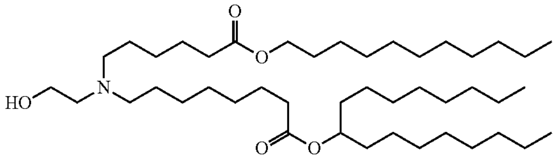 [SMILES: CCCCCCCCCCCOC(=O)CCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

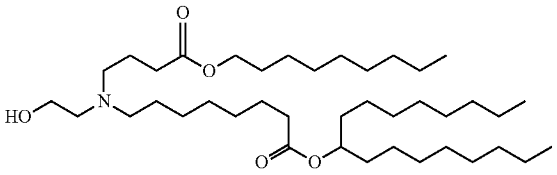 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

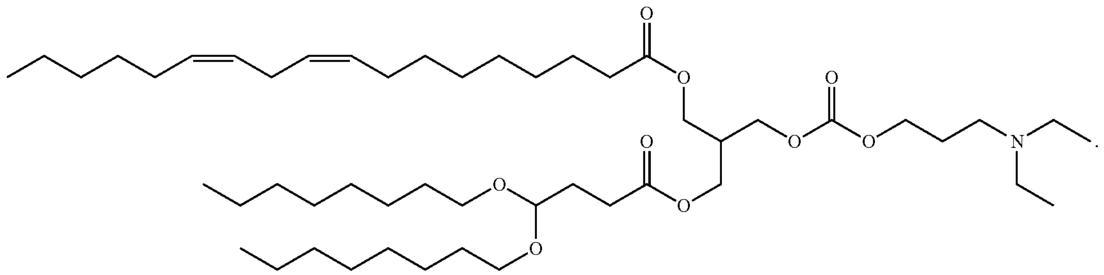 [SMILES: CCCCC/C=C\C/C=C\CCCCCCCC(=O)OCC(COC(=O)CCC(OCCCCCCCC)OCCCCCCCC)COC(=O)OCCCN(CC)CC]

and pharmaceutically acceptable salts thereof. In certain embodiments, the compositions and methods of the present invention include a cationic lipid having a compound structure of:

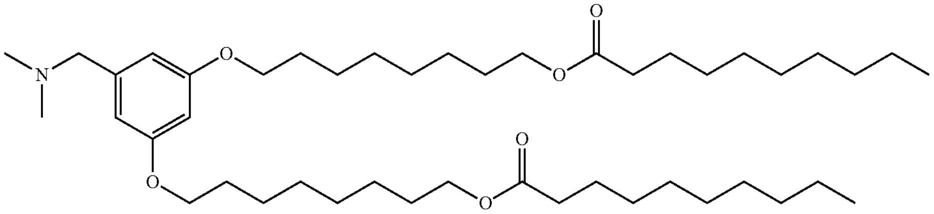 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

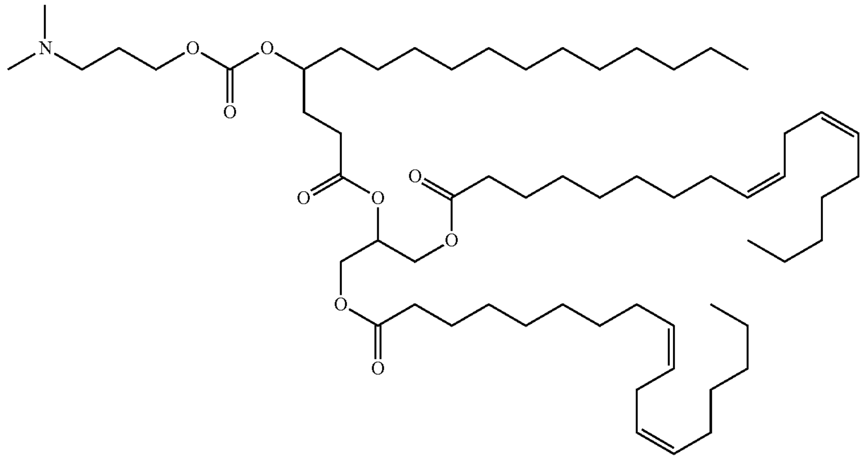 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

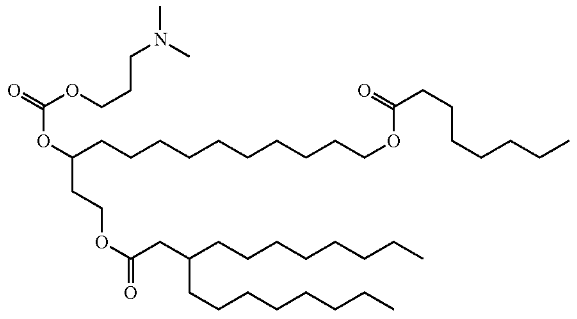 [SMILES: CCCCCCCCC(CCCCCCCC)CC(=O)OCCC(CCCCCCCCCCOC(=O)CCCCCCC)OC(=O)OCCCN(C)C]

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

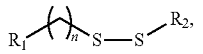

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

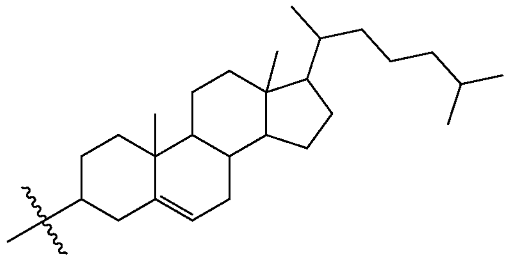

and

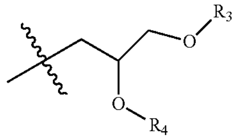

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

(HGT4001)

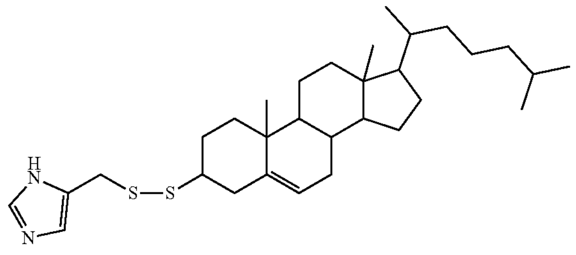

and pharmaceutically acceptable salts thereof. In certain embodiments, the compositions and methods of the present invention include a cationic lipid, "HGT4002", having a compound structure of:

(HGT4002)

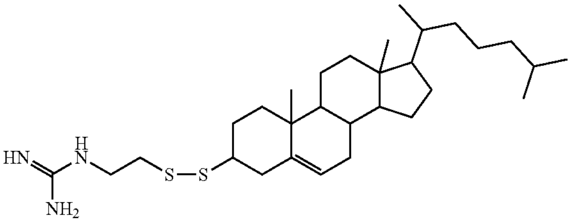

and pharmaceutically acceptable salts thereof. In certain embodiments, the compositions and methods of the present invention include a cationic lipid, "HGT4003", having a compound structure of:

Application No. 62/672,194. In certain embodiments, the compositions and methods of the present invention include a cationic lipid that has a structure according to Formula (I'), (I')

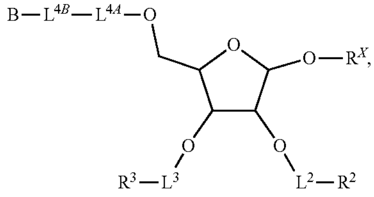

wherein:

$R^X$ is independently —H, —$L^1$—$R^1$, or —$L^{5A}$—$L^{5B}$-B';

each of $L^1$, $L^2$, and $L^3$ is independently a covalent bond, —C(O)—, —C(O)O—, —C(O)S—, or —C(O)$NR^L$—;

each $L^{4A}$ and $L^{5A}$ is independently —C(O)—, —C(O)O—, or —C(O)$NR^L$-;

(HGT4003)

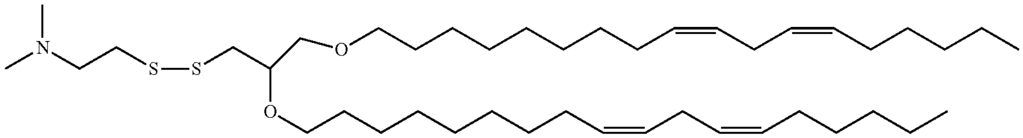

and pharmaceutically acceptable salts thereof. In certain embodiments, the compositions and methods of the present invention include a cationic lipid, "HGT4004", having a compound structure of:

each $L^{4B}$ and $L^{5B}$ is independently $C_1$-$C_{20}$ alkylene; $C_2$-$C_{20}$ alkenylene; or $C_2$-$C_{20}$ alkynylene;

each B and B' is $NR^4R^5$ or a 5- to 10-membered nitrogen-containing heteroaryl;

(HGT4004)

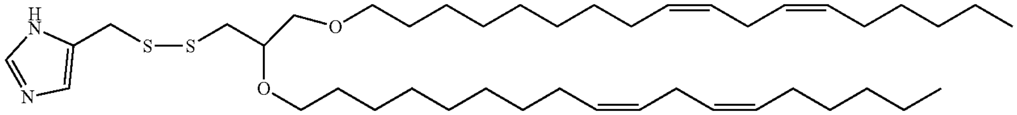

and pharmaceutically acceptable salts thereof. In certain embodiments, the compositions and methods of the present invention include a cationic lipid "HGT4005", having a compound structure of:

each $R^1$, $R^2$, and $R^3$ is independently $C_6$-$C_{30}$ alkyl, $C_6$-$C_{30}$ alkenyl, or $C_6$-$C_{30}$ alkynyl; each $R^4$ and $R^5$ is independently hydrogen, $C_1$-$C_{10}$ alkyl; $C_2$-$C_{10}$ alkenyl; or $C_2$-$C_{10}$ alkynyl; and (HGT4005)

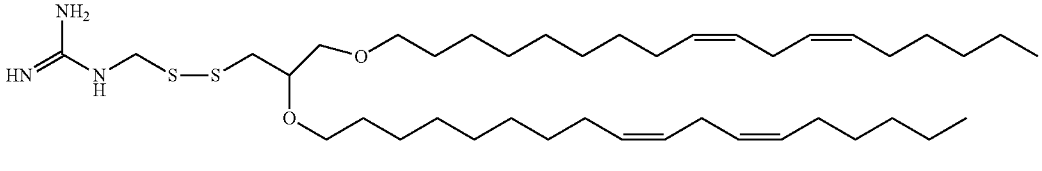

and pharmaceutically acceptable salts thereof.

Other suitable cationic lipids for use in the compositions and methods of the present invention include cleavable cationic lipids as described in U.S. Provisional Application No. 62/672,194, filed May 16, 2018, and incorporated herein by reference. In certain embodiments, the compositions and methods of the present invention include a cationic lipid that is any of general formulas or any of structures (1a)-(21a) and (1b)-(21b) and (22)-(237) described in U.S. Provisional each $R^L$ is independently hydrogen, $C_1$-$C_{20}$ alkyl, $C_2$-$C_{20}$ alkenyl, or $C_2$-$C_{20}$ alkynyl.

In certain embodiments, the compositions and methods of the present invention include a cationic lipid that is Compound (139) of 62/672,194, having a compound structure of:

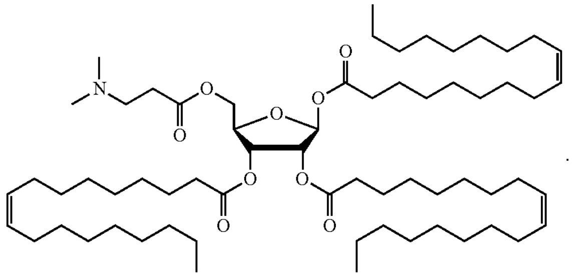

("18:1 Carbon tail-ribose lipid")

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido) ethyl]-N,N-dimethyl-1-propanaminium ("DOSPA") (Behr et al. Proc. Nat.'l Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylammonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethy 1-1-(cis,cis-9',1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N-Dilinoleylcarbamyl-3-dimethylaminopropane ("DLincarbDAP"); 1,2-Dilinoleoylcarbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N, N-dimethyl-3-[(9Z,12Z)-octadeca-9, 12-dien-1-yloxy]propane-1-amine ("Octyl-CLinDMA"); (2R)-2-((8-[(3beta)-cholest-5-en-3-yloxy]octyl)oxy)-N, N-dimethyl [(9Z,12Z)-octadeca-9, 12-dien-1-yloxy]propan-1-amine ("Octyl-CLinDMA (2R)"); (2S)-2-((8-[(3P)-cholest-5-en-3-yloxy] octyl)oxy)-N, fsl-dimethyh3-[(9Z,12Z)-octadeca-9, 12-dien-1-yloxy]propan-1-amine ("Octyl-CLinDMA (2S) "); 2,2-dilinoleyl-4-dimethylaminoethyl-[1,3]-dioxolane ("DLin-K-XTC2-DMA"); and 2-(2,2-di((9Z,12Z)-octadeca-9,1 2-dien-1-yl)-1,3-dioxolan-4-yl)-N,N-dimethylethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)—N,N-dimethyl-2,2-di((9Z, 12Z)-octadeca-9,12-dienyl)tetrahydro-3 aH-cyclopenta[d] [1,3]dioxol-5-amine ("ALNY-100") and/or 4,7,13-tris(3-oxo-3-(undecylamino)propyl)-N1,N16-diundecyl-4,7,10, 13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, or 70%, measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle In some embodiments, sterol-based cationic lipids may be use instead or in addition to cationic lipids described herein. Suitable sterol-based cationic lipids are dialkylamino-, imidazole-, and guanidinium-containing sterol-based cationic lipids. For example, certain embodiments are directed to a composition comprising one or more sterol-based cationic lipids comprising an imidazole, for example, the imidazole cholesterol ester or "ICE" lipid (3S,10R,13R,17R)-10,13-dimethyl-17-((R)-6-methylheptan-2-yl)-2,3,4,7,8,9,10,11, 12,13,14,15,16,17-tetradecahydro-1H-cyclopenta[a] phenanthren-3-yl 3-(1H-imidazol-4-yl)propanoate, as represented by structure (I) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S,10R,13R,17R)-10,13-dimethyl-17-((R)-6-methylheptan-2-yl)-2,3,4,7,8,9,10,11, 12,13,14,15,16,17-tetradecahydro-1H-cyclopenta[a] phenanthren-3-yl 3-(1H-imidazol-4-yl)propanoate, as represented by the following structure:

(ICE)

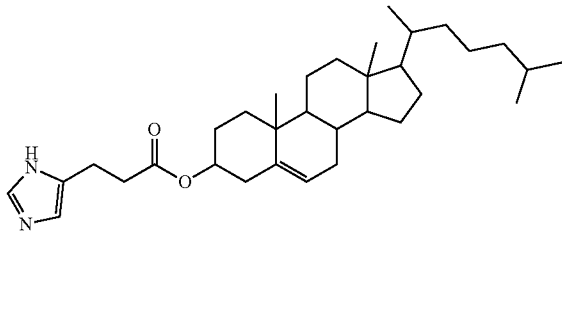

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., ICE lipid) constitutes about 30%, about 35%, about 40%, about 45%, or about 50% of the liposome by molar ratio.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (S OPE), or a mixture thereof.

In some embodiments, such non-cationic lipids may be used alone, but are preferably used in combination with other excipients, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, the percentage of cholesterol-based lipid in the liposome may be greater than 5, %, 10%, greater than 20%, greater than 30%, or greater than 40%.

PEGylated Lipids

In some embodiments, provided liposomes comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention in combination with one or more of the cationic and, in some embodiments, other lipids together which comprise the liposome. Contemplated PEG-modified lipids include, but are not limited to, a polyethylene glycol chain of up to 2 kDa, up to 3 kDa, up to 4 kDa or 5 kDa in length covalently attached to a lipid with alkyl chain(s) of C6-C20 length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613). In some embodiments, a PEG-modified or PEGylated lipid is PEGylated cholesterol or PEG-2K. In some embodiments, particularly useful exchangeable lipids are PEG-ceramides having shorter acyl chains (e.g., C14 or C18).

In some embodiments, particularly useful exchangeable lipids are PEG-ceramides having shorter acyl chains (e.g., C14 or C18). The PEG-modified phospholipid and derivitized lipids of the present invention may comprise a molar ratio from about 0% to about 15%, about 0.5% to about 15%, about 1% to about 15%, about 4% to about 10%, or about 2% of the total lipid present in the liposome. PEG-modified phospholipid and derivatized lipids may constitute at least about 5%, 10%, 20%, 30%, 40%, 50%, 60%, or 70% of the total lipids in a suitable lipid solution by weight or by molar. In some embodiments, PEGylated lipid lipid(s) constitute(s) about 30-50% (e.g., about 30-45%, about 30-40%, about 35-50%, about 35-45%, or about 35-40%) of the total lipids in a suitable lipid solution by weight or by molar.

According to various embodiments, the selection of cationic lipids, non-cationic lipids and/or PEG-modified lipids which comprise the liposome, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus, the molar ratios may be adjusted accordingly.

Liposome Formulations

A suitable liposome for the present invention may include one or more of any of the cationic lipids, non-cationic lipids, cholesterol lipids, PEGylated lipids and/or polymers described herein at various ratios. Typically, a liposome in accordance with the present invention comprises a cationic lipid, a non-cationic lipid, a cholesterol lipid and a PEGylated lipid. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; or ICE, DOPE, cholesterol and DMG-PEG2K or ICE, DOPE and DMG-PEG2K. Additional combinations of lipids are described in the art, e.g., U.S. Ser. No. 62/420,421 (filed on Nov. 10, 2016), U.S. Ser. No. 62/421,021 (filed on Nov. 11, 2016), U.S. Ser. No. 62/464,327 (filed on Feb. 27, 2017), and PCT Application entitled "Novel ICE-based Lipid Nanoparticle Formulation for Delivery of mRNA," filed on Nov. 10, 2017, the disclosures of which are included here in their full scope by reference.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEGylated lipid(s) may be between about 30-60:25-35:20-30:1-15, respectively. In some embodiments, the ratio of cationic lipid(s) to non-cationic lipid(s) to cholesterol-based lipid(s) to PEGylated lipid(s) is approximately 40:30:20:10, respectively. In some embodiments, the ratio of cationic lipid(s) to non-cationic lipid(s) to cholesterol-based lipid(s) to PEGylated lipid(s) is approximately 40:30:25:5, respectively. In some embodiments, the ratio of cationic lipid(s) to non-cationic lipid(s) to cholesterol-based lipid(s) to PEGylated lipid(s) is approximately 40:32:25:3, respectively. In some embodiments, the ratio of cationic lipid(s) to non-cationic lipid(s) to cholesterol-based lipid(s) to PEGylated lipid(s) is approximately 50:25:20:5.

Formation of Liposomes

The liposomal transfer vehicles for use in the compositions of the invention can be prepared by various techniques which are presently known in the art. The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase then may be added to the vessel with a vortexing motion which results in the formation of MLVs. Unilamellar vesicles (ULV) can then be formed by homogenization, sonication or extrusion of the multilamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (Zeta potential), targeting ligands and/or combinations thereof. In some embodiments, the one or more liposome may have a different composition of cationic lipids, neutral lipid, PEG-modified lipid and/or combinations thereof. In some embodiments the one or more liposomes may have a different molar ratio of cationic lipid, neutral lipid, cholesterol and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. In a typical embodiment, the mRNA of the invention is encapsulated in a liposome using the methods described in WO 2018/089801 (the teachings of which are incorporated herein by reference in their entirety). Briefly, the mRNA is encapsulated by mixing of a solution comprising pre-formed liposomes with mRNA such that liposomes encapsulating mRNA are formed.

Typically, the liposome-incorporated nucleic acids is completely located in the interior space of the liposome within the bilayer membrane of the liposome, although as discussed above, some of the mRNA (e.g., no more than 10% of total mRNA in the liposome composition) may also be associated with the exterior surface of the liposome membrane. The incorporation of a nucleic acid into liposomes is also referred to herein as "encapsulation". Typically, the purpose of incorporating an mRNA into a liposome is to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Liposome Size

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, the size of a liposome is determined by the length of the largest diameter of the liposome particle. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). Liposomes with a size of 80-200 nm are particularly suitable for some application. In some embodiments, a suitable liposome has a size ranging from about 10-100 nm (e.g., ranging from about 10-90 nm, 10-80 nm, 10-70 nm, 10-60 nm, or 10-50 nm). In a particular embodiment, a suitable liposome has a size less than about 100 nm.

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Liposome Formulations for MUT mRNA Delivery and Expression

This section provides exemplary liposome formulations for effective delivery and expression of MUT mRNA in vivo.

Lipid Materials

The formulations described herein include a multi-component lipid mixture of varying ratios employing one or more cationic lipids, helper lipids (e.g., non-cationic lipids and/or cholesterol-based lipids) and PEGylated lipids designed to encapsulate mRNA encoding MUT protein. Cationic lipids can include (but not exclusively) DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869), cKK-E12 (3,6-bis(4-(bis(2-hydroxydodecyl)amino)butyl)piperazine-2,5-dione), HGT5000, HGT5001, HGT4003, ICE, OF-02, dialkylamino-based, imidazole-based, guanidinium-based, etc. Helper lipids can include (but not exclusively) DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)), cholesterol, etc. The PEGylated lipids can include (but not exclusively) a poly(ethylene) glycol chain of up to 5 kDa in length covalently attached to a lipid with alkyl chain(s) of C6-C20 length.

Exemplary Formulation Protocols

A. cKK-E12

Aliquots of 50 mg/mL ethanolic solutions of cKK-E12, DOPE, cholesterol and DMG-PEG2K are mixed and diluted with ethanol to 3 mL final volume. Separately, an aqueous buffered solution (10 mM citrate/150 mM NaCl, pH 4.5) of MUT mRNA is prepared from a 1 mg/mL stock. The lipid solution was injected rapidly into the aqueous mRNA solution and shaken to yield a final suspension in 20% ethanol. The resulting liposome suspension was filtered, diafiltrated with 1× PBS (pH 7.4), concentrated and stored at 2-8° C. The final concentration, Zave, Dv(50) and Dv(90) of the MUT encapsulated mRNA were determined.

B. C12-200

Aliquots of 50 mg/mL ethanolic solutions of C12-200, DOPE, cholesterol and DMG-PEG2K are mixed and diluted with ethanol to 3 mL final volume. Separately, an aqueous buffered solution (10 mM citrate/150 mM NaCl, pH 4.5) of MUT mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1× PBS (pH 7.4), concentrated and stored at 2-8° C. The final concentration, Zave, Dv(50) and Dv(90) of the MUT encapsulated mRNA are determined.

C. HGT4003

Aliquots of 50 mg/mL ethanolic solutions of HGT4003, DOPE, cholesterol and DMG-PEG2K are mixed and diluted with ethanol to 3 mL final volume. Separately, an aqueous buffered solution (10 mM citrate/150 mM NaCl, pH 4.5) of MUT mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1× PBS (pH 7.4), concentrated and stored at 2-8° C. The final concentration, Zave, Dv(50) and Dv(90) of the MUT encapsulated mRNA are determined.

D. ICE

Aliquots of 50 mg/mL ethanolic solutions of ICE, DOPE, cholesterol and DMG-PEG2K are mixed and diluted with ethanol to 3 mL final volume. Separately, an aqueous buffered solution (10 mM citrate/150 mM NaCl, pH 4.5) of MUT mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1× PBS (pH 7.4), concentrated and stored at 2-8° C. The final concentration, Zave, Dv(50) and Dv(90) of the MUT encapsulated mRNA are determined.

E. HGT5001

Aliquots of 50 mg/mL ethanolic solutions of HGT5001, DOPE, cholesterol and DMG-PEG2K are mixed and diluted with ethanol to 3 mL final volume. Separately, an aqueous buffered solution (10 mM citrate/150 mM NaCl, pH 4.5) of MUT mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1× PBS (pH 7.4), concentrated and stored at 2-8° C. The final concentration, Zave, Dv(50) and Dv(90) of the MUT encapsulated mRNA are determined.

F. HGT5000

Aliquots of 50 mg/mL ethanolic solutions of HGT5000, DOPE, cholesterol and DMG-PEG2K are mixed and diluted with ethanol to 3 mL final volume. Separately, an aqueous buffered solution (10 mM citrate/150 mM NaCl, pH 4.5) of MUT mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1× PBS (pH 7.4), concentrated and stored at 2-8° C. The final concentration, Zave, Dv(50) and Dv(90) of the MUT encapsulated mRNA are determined.

G. DLinKC2DMA

Aliquots of 50 mg/mL ethanolic solutions of DLinKC2DMA, DOPE, cholesterol and DMG-PEG2K are mixed and diluted with ethanol to 3 mL final volume. Separately, an aqueous buffered solution (10 mM citrate/150 mM NaCl, pH 4.5) of MUT mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1× PBS (pH 7.4), concentrated and stored at 2-8° C. The final concentration, Zave, Dv(50) and Dv(90) of the MUT encapsulated mRNA are determined.

H. DODAP

Aliquots of 50 mg/mL ethanolic solutions of DODAP, DOPE, cholesterol and DMG-PEG2K are mixed and diluted with ethanol to 3 mL final volume. Separately, an aqueous buffered solution (10 mM citrate/150 mM NaCl, pH 4.5) of MUT mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1× PBS (pH 7.4), concentrated and stored at 2-8° C. The final concentration, Zave, Dv(50) and Dv(90) of the MUT encapsulated mRNA are determined.

I. DODMA

Aliquots of 50 mg/mL ethanolic solutions of DODMA, DOPE, cholesterol and DMG-PEG2K are mixed and diluted with ethanol to 3 mL final volume. Separately, an aqueous buffered solution (10 mM citrate/150 mM NaCl, pH 4.5) of MUT mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1× PBS (pH 7.4), concentrated and stored at 2-8° C. The final concentration, Zave, Dv(50) and Dv(90) of the MUT encapsulated mRNA are determined.

Clinical or therapeutic candidate mRNA formulations are selected from the exemplary codon-optimized mRNA sequences having a 5'-cap and a 3'-poly A tail, which is formulated in a suitable lipid combination as described above. Clinical relevant mRNA candidates are characterized by efficient delivery and uptake by in vivo tissue, high level of expression and sustained protein production, without detectable adverse effects in the subject to whom the therapeutic is administered, either caused by the pharmacologically active ingredient or by the lipids in the liposome, or by any excipients used in the formulation. In general, high efficiency with low dose administration is favorable for the selection process of a relevant candidate therapeutic.

Pharmaceutical Compositions

The present invention provides compositions for use in the treatment of methylmalonic acidemia (MMA). The compositions of the present invention are for use in the manufacture of a medicament for the treatment of methylmalonic acidemia (MMA).

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Provided liposomally-encapsulated or associated mRNAs, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject, the mammal, (e.g., treating, modulating, curing, preventing and/or ameliorating MMA). For example, a therapeutically effective amount may be an amount sufficient to achieve a desired therapeutic and/or prophylactic effect. Generally, the amount of a therapeutic agent (e.g., mRNA encoding an MUT protein) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

In some embodiments, the therapeutically effective dose ranges from about 0.005 mg/kg body weight to 500 mg/kg body weight, e.g., from about 0.005 mg/kg body weight to 400 mg/kg body weight, from about 0.005 mg/kg body weight to 300 mg/kg body weight, from about 0.005 mg/kg body weight to 200 mg/kg body weight, from about 0.005 mg/kg body weight to 100 mg/kg body weight, from about 0.005 mg/kg body weight to 90 mg/kg body weight, from about 0.005 mg/kg body weight to 80 mg/kg body weight, from about 0.005 mg/kg body weight to 70 mg/kg body weight, from about 0.005 mg/kg body weight to 60 mg/kg body weight, from about 0.005 mg/kg body weight to 50 mg/kg body weight, from about 0.005 mg/kg body weight to 40 mg/kg body weight, from about 0.005 mg/kg body weight to 30 mg/kg body weight, from about 0.005 mg/kg body weight to 25 mg/kg body weight, from about 0.005 mg/kg body weight to 20 mg/kg body weight, from about 0.005 mg/kg body weight to 15 mg/kg body weight, from about 0.005 mg/kg body weight to 10 mg/kg body weight.

In some embodiments, the therapeutically effective dose is greater than about 0.1 mg/kg body weight, greater than about 0.5 mg/kg body weight, from 0.1 to 1.0 mg/kg body weight, greater than about 1.0 mg/kg body weight, from 0.1 to 3.0 mg/kg body weight, greater than about 3 mg/kg body weight, greater than about 5 mg/kg body weight, greater than about 10 mg/kg body weight, greater than about 15 mg/kg body weight, greater than about 20 mg/kg body weight, greater than about 30 mg/kg body weight, greater than about 40 mg/kg body weight, greater than about 50 mg/kg body weight, greater than about 60 mg/kg body weight, greater than about 70 mg/kg body weight, greater than about 80 mg/kg body weight, greater than about 90 mg/kg body weight, greater than about 100 mg/kg body weight, greater than about 150 mg/kg body weight, greater than about 200 mg/kg body weight, greater than about 250 mg/kg body weight, greater than about 300 mg/kg body weight, greater than about 350 mg/kg body weight, greater than about 400 mg/kg body weight, greater than about 450 mg/kg body weight, greater than about 500 mg/kg body weight.

In a preferred embodiment, the therapeutically effective dose is 0.2 mg/kg body weight, 0.5 mg/kg body weight or 1.0 mg/kg body weight. In a more preferred embodiment, the therapeutically effective dose is 0.2 mg/kg body weight or 0.5 mg/kg body weight. In the most preferred embodiment, the therapeutically effective dose is 0.2 mg/kg body weight.

The "effective dose or effective amount" for the purposes herein may be determined by such relevant considerations as are known to those of ordinary skill in experimental clinical research, pharmacological, clinical and medical arts.

A therapeutic low dose is a dose that is less than the maximal effective dose in the subject but is a dose that shows therapeutic effectiveness. Determining a therapeutic low dose is important in developing a formulation into a drug. A therapeutic low dose may be higher than the minimal effective low dose. A therapeutic low dose may be in the range where the dose is optimally effective without causing any adverse effect.

In some embodiments, an effective therapeutic low dose is administered to the mammal wherein the therapeutic low dose of the pharmaceutical composition comprising an mRNA encoding methylmalonyl-CoA mutase protein is administered at a dosing interval sufficient to reduce for the period of the dosing interval or longer the level of at least one symptom or biomarker associated with MMA in the mammal relative to its state prior to the treatment.

In some embodiments the mRNA encoding methylmalonyl-CoA mutase protein is administered at a dose of 1 mg/kg or less of mRNA at a dosing interval of once every two weeks or a longer dosing interval, wherein the dose and dosing interval is sufficient to reduce for the period of the dosing interval or longer, the level of at least one symptom or biomarker associated with MMA in the mammal relative to the state prior to the treatment. In some embodiments the mRNA encoding methylmalonyl-CoA mutase protein is administered at a dose of 0.5 mg/kg or less of mRNA. In some embodiments the mRNA encoding methylmalonyl-CoA mutase protein is administered at a dose of 0.45 mg/kg or less of mRNA. In some embodiments the mRNA encoding methylmalonyl-CoA mutase protein is administered at a dose of 0.40 mg/kg or less of mRNA. In some embodiments the mRNA encoding methylmalonyl-CoA mutase protein is administered at a dose of 0.35 mg/kg or less of mRNA. In some embodiments the mRNA encoding methylmalonyl-CoA mutase protein is administered at a dose of 0.30 mg/kg or less of mRNA. In some embodiments the mRNA encoding methylmalonyl-CoA mutase protein is administered at a dose of 0.25 mg/kg or less. In some embodiments the mRNA encoding methylmalonyl-CoA mutase protein is administered at a dose of 0.2 mg/kg or less.

In some embodiments the mRNA encoding methylmalonyl-CoA mutase protein is administered at a dose of 0.15 mg/kg or less, administered at a dosing interval of once in 2 weeks or longer, and wherein the dose of 0.15 mg/kg or less at an interval of 2 weeks or longer reduces at least one symptom or the level of at least one biomarker associated with MMA in the mammal for the period of the dosing interval of 2 weeks or longer. In some embodiments the mRNA encoding methylmalonyl-CoA mutase protein is administered at a dose of 0.125 mg/kg or less. In some embodiments the mRNA encoding methylmalonyl-CoA mutase protein is administered at a dose of 0.10 mg/kg or less. In some embodiments the mRNA encoding methylmalonyl-CoA mutase protein is administered at a dose of 0.09 mg/kg or less of mRNA, or at less than 0.08 mg/kg of mRNA, or at less than 0.07 mg/kg of mRNA, or at less than 0.06 mg/kg of mRNA, or at less than 0.05 mg/kg of mRNA, or at less than 0.04 mg/kg of mRNA, or at less than 0.03 mg/kg of mRNA, or at less than 0.02 mg/kg of mRNA, at less than 0.01 mg/kg of mRNA, or at 0.005 mg/kg of mRNA at a dosing interval sufficient to reduce the level of at least one symptom or biomarker associated with MMA in the mammal relative to the state prior to the treatment.

In some embodiments, the therapeutic low dose of the pharmaceutical composition comprising mRNA encoding methylmalonyl-CoA mutase protein is 0.01 mg/kg of mRNA at a dosing interval sufficient to reduce the level of at least one symptom or biomarker associated with MMA in the mammal relative to the state prior to the treatment.

In some embodiments, the therapeutic low dose of the pharmaceutical composition comprising mRNA encoding methylmalonyl-CoA mutase protein is about 0.005 mg/kg of mRNA at a dosing interval of once every 2 weeks or longer, wherein the level of at least one symptom or biomarker associated with MMA in the mammal is reduced at maintained at a reduced level relative to the state prior to the treatment for the period of the dosing interval or longer.

In some embodiments the mammal is a human. A suitable therapeutic dose that may be applicable for a human being can be derived based on animal studies. A basic guideline for deriving a human equivalent dose from studies performed in animals can be obtained from the U.S>Food and Drug Administration (FDA) website at https://www.fda.gov/downloads/drugs/guidances/ucm078932.pdf, entitled, "Guidance for Industry Estimating the Maximum Safe Starting Dose in Initial Clinical Trials for Therapeutics in Adult Healthy Volunteers." Based on the guidelines for allometric scaling, a suitable dose of, for example, 0.6 mg/kg in a mouse, would relate to a human equivalent dose of 0.0048 mg/kg. Thus, considering the derived human equivalent dose, a projected human therapeutic dose can be derived based on studies in other animals.

Administration of hMUT mRNA at doses of 0.2-1.0 mg/kg body weight has been shown to be effective in a number of different mouse models of MMA. Therapeutically relevant levels of protein expression have been achieved with various codon-optimized mRNAs encoding human methylmalonyl-CoA mutase protein (hMUT). mRNAs with modified as well as unmodified nucleotides have been tested. In specific embodiments, the coding region of the hMUT mRNA has a nucleotide sequence at least 80%, 85%, 90% or 95% identical to SEQ ID NOs. 4, 5 or 12. In certain embodiments, the coding region of the hMUT mRNA has the nucleotide sequence of SEQ ID NOs. 4, 5 or 12. In a typical embodiment, the nucleotides of the mRNA are unmodified. In other embodiments, the nucleotides of the mRNA are modified to further enhance hMUT expression.

In some embodiments, the projected human therapeutic dose is about 0.001-0.010 mg/kg body weight. In a preferred embodiment, the projected human therapeutic dose is 0.001 mg/kg body weight, 0.005 mg/kg body weight or 0.010 mg/kg body weight. In a more preferred embodiment, the projected human therapeutic dose is 0.001 mg/kg body weight or about 0.005 mg/kg body weight. In the most preferred embodiment, the projected human therapeutic dose is 0.001 mg/kg body weight.

In a preferred embodiment, the projected human therapeutic hMUT mRNA dose of 0.001 mg/kg body weight, 0.005 mg/kg body weight or 0.010 mg/kg body weight is administered weekly. In a more preferred embodiment, the projected human therapeutic hMUT mRNA dose of 0.001 mg/kg body weight or about 0.005 mg/kg body weight is administered weekly. In the most preferred embodiment, the projected human therapeutic hMUT mRNA dose of 0.001 mg/kg body weight is administered weekly, however, in some instances, a hMUT mRNA dose of about 0.01 mg/kg body weight or about 0.03 mg/kg body weight may be more effective. In some embodiments, the human subject receiving a therapeutic hMUT mRNA dose every two weeks is suffering from mild MMA. In other embodiments, the human subject receiving a therapeutic hMUT mRNA dose every two weeks is suffering from severe MMA.

In another embodiment, the projected human therapeutic hMUT mRNA dose of 0.01 mg/kg body weight, 0.02 mg/kg body weight or 0.03 mg/kg body weight is administered every two weeks. In some embodiments, the projected human therapeutic hMUT mRNA dose of 0.02 mg/kg body weight or about 0.03 mg/kg body weight is administered every two weeks. In certain embodiments, the human subject receiving a therapeutic hMUT mRNA dose every two weeks is suffering from mild MMA. In other embodiments, the human subject receiving a therapeutic hMUT mRNA dose every two weeks is suffering from severe MMA. Higher doses (e.g. about 0.03 mg/kg body weight or higher) may be required to treat the most severe forms of MMA.

In some embodiments, a pharmaceutical composition comprising a 10-1000m dose of hMUT mRNA is administered to a subject. Typically, a pharmaceutical composition comprising a 50 μg, 75 μg, 100 μg, 200 μg, 300 μg, 400 μg or 800 μg dose of hMUT mRNA is administered to a subject. In a preferred embodiment, a pharmaceutical composition comprising a dose of 50 μg to 500 μg hMUT mRNA (e.g., 75 μg, 150 μg, 350 μg) is administered to a subject. In the most preferred embodiment, a pharmaceutical composition comprising a dose of 100 μg to 250 μg hMUT mRNA is administered to a subject, however, higher doses may be administered to treat e.g. severe MMA. For example, doses between about 300 μg and about 3 mg (e.g. about 0.5 mg, 1 mg or 2 mg) may be required to treat patients with moderate to severe forms of MMA. Typically, a dose is administered weekly or biweekly intervals. Weekly dosing may be required for human subjects suffering from a moderate or severe form of MMA. Depending on the disease phenotype and/or effectiveness of treatment, the hMUT mRNA may be administered less often, e.g. every two weeks. For example, human subjects suffering from mild MMA may be dosed every other week (i.e. biweekly).

In some embodiments, the projected human therapeutic low dose of the pharmaceutical composition comprising mRNA encoding methylmalonyl-CoA mutase protein is about 0.005 mg/kg of mRNA at a dosing interval of once every 2 weeks or longer, wherein the level of at least one symptom or biomarker associated with MMA in the mammal is reduced at maintained at a reduced level relative to the state prior to the treatment for the period of the dosing interval or longer. In some embodiments, the projected human therapeutic low dose of the pharmaceutical composition comprising mRNA encoding methylmalonyl-CoA mutase protein is about 0.001 mg/kg of mRNA or higher. In some embodiments, the projected human therapeutic low dose of the pharmaceutical composition comprising mRNA encoding methylmalonyl-CoA mutase protein is about 0.002 mg/kg of mRNA or higher. In some embodiments, the projected human therapeutic low dose of the pharmaceutical composition comprising mRNA encoding methylmalonyl-CoA mutase protein is about 0.003 mg/kg of mRNA or higher. In some embodiments, the projected human therapeutic low dose of the pharmaceutical composition comprising mRNA encoding methylmalonyl-CoA mutase protein is about 0.004 mg/kg of mRNA or higher. In some embodiments, the projected human therapeutic low dose of the pharmaceutical composition comprising mRNA encoding methylmalonyl-CoA mutase protein is about 0.005 mg/kg of mRNA or higher.

In some embodiments, the dosing interval is once every 15 days or longer, or once every 20 days or longer, or once every 21 days, or once every 22 days, or once every 23 days, or once every 24 days, or once every 25 days, once every 26 days, or once every 27 days, or once every 28 days, or once every 29 days or longer, or once every 30 days or longer, or once every 31 days or longer. In some embodiments, the dosing interval is once every 40, 45 or 50 days or 60 days, or any number of days in between. In some embodiments, the dosing interval is once every 80, 90 or 120 days or 150 days, or any number of days in between.

In some embodiments, the therapeutic low dose is administered at a dosing interval of once every 2 weeks or longer, which is sufficient to reduce the level of at least one symptom or biomarker associated with MMA in the mammal relative to the state prior to the treatment. In some embodiments, the therapeutic low dose is administered at a dosing interval of once every 3 weeks or longer, which is sufficient to reduce the level of at least one symptom or biomarker associated with MMA in the mammal relative to the state prior to the treatment. In some embodiments, the dosing interval is once every 4 weeks or longer. In some embodiments, the dosing interval is once every 5 weeks or longer. In some embodiments, the dosing interval is once every 6 weeks or longer. In some embodiments, the dosing interval is once every 8 weeks or longer. In some embodiments, the dosing interval is once every 12 or 15 or 18 weeks or longer.

In some embodiments, the dosing interval is once a month. In some embodiments, the dosing interval is once in every two months. In some embodiments, the dosing interval is once every three months, or once every four months or once every five months or once every six months or anywhere in between.

In some embodiments, administering the provided composition results in an increased methylmalonyl-CoA mutase mRNA expression level in a biological sample from a subject as compared to a baseline expression level before treatment. Typically, the baseline level is measured immediately before treatment. Biological samples include, for example, whole blood, serum, plasma, urine and tissue samples (e.g., muscle, liver, skin fibroblasts). In some embodiments, administering the provided composition results in an increased MUT mRNA expression level by at least about 10%, 20%, 30%, 40%, 50%, 60%, 70%, 80%, 90%, or 95% as compared to the baseline level immediately before treatment. In some embodiments, administering the provided composition results in an increased MUT mRNA expression level as compared to a MUT mRNA expression level in subjects who are not treated According to the present invention, a therapeutically effective dose of the provided composition, when administered regularly, results in an increased MUT protein expression or activity level in a subject as compared to a baseline MUT protein expression or activity level before treatment. Typically, the MUT protein expression or activity level is measured in a biological sample obtained from the subject such as blood, plasma or serum, urine, or solid tissue extracts. In some embodiments, the administering of a composition of the invention results in MUT expression detectable in the liver. Typically, administering of a composition of the invention results in MUT expression in the liver at or above about 100 ng/mg of total protein. For example, administering of a composition of the invention results in MUT expression in the liver at or above about 150 ng/mg of total protein. The baseline level is measured immediately before treatment. In some embodiments, administering the provided composition results in an increased MUT protein expression or activity level in a biological sample (e.g., plasma/serum or urine) by at least about 10%, 20%, 30%, 40%, 50%, 60%, 70%, 80%, 90%, or 95% as compared to a baseline level before treatment. In some embodiments, administering the provided composition results in an increased MUT protein expression or activity level in a biological sample (e.g., plasma/serum or urine) by at least about 10%, 20%, 30%, 40%, 50%, 60%, 70%, 80%, 90%, or 95% as compared to a baseline level before treatment for at least 24 hours, at least 48 hours, at least 72 hours, at least 3 days, at least 4 days, at least 5 days, at least 6 days, at least 7 days, at least 8 days, at least 9 days, at least 10 days, at least 11 days, at least 12 days, at least 13 days, at least 14 days, or at least 15 days.

In some embodiments, the therapeutic low dose is sufficient to achieve at least some stabilization, improvement or elimination of symptoms and other indicators, such as biomarkers, are selected as appropriate measures of disease progress, regression or improvement by those of skill in the art. For example, a suitable amount and dosing regimen is one that causes at least transient protein (e.g., enzyme) production. In some embodiments, the symptom comprises accumulation of methylmalonic acid in the tissue or body fluids. This is caused, by the lack of conversion methylmalonyl-CoA into succinyl-CoA due to lack of the functional enzyme methylmalonyl-CoA mutase.

In some embodiments, the therapeutic low dose is sufficient to reduce the level of one or more biomarkers of the disease related to MMA for at least the period of the dosing interval, compared to a level prior to the initial administration of the therapeutic composition. In some embodiments, the biomarker is plasma methylmalonic acid accumulation level. In some embodiments, the biomarker is plasma 2-methylcitrate. In some embodiments, the biomarker is propionate.

Typically, the methylmalonic acid level before or after the treatment may be measured in a biological sample obtained from the subject such as, blood, plasma, serum, urine, or solid tissue extracts. When reference is made to levels of methylmalonic acid in the blood, this is to be understood as referring to the concentration of methylmalonic acid measured in plasma or serum. The baseline methylmalonic acid level is measured immediately before treatment. In some embodiments, treatment according to the present invention results in an reduction of the methylmalonic acid level in a biological sample (e.g., blood, plasma/serum, or urine) obtained from the subject by at least 10%, 20%, 30%, 40%, 50%, 60%, 70%, 80%, 90%, or 95% as compared to the baseline methylmalonic acid level, respectively.

For example, in some embodiments, weekly or biweekly administration of a projected human therapeutic dose is about 0.005-0.05 mg/kg body weight result in an at least 50% reduction of the methylmalonic acid level in plasma. More typically, weekly or biweekly administration of such a therapeutic dose results in an at least 80% reduction of the methylmalonic acid level in plasma. In some embodiments, the projected human therapeutic dose is about 0.01 mg/kg body weight, about 0.02 mg/kg body weight or about 0.03 mg/kg body weight. In some embodiments, an effective therapeutic dose results in an reduction of the methylmalonic acid level in plasma obtained from the subject by at least 30%, 40%, 50%, 60%, 70%, 80%, 90%, or 95% as compared to the baseline methylmalonic acid level, respectively. An effective therapeutic dose typically results in a reduction of the methylmalonic acid level in plasma of between 50% and 90%, e.g. between 60% and 80%, 5 days after dosing. In some embodiments, an effective therapeutic dose results in a reduction of the methylmalonic acid level in plasma of between 50% and 90%, e.g. between 60% and 80%, 10 days after dosing.

In some embodiments, methylmalonic acid levels are measured before and after the treatment from blood plasma. In some embodiments, methylmalonic acid levels are measured before and after the treatment from tissues. In some embodiments, methylmalonic acid levels are measured before and after the treatment from the liver. In some embodiments, methylmalonic acid levels are measured before and after the treatment from the brain.

In some embodiments, the therapeutically effective dose is sufficient to reduce and maintain reduced methylmalonic acid level in the tissue or a body fluid of the subject for the period of the therapeutic interval or longer.

It has been found that weekly administration of 0.2 mg/kg hMUT mRNA to $Mut^{-/-}$ mice is sufficient to maintain an approximately 80% reduction of the plasma methylmalonic acid level and increase survival (An et al., 2017, supra).

In some embodiments, the therapeutically effective dose is such that a single administration of the pharmaceutical product is sufficient to reduce and maintain reduced methylmalonic acid level in the tissue or a body fluid of the subject relative to a level prior to the treatment for about 2 months. In some embodiments, the therapeutically effective dose is such that a single administration of the pharmaceutical product is sufficient to reduce and maintain reduced ammonia level in the tissue or a body fluid of the subject relative to a level prior to the treatment for at least about 8 weeks, or for about 7 weeks, or for about 6 weeks, or for about 5 weeks or for about 4 weeks.

In some embodiments, the therapeutically effective dose of the pharmaceutical composition is sufficient to reduce and maintain the plasma methylmalonic acid level of the administered mammalian subject at less than 500 μmol/L for the period of dosing interval or longer. In some embodiments, the plasma methylmalonic acid level of the administered mammalian subject at reduced to and maintained at less than 400 μmol/L for the period of dosing interval or longer. In some embodiments, the plasma methylmalonic acid level of the administered mammalian subject at reduced to and maintained at less than 300 μmol/L for the period of dosing interval or longer. In some embodiments, the plasma methylmalonic acid level of the subject at reduced to and maintained at less than 250 μmol/L for the period of dosing interval. In some embodiments, the plasma methylmalonic acid level of the administered mammalian subject at reduced to and maintained at less than 200 μmol/L for the period of dosing interval or longer.

Administration of a therapeutically effective dose of the pharmaceutical composition may result in the plasma methylmalonic acid level being reduced to and maintained at less than 200 μmol/L for the period of dosing interval or longer. Preferably, administration of a therapeutically effective dose of the pharmaceutical composition may result in the plasma methylmalonic acid level being reduced to and maintained at less than 100 μmol/L for the period of dosing interval or longer. For example, administration of a therapeutically effective dose of the pharmaceutical composition may result in the plasma methylmalonic acid level being reduced to and maintained at less than 50 μmol/L for the period of dosing interval or longer.

In some embodiments, a single administration of the pharmaceutical product at the low therapeutic dose is sufficient to reduce the plasma methylmalonic acid accumulation level of the administered mammalian subject to less than 200 μmol/L or less for the period of the therapeutic interval or longer.

In some embodiments, a weekly administration of the pharmaceutical product at the low therapeutic dose is sufficient to reduce the plasma methylmalonic acid accumulation level of the administered mammalian subject to less than 200 μmol/L or less, for period of the therapeutic interval or longer.

In some embodiments, a therapeutically effective dose of the provided composition, when administered regularly, results in decreased plasma methylmalonic acid level in a subject as compared to a baseline, which is the level of methylmalonic acid prior to any treatment. In some embodiments the plasma methylmalonic acid level is decreased by at least 50%, or by at least 75%. In some embodiments the plasma methylmalonic acid may be reduced by 50-90%.

In some embodiments, the therapeutically effective dose of the pharmaceutical composition is sufficient to reduce and maintain the urine methylmalonic acid level of the administered mammalian subject at less than 1000 mmol/mol creatinine for the period of dosing interval or longer. In some embodiments, the therapeutically effective dose of the pharmaceutical composition is sufficient to reduce and maintain the urine methylmalonic acid level of the administered mammalian subject at less than 500 mmol/mol creatinine for the period of dosing interval or longer. In some embodiments, the therapeutically effective dose of the pharmaceutical composition is sufficient to reduce and maintain the urine methylmalonic acid level of the administered mammalian subject at less than 200 mmol/mol creatinine for the period of dosing interval or longer.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal.

In some embodiments, the therapeutically effective dose comprising the mRNA encoding methylmalonyl-CoA mutase protein is administered to the subject by intramuscular administration.

In some embodiments, the therapeutically effective dose comprising the mRNA encoding methylmalonyl-CoA mutase protein is administered to the subject by subcutaneous administration.

In particular embodiments, the intramuscular administration is to a muscle selected from the group consisting of skeletal muscle, smooth muscle and cardiac muscle. In some embodiments the administration results in delivery of the mRNA to a muscle cell. In some embodiments the administration results in delivery of the mRNA to a hepatocyte (i.e., liver cell). In a particular embodiment, the intramuscular administration results in delivery of the mRNA to a muscle cell.

Most commonly, the therapeutically effective dose comprising the mRNA encoding methylmalonyl-CoA mutase protein is administered to the subject by intravenous administration.

Alternatively or additionally, liposomally encapsulated mRNAs and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

In particular embodiments, MUT encoding mRNA is administered intravenously, wherein intravenous administration is associated with delivery of the mRNA to hepatocytes.

In some embodiments, the therapeutically effective dose comprising the mRNA encoding methylmalonyl-CoA mutase protein is administered for suitable delivery to the mammal's liver. In some embodiments, the therapeutically effective dose comprising the mRNA encoding methylmalonyl-CoA mutase protein is administered for suitable expression in hepatocytes of the administered mammal.

Provided methods of the present invention contemplate single as well as multiple administrations of a therapeutically effective amount of the therapeutic agents (e.g., mRNA encoding an MUT protein) described herein. Therapeutic agents can be administered at regular intervals, depending on the nature, severity and extent of the subject's condition (e.g., MMA). In some embodiments, a therapeutically effective amount of the therapeutic agents (e.g., mRNA encoding an MUT protein) of the present invention may be administered intrathecally periodically at regular intervals (e.g., once every year, once every six months, once every five months, once every three months, bimonthly (once every two months), monthly (once every month), biweekly (once every two weeks), twice a month, once every 30 days, once every 28 days, once every 14 days, once every 10 days, once every 7 days, weekly, twice a week, daily or continuously).

In some embodiments, provided liposomes and/or compositions are formulated such that they are suitable for extended-release of the mRNA contained therein. Such extended-release compositions may be conveniently administered to a subject at extended dosing intervals. For example, in one embodiment, the compositions of the present invention are administered to a subject twice a day, daily or every other day. In some embodiments, the compositions of the present invention are administered to a subject twice a week, once a week, once every 7 days, once every 10 days, once every 14 days, once every 28 days, once every 30 days, once every two weeks, once every three weeks, once every four weeks, once a month, twice a month, once every six weeks, once every eight weeks, once every other month, once every three months, once every four months, once every six months, once every eight months, once every nine months or annually.

In a preferred embodiment, the compositions of the present invention are administered to a subject once a week, once every two weeks or once a month. In a more preferred embodiment, the compositions of the present invention are administered to a subject once every two weeks or once every month. In the most preferred embodiment, the compositions of the present invention are administered to a subject once every month.

In some embodiments the mRNA is administered concurrently with an additional therapy.

Also contemplated are compositions and liposomes which are formulated for depot administration (e.g., intramuscularly, subcutaneously, intravitreally) to either deliver or release a mRNA over extended periods of time. Preferably, the extended-release means employed are combined with modifications made to the mRNA to enhance stability.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts. According to the present invention, a therapeutically effective dose of the provided composition, when administered regularly, results in at least one symptom or feature of MMA is reduced in intensity, severity, or frequency or has delayed onset.

Also contemplated herein are lyophilized pharmaceutical compositions comprising one or more of the liposomes disclosed herein and related methods for the use of such compositions as disclosed for example, in International Patent Application PCT/US12/41663, filed Jun. 8, 2012, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

In some embodiments, the pharmaceutical composition comprises a lyophilized liposomal delivery vehicle that comprises a cationic lipid, a non-cationic lipid, a PEG-modified lipid and cholesterol. In some embodiments, the pharmaceutical composition has a Dv50 of less than 500 nm, 300 nm, 200 nm, 150 nm, 125 nm, 120 nm, 100 nm, 75 nm, 50 nm, 25 nm or smaller upon reconstitution. In some embodiments, the pharmaceutical composition has a Dv90 of less than 750 nm, 700 nm, 500 nm, 300 nm, 200 nm, 150 nm, 125 nm, 100 nm, 75 nm, 50 nm, 25 nm or smaller upon reconstitution. In some embodiments, the pharmaceutical composition has a polydispersity index value of less than 1, 0.95, 0.9, 0.8, 0.75, 0.7, 0.6, 0.5, 0.4, 0.3, 0.25, 0.2, 0.1, 0.05 or less upon reconstitution. In some embodiments, the pharmaceutical composition has an average particle size of less than 500 nm, 400 nm, 300 nm, 200 nm, 175 nm, 150 nm, 125 nm, 100 nm, 75 nm, 50 nm, 25 nm or upon reconstitution.

In some embodiments, the lyophilized pharmaceutical composition further comprises one or more lyoprotectants, such as sucrose, trehalose, dextran or inulin. Typically, the lyoprotectant is sucrose. In some embodiments, the pharmaceutical composition is stable for at least 1 month or at least 6 months upon storage at 4° C., or for at least 6 months upon storage at 25° C. In some embodiments, the biologic activity of the mRNA of the reconstituted lyophilized pharmaceutical composition exceeds 75% of the biological activity observed prior to lyophilization of the composition.

Provided liposomes and compositions may be administered to any desired tissue. In some embodiments, the MUT mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered. Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

According to various embodiments, the timing of expression of delivered mRNAs can be tuned to suit a particular medical need. In some embodiments, the expression of the protein encoded by delivered mRNA is detectable 1, 2, 3, 6, 12, 24, 48, 72, 96 hours, 1 week, 2 weeks, or 1 month after administration of provided liposomes and/or compositions.

In some embodiments, a therapeutically effective dose of the provided composition, when administered regularly, results in a reduced methylmalonic acid level in a subject as compared to a baseline methylmalonic acid level before treatment.

In some embodiments, administering the provided composition results in an increased level of MUT protein in a liver cell (e.g., a hepatocyte) of a subject as compared to a baseline level before treatment. Typically, the baseline level is measured immediately before treatment. In some embodiments, administering the provided composition results in an increased MUT protein level in the liver cell by at least about 10%, 20%, 30%, 40%, 50%, 60%, 70%, 80%, 90%, or 95% as compared to a baseline level before treatment. In some embodiments, administering the provided composition results in an increased MUT protein level in a liver cell as compared to the MUT protein level a liver cell of subjects who are not treated.

In some embodiments, administering the provided composition results in an increased MUT protein level in plasma or serum of subject as compared to a baseline level before treatment. Typically, the baseline level is measured immediately before treatment. In some embodiments, administering the provided composition results in an increased MUT protein level in plasma or serum by at least about 10%, 20%, 30%, 40%, 50%, 60%, 70%, 80%, 90%, or 95% as compared to a baseline level before treatment. In some embodiments, administering the provided composition results in an increased MUT protein level in plasma or serum as compared to an MUT protein level in plasma or serum of subjects who are not treated.

In some embodiments, administering the provided composition results in increased MUT enzyme activity in a biological sample from a subject as compared to the baseline level before treatment. Typically, the baseline level is measured immediately before treatment. Biological samples include, for example, whole blood, serum, plasma, urine and tissue samples (e.g., liver). In some embodiments, administering the provided composition results in an increased MUT enzyme activity by at least about 10%, 20%, 30%, 40%, 50%, 60%, 70%, 80%, 90%, or 95% as compared to a baseline level immediately before treatment. In some embodiments, administering the provided composition results in an increased MUT enzyme activity as compared to MUT enzyme activity in subjects who are not treated.

In some embodiments the subject is a mammal. In some embodiments, the mammal is an adult. In some embodiments the mammal is an adolescent. In some embodiments the mammal is an infant or a young mammal. In some embodiments, the mammal is a primate. In some embodiments the mammal is a human. In some embodiments the subject is 6 years to 80 years old.

EXAMPLES

While certain compounds, compositions and methods of the present invention have been described with specificity in accordance with certain embodiments, the following examples serve only to illustrate the compounds of the invention and are not intended to limit the same.

Example 1. Exemplary Liposome Formulations for hMUT mRNA Delivery and Expression This example provides exemplary liposome formulations for effective delivery and expression of hMUT mRNA in vivo.

Lipid Materials

The formulations described in the following Examples, unless otherwise specified, contain a multi-component lipid mixture of varying ratios employing one or more cationic lipids, helper lipids (e.g., non-cationic lipids and/or cholesterol lipids) and PEGylated lipids designed to encapsulate human methylmalonyl-CoA mutase (hMUT) mRNA. Unless otherwise specified, the multi-component lipid mixture used in the following Examples were ethanolic solutions of cKK-E12 (cationic lipid), DOPE (non-cationic lipid), cholesterol and DMG-PEG2K.

Messenger RNA Material

Codon-optimized human methylmalonyl-CoA mutase (hMUT) messenger RNA was synthesized by in vitro transcription from a plasmid DNA template encoding the gene. Following in vitro transcription, a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A) tail were added. The poly(A) tail was approximately 800 nucleotides in length (SEQ ID NO:13), as determined by gel electrophoresis. The 5' and 3' untranslated regions present in each mRNA product are represented as X and Y, respectively, and defined as stated (vide infra).

```
Codon-Optimized Human Methylmalonyl-CoA mutase
(hMUT) mRNA:
X - Coding region - Y
5' and 3' UTR Sequences
                                        [SEQ ID NO.: 6]
X (5' UTR Sequence) =
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACG

                                        [SEQ ID NO.: 7]
Y (3' UTR Sequence) =
CGGGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCAUC

AAGCU
OR
```

-continued

```
                                        [SEQ ID NO.: 8]
GGGUGGCAUCCCUGUGACCCCUCCCCAGUGCCUCUCCUGGCCCUGGAAGU

UGCCACUCCAGUGCCCACCAGCCUUGUCCUAAUAAAAUUAAGUUGCAUCA

AAGCU
```

The MRT-1 codon-optimized hMUT messenger RNA coding region comprised:

```
                                        [SEQ ID NO: 4]
AUGCUUAGGGCAAAGAAUCAACUCUUUCUGCUGAGCCCACACUAUUUGCG

CCAGGUGAAAGAGAGCUCCGGCUCAAGGCUGAUCCAGCAGCGUCUUUUGC

AUCAGCAGCAGCCACUGCACCCGGAAUGGGCCGCUCUCGCGAAGAAGCAG

CUGAAGGGAAAGAACCCGGAAGAUCUGAUCUGGCACACUCCGGAGGGAAU

CUCAAUCAAGCCACUGUACUCUAAGAGAGACACCAUGGACCUUCCCGAAG

AACUGCCCGGGGUGAAGCCCUUCACCCGGGGACCGUACCCGACCAUGUAC

ACCUUUAGACCGUGGACGAUCCGCCAGUACGCAGGCUUCUCGACGGUCGA

AGAAAGCAACAAAUUCUAUAAAGACAACAUUAAGGCCGGACAACAGGGAC

UGUCCGUCGCAUUCGACCUCGCCACCCACCGCGGAUACGAUUCGGACAAU

CCAAGGGUGAGAGGUGACGUCGGAAUGGCCGGAGUGGCUAUUGAUACCGU

GGAGGACACGAAGAUCCUGUUCGACGGCAUCCCCUUGGAGAAGAUGUCCG

UGAGCAUGACUAUGAAUGGCGCUGUGAUUCCUGUGCUCGCCAACUUCAUC

GUGACCGGAGAGGAACAAGGCGUGCCGAAGGAAAAGCUCACUGGCACUAU

CCAAAACGACAUCCUCAAAGAAUUCAUGGUCCGCAACACUUACAUUUUUC

CUCCCGAACCUUCGAUGAAGAUCAUCGCCGAUAUCUUUGAGUACACGGCA

AAACACAUGCCGAAGUUCAAUUCGAUCUCGAUCUCCGGAUACCAUAUGCA

AGAGGCUGGGGCCGACGCGAUCCUCGAACUGGCUUACACCCUGGCCGACG

GACUGGAAUACUCACGCACUGGGCUGCAGGCCGGUCUGACCAUCGACGAG

UUCGCGCCGAGACUGUCCUUCUUCUGGGGCAUUGGUAUGAACUUCUACAU

GGAGAUCGCCAAAAUGCGAGCAGGCCGCAGGCUCUGGGCACACCUCAUCG

AGAAAAUGUUCCAGCCGAAGAAUUCUAAGUCGCUCCUGCUGCGCGCCCAC

UGCCAGACUAGCGGAUGGAGCUUGACUGAACAGGACCCGUACAACAAUAU

CGUGCGGACUGCCAUCGAAGCGAUGGCCGCAGUGUUCGGAGGAACCCAGU

CACUGCAUACCAACAGCUUUGACGAAGCCCUCGGCUUGCCAACUGUGAAA

AGCGCGCGGAUCGCAAGGAACACUCAGAUCAUUAUCCAAGAAGAAUCCGG

UAUCCCUAAGGUGGCCGAUCCGUGGGGCGGAUCCUACAUGAUGGAGUGCC

UGACCAAUGACGUCUACGAUGCCGCGCUGAAACUGAUCAACGAGAUUGAA

GAGAUGGGAGGAAUGGCUAAGGCCGUUGCAGAAGGGAUCCCGAAGCUGCG

GAUUGAGGAAUGUGCGGCCCGGCGCCAGGCCCGAAUCGAUAGCGGCUCAG

AAGUUAUCGUGGGUGUCAACAAGUACCAGCUUGAGAAGGAAGAUGCAGUG

GAGGUCCUCGCAAUUGAUAAUACCUCCGUCCGGAAUAGACAAAUCGAAAA

ACUGAAAAAGAUCAAGAGCUCCCGCGACCAAGCCCUGGCGGAAAGAUGCU

UGGCGGCCCUGACCGAGUGCGCUGCCUCAGGCGACGGAAACAUCCUGGCA

CUCGCAGUCGAUGCCUCGCGGGCGCGCUGCACUGUGGGUGAGAUCACCGA
```

-continued

CGCCCUCAAGAAGGUCUUUGGAGAGCAUAAGGCGAACGACAGAAUGGUGU

CGGGAGCAUACCGGCAGGAGUUCGGCGAAUCCAAAGAGAUCACUUCGGCG

AUCAAACGCGUGCACAAGUUCAUGGAACGGGAGGGGCGGCGGCCGCGCCU

UCUCGUGGCGAAGAUGGGGCAGGAUGGACAUGACCGCGGAGCUAAGGUGA

UCGCCACCGGGUUCGCUGAUCUCGGGUUCGACGUGGACAUCGGCCCUCUG

UUCCAAACCCCUAGAGAAGUGGCGCAACAAGCUGUGGAUGCUGAUGUGCA

UGCGGUCGGAAUCUCCACCCUCGCAGCCGGACAUAAAACUCUGGUGCCCG

AGCUCAUAAAGGAACUGAACUCGCUGGGCCGGCCAGAUAUCCUGGUCAUG

UGCGGUGGAGUGAUCCCACCUCAAGAUUACGAGUUCCUGUUUGAAGUCGG

AGUGUCAAACGUGUUUGGACCGGGAACUCGCAUCCCAAAGGCGGCCGUGC

AAGUCCUUGAUGACAUUGAAAAGUGUCUGGAGAAAAAGCAGCAGAGCGUG

UAG

The MRT-2 codon-optimized hMUT messenger RNA coding region comprised:

[SEQ ID NO: 5]

AUGCUGCGGGCCAAGAACCAGCUGUUCCUCCUUUCCCCCCACUACCUGAG

ACAAGUCAAAGAAUCCUCCGGAUCAAGAUUGAUUCAGCAACGCCUGUUGC

AUCAGCAACAGCCAUUGCACCCUGAAUGGGCCGCCCUGGCUAAGAAGCAG

CUUAAGGGAAAGAACCCGGAAGAUCUGAUCUGGCACACCCCGGAAGGCAU

CUCUAUCAAGCCUCUGUACUCCAAGAGAGACACCAUGGAUCUCCCUGAGG

AACUGCCGGGAGUCAAGCCUUUUACCCGCGGUCCGUACCCUACCAUGUAC

ACGUUCCGCCCGUGGACCAUCAGGCAGUACGCCGGAUUCAGCACGGUGGA

AGAGAGCAACAAGUUCUACAAGGACAACAUAAAGGCCGGACAGCAGGGAC

UGUCCGUGGCCUUCGACCUGGCCACCCAUCGGGGCUAUGACUCGGACAAC

CCUCGCGUGCGCGGGGAUGUCGGAAUGGCCGGAGUGGCGAUUGACACUGU

CGAGGACACUAAGAUCCUGUUCGAUGGCAUUCCCCUGGAAAAGAUGUCCG

UGAGCAUGACUAUGAACGGCGCAGUGAUCCCAGUGCUGGCUAACUUCAUC

GUGACUGGAGAGGAGCAAGGGGUGCCCAAAGAGAAGCUGACUGGAACUAU

CCAGAACGAUAUUCUGAAGGAGUUUAUGGUCCGGAACACUUACAUUUUCC

CGCCCGAGCCCUCGAUGAAGAUCAUCGCGGACAUUUUCGAGUACACCGCC

AAGCAUAUGCCUAAGUUCAACUCCAUCUCGAUCUCCGGAUACCACAUGCA

GGAAGCCGGAGCGGACGCGAUCCUUGAACUGGCGUACACUCUGGCCGAUG

GCCUGGAAUACUCCCGCACGGGCUUGCAGGCCGGUCUGACCAUCGACGAA

UUUGCCCCGCGGUUGUCCUUCUUUUGGGGAAUCGGCAUGAAUUUCUACAU

GGAAAUCGCCAAGAUGAGAGCGGGCCGGAGACUGUGGGCCCACCUGAUCG

AGAAGAUGUUCCAGCCCAAGAACUCGAAAAGCCUCCUCCUGCGGGCGCAC

UGCCAGACCUCCGGAUGGUCCCUGACCGAGCAGGACCCGUACAACAACAU

CGUCCGAACCGCUAUUGAGGCCAUGGCCGCCGUGUUUGGGGGAACUCAGU

CACUCCAUACUAAUUCCUUCGAUGAAGCCCUGGGGCUUCCUACCGUCAAG

AGCGCCCGGAUCGCCAGGAAUACCCAGAUCAUCAUUCAAGAAGAGUCAGG

-continued

CAUCCCUAAAGUGGCCGACCCCUGGGGGGGAAGCUACAUGAUGGAAUGUU

UGACCAACGACGUCUACGACGCCGCCCUGAAGCUCAUCAACGAAAUUGAA

GAAAUGGGCGGCAUGGCCAAGGCCGUGGCAGAGGGGAUCCCUAAGCUGCG

GAUUGAGGAAUGCGCCGCCAGACGCCAGGCCCGAAUCGACUCCGGUUCCG

AAGUCAUCGUGGGCGUGAACAAGUACCAGCUGGAGAAGGAAGAUGCCGUG

GAAGUGCUGGCCAUUGAUAACACCUCCGUGCGCAACCGCCAGAUCGAAAA

GCUGAAAAAGAUUAAGUCGUCGCGCGACCAGGCACUGGCGGAGAGAUGCC

UGGCUGCACUGACCGAGUGCGCGGCGUCUGGGGACGGCAAUAUCCUGGCA

CUGGCUGUGGACGCGAGCCGGGCCCGCUGCACUGUGGGAGAGAUCACUGA

UGCCCUCAAGAAAGUGUUCGGAGAACACAAGGCCAACGACAGAAUGGUGU

CGGGGGCCUAUCGCCAAGAAUUCGGGGAGUCGAAGGAAAUCACCAGCGCC

AUUAAGCGGGUGCACAAGUUCAUGGAAAGGGAAGGACGCCGGCCACGCCU

CCUGGUGGCAAAGAUGGGACAGGACGGUCACGACAGGGGCGCAAAGGUCA

UCGCGACCGGAUUCGCCGACCUCGGCUUCGAUGUGGACAUUGGACCCCUU

UUCCAAACCCCUCGGGAGGUCGCCCAACAAGCUGUGGAUGCCGACGUGCA

UGCUGUGGGAAUUUCGACCCUGGCCGCCGGUCACAAGACCCUGGUGCCCG

AACUGAUUAAGGAGCUGAACUCACUGGGAAGGCCUGAUAUUCUCGUGAUG

UGUGGCGGAGUGAUCCCGCCGCAAGACUACGAAUUCCUGUUCGAAGUCGG

CGUGUCCAACGUGUUCGGGCCCGGCACACGGAUCCCGAAAGCCGCGGUCC

AAGUGCUCGAUGAUAUUGAGAAGUGUCUCGAAAAGAAACAGCAGUCCGUC

UAG

MRT-0, wild type (non-codon-optimized) hMUT messenger RNA was also evaluated. The wild type hMUT messenger RNA coding region comprised:

[SEQ ID NO: 1]

AUGUUAAGAGCUAAGAAUCAGCUUUUUUUACUUUCACCUCAUUACCUGAG

GCAGGUAAAAGAAUCAUCAGGCUCCAGGCUCAUACAGCAACGACUUCUAC

ACCAGCAACAGCCCCUUCACCCAGAAUGGGCUGCCCUGGCUAAAAAGCAG

CUGAAAGGCAAAAACCCAGAAGACCUAAUAUGGCACACCCCGGAAGGGAU

CUCUAUAAAACCCUUGUAUUCCAAGAGAGAUACUAUGGACUUACCUGAAG

AACUUCCAGGAGUGAAGCCAUUCACACGUGGACCAUAUCCUACCAUGUAU

ACCUUUAGGCCCUGGACCAUCCGCCAGUAUGCUGGUUUUAGUACUGUGGA

AGAAAGCAAUAAGUUCUAUAAGGACAACAUUAAGGCUGGUCAGCAGGGAU

UAUCAGUUGCCUUUGAUCUGGCGACACAUCGUGGCUAUGAUUCAGACAAC

CCUCGAGUUCGUGGUGAUGUUGGAAUGGCUGGAGUUGCUAUUGACACUGU

GGAAGAUACCAAAAUUCUUUUUGAUGGAAUUCCUUUAGAAAAAAUGUCAG

UUUCCAUGACUAUGAAUGGAGCAGUUAUUCCAGUUCUUGCAAAUUUUAUA

GUAACUGGAGAAGAACAAGGUGUACCUAAAGAGAAGCUUACUGGUACCAU

CCAAAAUGAUAUACUAAAGGAAUUUAUGGUUCGAAAUACAUACAUUUUUC

CUCCAGAACCAUCCAUGAAAAUUAUUGCUGACAUAUUUGAAUAUACAGCA

AAGCACAUGCCAAAAUUUAAUUCAAUUUCAAUUAGUGGAUACCAUAUGCA

-continued

```
GGAAGCAGGGGCUGAUGCCAUUCUGGAGCUGGCCUAUACUUUAGCAGAUG

GAUUGGAGUACUCUAGAACUGGACUCCAGGCUGGCCUGACAAUUGAUGAA

UUUGCACCAAGGUUGUCUUUCUUCUGGGGAAUUGGAAUGAAUUUCUAUAU

GGAAAUAGCAAAGAUGAGAGCUGGUAGAAGACUCUGGGCUCACUUAAUAG

AGAAAAUGUUUCAGCCUAAAAACUCAAAAUCUCUUCUUCUAAGAGCACAC

UGUCAGACAUCUGGAUGGUCACUUACUGAGCAGGAUCCCUACAAUAAUAU

UGUCCGUACUGCAAUAGAAGCAAUGGCAGCAGUAUUUGGAGGGACUCAGU

CUUUGCACACAAAUUCUUUUGAUGAAGCUUUGGGUUUGCCAACUGUGAAA

AGUGCUCGAAUUGCCAGGAACACACAAAUCAUCAUUCAAGAAGAAUCUGG

GAUUCCCAAAGUGGCUGAUCCUUGGGGAGGUUCUUACAUGAUGGAAUGUC

UCACAAAUGAUGUUUAUGAUGCUGCUUUAAAGCUCAUUAAUGAAAUUGAA

GAAAUGGGUGGAAUGGCCAAAGCUGUAGCUGAGGGAAUACCUAAACUUCG

AAUUGAAGAAUGUGCUGCCCGAAGACAAGCUAGAAUAGAUUCUGGUUCUG

AAGUAAUUGUUGGAGUAAAUAAGUACCAGUUGGAAAAAGAAGACGCUGUA

GAAGUUCUGGCAAUUGAUAAUACUUCAGUGCGAAACAGGCAGAUUGAAAA

ACUUAAGAAGAUCAAAUCCAGCAGGGAUCAAGCUUUGGCUGAACGUUGUC

UUGCUGCACUAACCGAAUGUGCUGCUAGCGGAGAUGGAAAUAUCCUGGCU

CUUGCAGUGGAUGCAUCUCGGGCAAGAUGUACAGUGGGAGAAAUCACAGA

UGCCCUGAAAAAGGUAUUUGGUGAACAUAAAGCGAAUGAUCGAAUGGUGA

GUGGAGCAUAUCGCCAGGAAUUUGGAGAAAGUAAAGAGAUAACAUCUGCU

AUCAAGAGGGUUCAUAAAUUCAUGGAACGUGAAGGUCGCAGACCUCGUCU

UCUUGUAGCAAAAAUGGGACAAGAUGGCCAUGACAGAGGAGCAAAAGUUA

UUGCUACAGGAUUUGCUGAUCUUGGUUUUGAUGUGGACAUAGGCCCUCUU

UUCCAGACUCCUCGUGAAGUGGCCCAGCAGGCUGUGGAUGCGGAUGUGCA

UGCUGUGGGCAUAAGCACCCUCGCUGCUGGUCAUAAAACCCUAGUUCCUG

AACUCAUCAAAGAACUUAACUCCCUUGGACGGCCAGAUAUUCUUGUCAUG

UGUGGAGGGGUGAUACCACCUCAGGAUUAUGAAUUUCUGUUUGAAGUUGG

UGUUUCCAAUGUAUUUGGUCCUGGGACUCGAAUUCCAAAGGCUGCCGUUC

AGGUGCUUGAUGAUAUUGAGAAGUGUUUGGAAAAGAAGCAGCAAUCUGUA

UAA
```

The hMUT mRNAs used in Examples 2-6 are listed in table 2:

TABLE 2

| hMUT mRNAs | |
|---|---|
| mRNA | hMUT coding sequence of the encapsulated mRNA |
| MRT-1 | SEQ ID NO: 4 |
| MRT-2 | SEQ ID NO: 5 |
| MRT-0 | SEQ ID NO: 1 |

Formulation Protocol hMUT mRNA was encapsulated in multi-component liposomes as described in WO 2018/089801, published May 17, 2018 (incorporated herein by reference).

Example 2. Administration of hMUT mRNA-loaded Liposome Nanoparticles

This example illustrates exemplary methods of administering hMUT mRNA-loaded liposome nanoparticles and methods for analyzing delivered mRNA and subsequently expressed hMUT protein in liver tissue in vivo.

All studies were performed using male CD-1 mice, which were of approximately 7-9 weeks of age at the beginning of each experiment. The formulations were introduced by a single bolus tail-vein injection of an equivalent total dose of 1.0 mg/kg (unless otherwise specified) of encapsulated hMUT mRNA, which was prepared as described in Example 1. Mice were euthanized at 24 hours (±5%) post dose administration.

Isolation of Plasma for Analysis

All animals were euthanized by $CO_2$ asphyxiation at 24 hours (±5%) post dose administration (unless otherwise specified) followed by thoracotomy and terminal blood collection. Whole blood (maximal obtainable volume) was collected via cardiac puncture on euthanized animals and discarded. The animals were then and perfused with saline.

Isolation of Organ Tissues for Analysis

Following perfusion, the liver of each mouse was harvested, apportioned into separate aliquots and snap-frozen and stored at −70° C. for analysis.

Enzyme-Linked Immunosorbent Assay (ELISA) Analysis—MUT ELISA

Standard ELISA procedures were followed employing mouse monoclonal anti-MUT antibody (Sigma HPA1400171) as the capture antibody with rabbit anti-MUT polyclonal antibody (ProteinTech 17034-1-AP) as the secondary (detection) antibody. Horseradish peroxidase (HRP)-conjugated goat anti-rabbit IgG was used for activation of the 3,3',5,5'-tetramethylbenzidine (TMB) substrate solution. The reaction was quenched using 2N $H_2SO_4$ after 10 minutes. Detection was monitored via absorption (450 nm) on a Molecular Devices SpectraMax M5 instrument. Saline-treated mouse liver and recombinant human hMUT protein were used as negative and positive controls, respectively.

Liquid Chromatography-Mass Spectrometry (LC-MS) Analysis—hMUT LC/MS

The assay is performed on a targeted absolute protein quantification basis using Selected Reaction Monitoring (SRM). In a triple-quadruple (QQQ) mass spectrometer, SRM is a tandem selection process where selecting peptides by precursor m/z is followed by selecting fragmentations (transitions) of the targeted peptide. Furthermore, coupled with liquid chromatography and the addition of heavy labeled internal standards, SRM provided a highly selective, sensitive quantification of designated proteins.

To monitor and quantify proteins at peptide sequence levels, proteins in the mouse liver lysate were digested into peptides by LysC-Trypsin. Heavy Peptide Standards were added to the samples after digestion at known concentrations thus allowing the quantification of endogenous (light) peptides based on the heavy to light peptide ratio. Samples were analyzed by a reversed phased UPLC and QQQ triple quadruple mass spectrometer. Data analysis was performed using Mass Hunter Workstation Quantitative Analysis Software.

MUT Activity Assay

The quantitative method for methylmalonyl-CoA mutase (MCM) activity in mouse liver lysate and cell lysates measured succinyl-CoA (SC) production via the MCM-catalyzed conversion of methylmalonyl-CoA (MMC). Diluted liver lysate or cell lysate was incubated with the MCM cofactor adenosylcobalamin (AdoCbl). After the initial incubation period, MMC was spiked into the reaction tube. The reaction tubes were incubated for 10 minutes after which the reaction was stopped by the addition of trichloroacetic acid. SC in the samples was quantified by RP-HPLC with detection at 254 nm. The amount of SC produced in samples analyzed during one analysis session was used as a relative assessment of the amount of active MCM in the liver lysate.

Example 3. In Vivo Protein Production

This example demonstrates that administration of hMUT mRNA as described in Example 2 results in successful protein production in the mouse liver.

The mice were randomized into four groups for treatment with saline (control), MRT-1, MRT-2 or MRT-0 formulations.

In order to determine if the administered mRNA was successfully translated into protein in vivo, hMUT protein was quantified in the harvested mouse livers using hMUT LC/MS as described in Example 2 (FIG. 1 and Table 3).

TABLE 3

Quantification of methylmalonyl-CoA mutase production

| Formulation | Mean hMUT concentration (ng hMUT/mg total protein) |
|---|---|
| Saline | 0.0 ± 0.00 |
| MRT-1 | 152.9 ± 18.1 |
| MRT-2 | 76.44 ± 29.5 |
| MRT-0 | 56.16 ± 11.3 |

Production of hMUT protein was observed for mice treated with MRT-1, MRT-2 and MRT-0 (see FIG. 1). As expected, greater levels of protein production were observed following treatment with formulations comprising codon-optimized MUT mRNA (MRT-1 and MRT-2) than following treatment with formulations comprising wild type MUT mRNA (MRT-0). Surprisingly, the hMUT production level observed with MRT-1 was approximately double the protein production level observed with MRT-2.

This finding demonstrates that codon optimization, absent any modifications to the nucleotides used for in vitro translation of the mRNA, can result in a substantial (3-fold) increase of protein production over wild type mRNA in the target organ. Therefore, identification of an optimal codon-sequence may obviate the need for nucleotide modifications.

Example 4. In Vivo Protein Production and Enzymatic Activity

This example demonstrates that administration of hMUT mRNA results in supraphysiological increase in MUT protein activity in mice livers. The amount of MUT protein correlates with its enzymatic activity.

Sixteen mice were randomized into four groups for treatment with saline or with 0.2 mg/kg, 0.5 mg/kg or 1.0 mg/kg dose equivalent of the MRT-1 mRNA formulation. The mRNA was prepared as described in Example 1. MRT-1 was chosen for this experiment because of it superior levels of expression as demonstrated in Example 3. The mice were euthanized at 24 hours post administration and their livers processed as described in Example 2.

In order to determine if delivered mRNA was successfully translated into protein in vivo, hMUT protein was quantified in the harvested mouse livers using hMUT ELISA as described in Example 2. Activity of the expressed hMUT protein was determined using the activity assay described in Example 2.

Figure 2B:
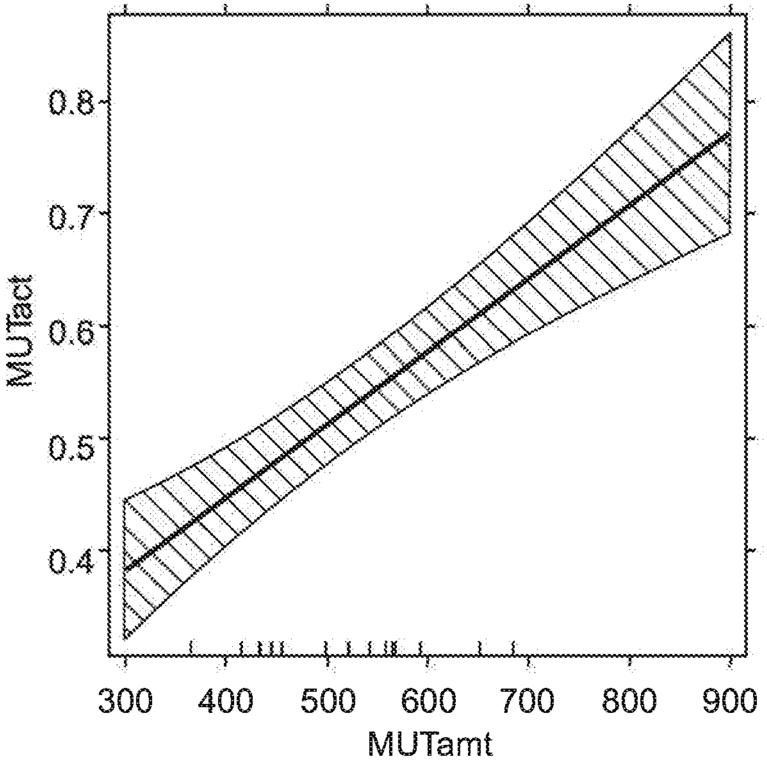
FIG. 2B shows the correlation between MUT activity (MUTact) and the amount of MUT protein as determined by ELISA (MUTamt) in mouse livers following administration of an MRT-1 formulation.

In FIG. 2, MUT protein concentration/activity observed in the MRT-1-treated mice is shown as a percentage of the protein concentration/activity for saline-treated mice. A supraphysiological increase in MUT protein concentration and MUT enzymatic activity was observed for all doses tested. The increase was dose-dependent and linear for the amounts of mRNA tested. There was a good correlation between the amount of hMUT protein detected by ELISA and the activity detected by reverse phase (RP)-HPLC of the hMUT substrate (see FIG. 2*b*).

Example 5. Pharmacokinetic Study of Expressed hMUT Protein

This example demonstrates that hMUT protein at therapeutic levels can be maintained for several days following a single bolus tail-vein injection of encapsulated hMUT mRNA. The data also indicate that once-weekly dosing, or longer dosing, of encapsulated mRNA is feasible to maintain adequate therapeutic levels of hMUT.

In this study, 45 mice were randomized into nine treatment groups. Groups 1-8 were treated with 1.0 mg/kg MRT-1. Group 9 were treated with saline. Treatment groups 1-9 were euthanized at different time points, as shown in Table 4:

TABLE 4

Pharmacokinetic study design

| Group No. | No. of Animals | Test Article | Dose Levels (mg/kg) | Conc. (mg/mL) | Dose Volume (mL/kg) | Dosing Regimen ROA | Terminal Time Point |
|---|---|---|---|---|---|---|---|
| 1 | 5 | MRT-1 | 1.0 | 0.2 | 5 | Once on Day 1 via IV injection | At 6 hours post dose administration |
| 2 | 5 | MRT-1 | 1.0 | 0.2 | | | At 12 hours post dose administration |
| 3 | 5 | MRT-1 | 1.0 | 0.2 | | | At 24 hours post dose administration |
| 4 | 5 | MRT-1 | 1.0 | 0.2 | | | At 48 hours post dose administration |

TABLE 4-continued

| Pharmacokinetic study design | | | | | | | |
|---|---|---|---|---|---|---|---|
| Group No. | No. of Animals | Test Article | Dose Levels (mg/kg) | Conc. (mg/mL) | Dose Volume (mL/kg) | Dosing Regimen ROA | Terminal Time Point |
| 5 | 5 | MRT-1 | 1.0 | 0.2 | | | At 72 hours post dose administration |
| 6 | 5 | MRT-1 | 1.0 | 0.2 | | | At 96 hours post dose administration |
| 7 | 5 | MRT-1 | 1.0 | 0.2 | | | At 7 days post dose administration |
| 8 | 5 | MRT-1 | 1.0 | 0.2 | | | At 10 days post dose administration |
| 9 | 5 | NT | NA | NA | NA | NA | At 10 days post dose administration |

MUT protein activity was quantified in treated mouse livers following euthanization using the assay described in Example 2.

FIG. 3 shows hMUT expression per mg of total protein in mouse at various timepoints after administration of a 1.0 mg/kg dose of an MRT-1 formulation, plotted in two different formats. As indicated in FIG. 3, MUT protein was observed in the MRT-1-treated mice for out to Day 8 (7 days post dose administration). The dotted line in FIG. 3 corresponds to the approximate MUT protein level that results in methylmalonic acid normalization in a known MMA disease model (see An et al. (2017, Cell Reports 21, 3548-3558), in particular FIG. 6 and accompanying description of FIG. 6), suggesting that the MRT-1 formulation is capable of providing a therapeutic amount of MUT protein for at least 7 days post dose administration.

Example 6. Dose Response Study

This example demonstrates that administration of increasing doses of hMUT mRNA results in dose-dependent production of hMUT protein in mice livers 24 hours after a single bolus tail-vein injection of encapsulated hMUT mRNA.

In one study, CD-1 mice were randomized into groups for treatment with saline or with 0.1 mg/kg, 0.25 mg/kg or 0.5 mg/kg dose equivalent of the MRT-1 formulation, as indicated in Table 5. In a separate study, CD-1 mice were randomized into groups for treatment with saline or with 1.0 mg/kg dose equivalent of the MRT-1 formulation, as indicated in Table 5.

TABLE 5

| Dose response study design | | | | | | | |
|---|---|---|---|---|---|---|---|
| Group No. | No. of Animals | Test Article | Dose Levels (mg/kg) | Conc. (mg/mL) | Dose Volume (mL/kg) | Dosing Regimen ROA | Terminal Time Point |
| 1 | 5 | MRT-1 | 0.5 | 0.1 | 5 | Once on Day 1 | At 24 hours post |
| 2 | 5 | MRT-1 | 0.25 | 0.05 | | via IV | dose |
| 3 | 5 | MRT-1 | 0.1 | 0.02 | | injection | administration |
| 4 | 5 | MRT-1 | 1.0 | 0.2 | | | |
| 5 | 5 | NT | NA | NA | NA | NA | On Day 2 |

In order to determine if delivered mRNA was successfully translated into protein in vivo, MUT protein was quantified in treated mouse livers 24 hours after administration using the assay described in Example 2.

Figure 6:
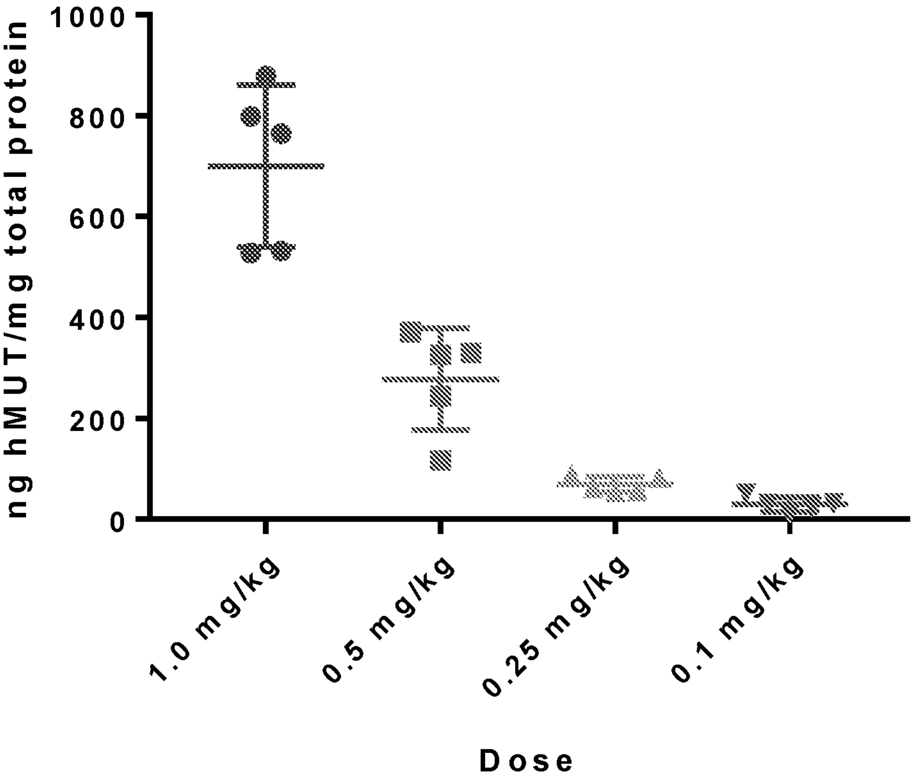
FIG. 6 shows the dose response for hMUT expression in the liver for animals treated with a single dose of 0.1-1.0 mg/kg liposome-encapsulated MUT mRNA.

The results are shown in FIG. 6. A dose-dependent increase in hMUT protein expression was observed over the full range of doses tested.

Example 7. Reduction in Plasma MMA Following Administration of hMUT mRNA in a Liposome This example demonstrates that administration of hMUT mRNA in a liposome provides reduction in plasma MMA for an extended duration.

In the study, twelve hMUT G715V mice (hypomorphic mouse model of MMA), 2-4 months of age, were randomized into four groups (n=3 for each group) for administration (on Day 1) via tail vein injection with either saline or 0.03 mg/kg, 0.1 mg/kg or 0.3 mg/kg of the liposome-encapsulated MRT-1 formulation as described in Example 1.

G715V mice show a reduced but not complete loss of Mut activity in the liver and moderately increased plasma MMA levels. This is similar to patients with the Mut p. G717V mutation (An et al. (2017, Cell Reports 21, 3548-3558); Senec et al. (2013, Mol. Ther. 2/(Suppl 1), S107)). G715V mice provide a model for patients suffering from mild MMA.

Figure 4:
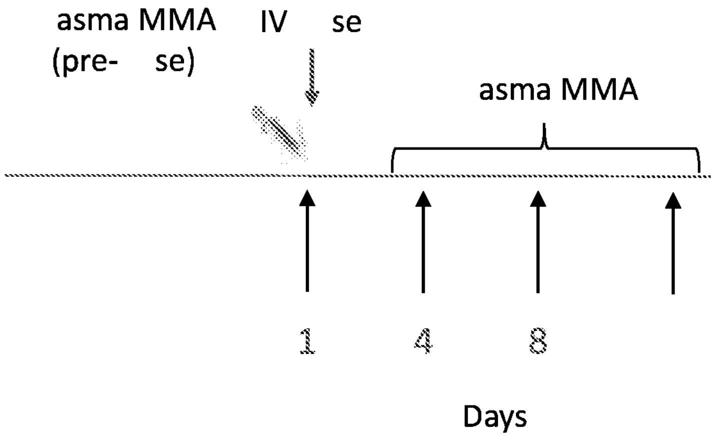
FIG. 4 shows the study design for the study described in Example 7.

Whole blood was collected from each animal pre-dose (on Day 1) and at each of Day 4, Day 8 and Day 11 (i.e., 3 days, 7 days and 10 days following administration of the saline or liposome-encapsulated MRT-1 formulation). The whole blood samples were processed to plasma and MMA in plasma was quantified by LC/MS. The overall study design is further depicted in FIG. 4 and in Table 6 below.

TABLE 6

| MMA reduction study design | | | | | | | |
|---|---|---|---|---|---|---|---|
| Group No. | No. of Animals | Test Article | Dose Levels (mg/kg) | Conc. (mg/mL) | Dose Volume (mL/kg) | Dosing Regimen ROA | Sample Collection Times |
| 1 | 3 | Saline | 0.0 | 0.0 | 5 | Once on | Pre-dose (Day |
| 2 | 3 | MRT-1 | 0.03 | 0.006 | | Day 1 | 1), 4, 8, 11 |
| 3 | 3 | MRT-1 | 0.1 | 0.02 | | via IV | days |
| 4 | 3 | MRT-1 | 0.3 | 0.06 | | injection | |
| | | | | | | NA | |

The liposome formulation for all doses was prepared in the same way, as described in Example 1. Specifically, the liposome formulation included a cationic lipid, a non-cationic lipid, cholesterol and a PEGylated lipid. The liposome included these four lipid components at a ratio of 40:30:25:5 (cationic lipid:non-cationic lipid:cholesterol:PEGylated lipid). The cationic used in the liposome was cKK-E12. The non-cationic used in the formulation was DOPE. The PEGylated lipid used in the formulation DMG-PEG. The encapsulated liposomes were prepared by first forming the liposomes in the absence of mRNA, by mixing the four components (cationic lipid, non-cationic lipid, cholesterol, PEGylated lipid, together in a citrate buffer. Then, in a second step, the formed, empty liposomes were mixed with the mRNA encoding MUT to encapsulate the mRNA. Further information about this process is described in WO2018/089801. The resulting liposome-encapsulated MUT mRNA had an N/P ratio equal to 2. The percent of mRNA encapsulation in liposome-encapsulated MUT mRNA was greater than 65%. The average diameter of the liposome-encapsulated MUT mRNA was less than 130 nm. The polydispersity of the liposome-encapsulated mRNA was less than 0.25.

Plasma MMA was measured at Day 1 (pre-dose measurement) and at Day 4 (3 days following dosing), Day 8 (7 days following dosing), and Day 11 (10 days following dosing), in order to determine if the administered liposome-encapsulated MUT mRNA was successful in translating MUT protein in vivo at quantities to reduce MMA substrate for extended periods. Briefly, plasma MMA was extracted using liquid-liquid extraction, followed by liquid chromatographic separation and mass spec (MS/MS) analysis.

Results of this study are provided in Table 7 below and in FIGS. 5A-5D.

| % Reduction in Plasma MMA Compared to Day 1 Pre-Dose | | | | | |
|---|---|---|---|---|---|
| Treatment | Mouse # | Day 1 | Day 4 | Day 8 | Day 11 |
| Saline | M1 | 0.00 | 42.25 | −16.85 | −89.89 |
| | M2 | 0.00 | 55.03 | −20.61 | 38.18 |
| | M3 | 0.00 | −5.00 | −20.71 | −68.57 |
| 0.03 mg/kg | M4 | 0.00 | 70.23 | 43.51 | −24.14 |
| | M5 | 0.00 | 79.58 | −2.82 | −36.62 |
| | M6 | 0.00 | 63.10 | 0.00 | −61.21 |
| 0.1 mg/kg | M7 | 0.00 | 94.98 | 83.48 | 56.87 |
| | M8 | 0.00 | 90.34 | 51.92 | 9.85 |
| | M9 | 0.00 | 94.10 | 57.82 | 70.98 |
| 0.3 mg/kg | M10 | 0.00 | 89.03 | 88.74 | 72.91 |
| | M11 | 0.00 | 84.79 | 84.26 | 66.26 |
| | M12 | 0.00 | 93.28 | 88.19 | 78.78 |

Figure 5A:
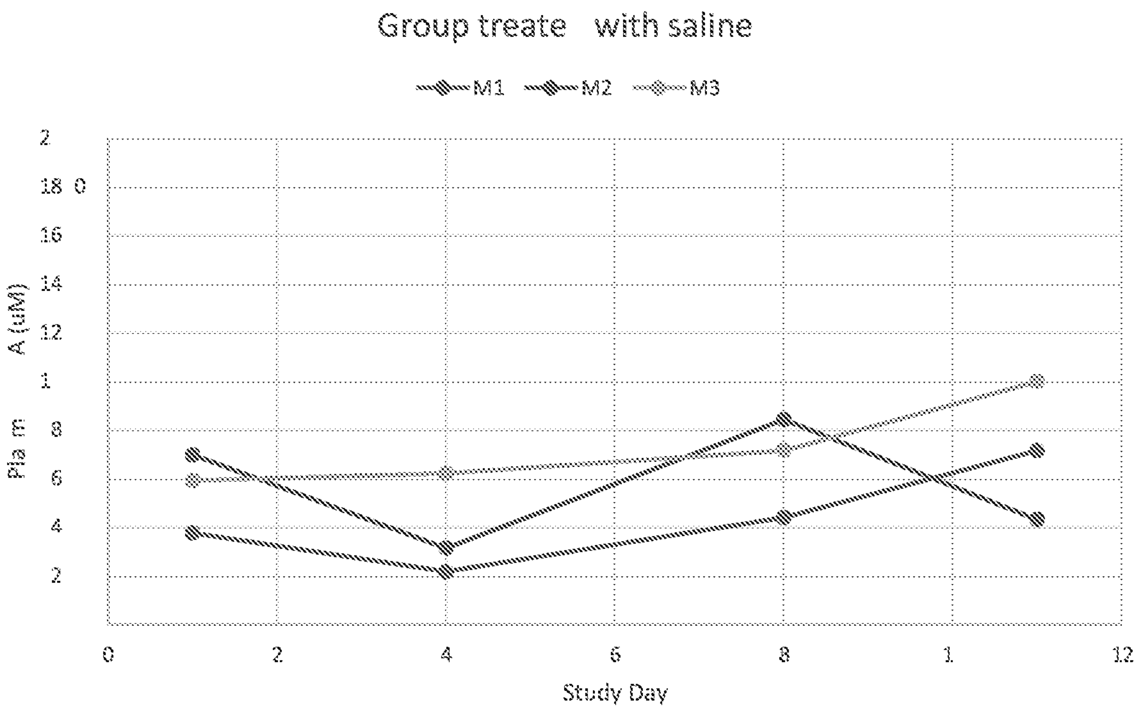
FIG. 5A shows plasma MMA levels over time for mild MMA mouse models treated with saline as a control group, with no substantial change in plasma MMA levels observed in the animals.
Figure 5B:
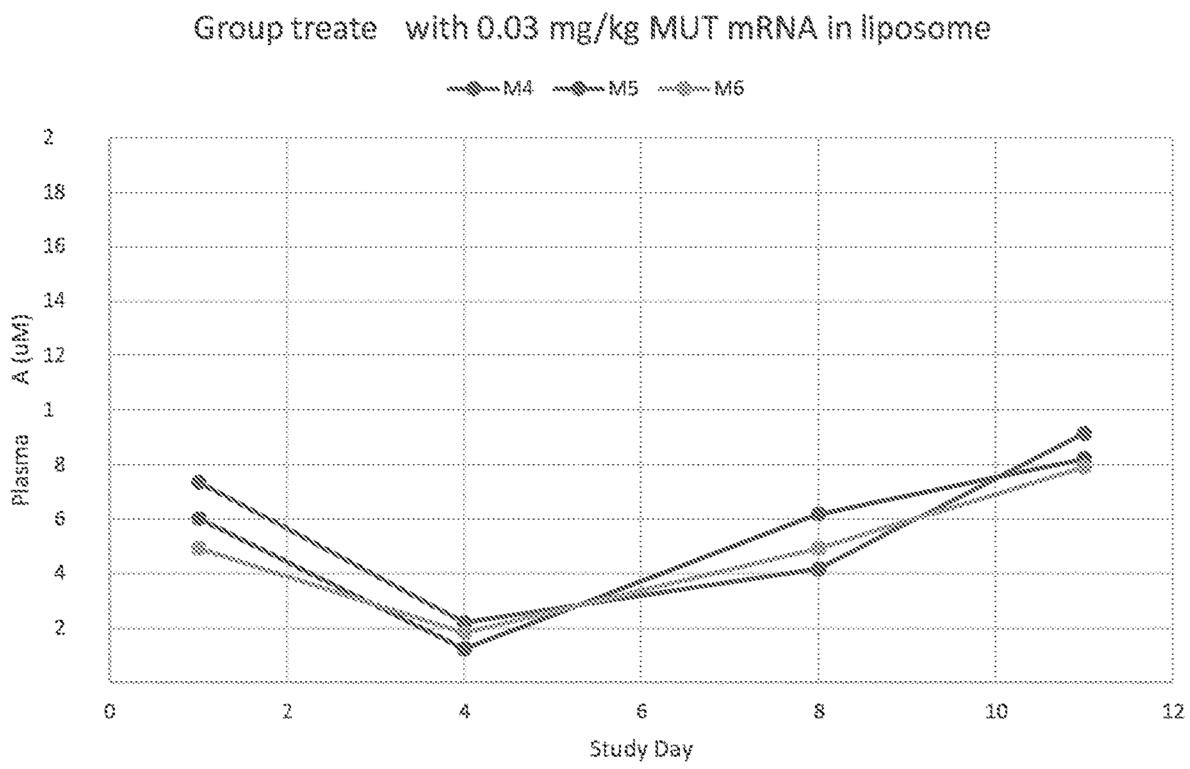
FIG. 5B shows plasma MMA levels over time for mild MMA mouse models treated with a single dose of 0.03 mg/kg liposome-encapsulated MUT mRNA, with 60% or greater reduction in plasma MMA observed for at least 3 days post-dose (Day 4) as compared to plasma MMA prior to dosing, for all animals tested.

As shown in Table 7, all doses of liposome-encapsulated MUT mRNA tested provided 60% or greater reduction in plasma MMA for at least 72 hours post-dose as compared to plasma MMA prior to dosing. As shown in FIG. 5A, the saline control group showed no substantial change in plasma MMA levels. In FIG. 5A, individual animals are identified as M1, M2 and M3, respectively. However, as shown in FIG. 5B and in Table 7, for animals treated with a single dose of 0.03 mg/kg liposome-encapsulated MUT mRNA, the treatment provided 60% or greater reduction in plasma MMA to all animals for at least 3 days post-dose as compared to plasma MMA prior to dosing. In FIG. 5B, individual animals are identified as M4, M5 and M6, respectively.

Figure 5C:
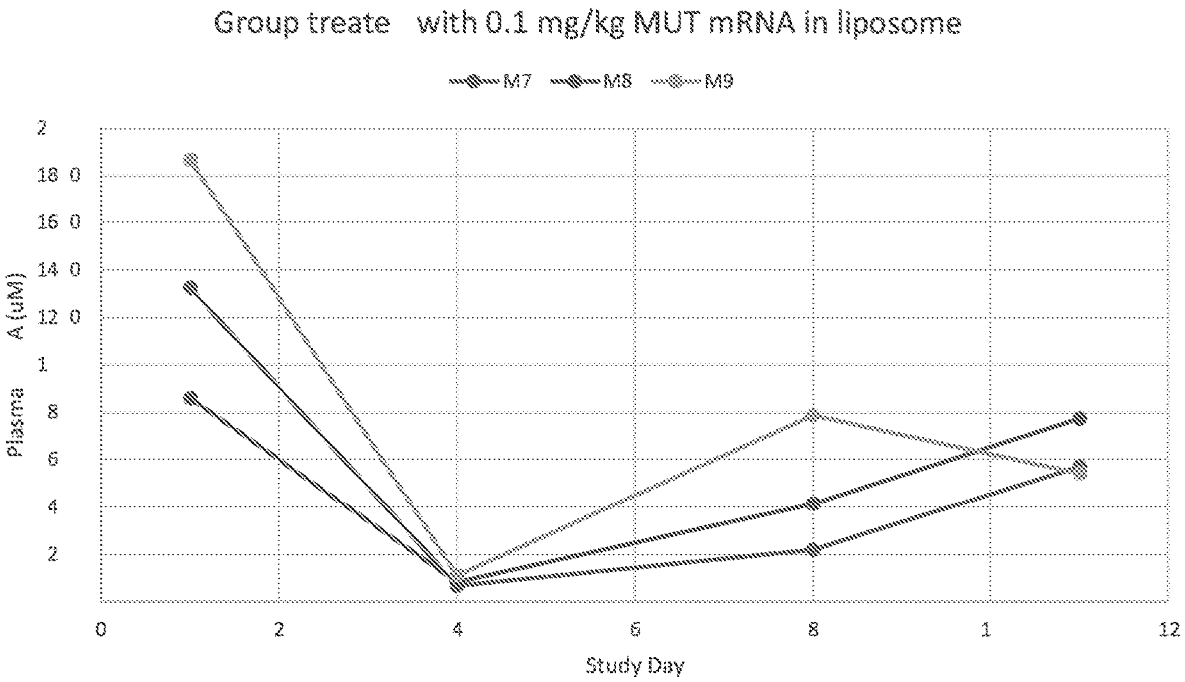
FIG. 5C shows plasma MMA levels over time for mild MMA mouse models treated with a single dose of 0.1 mg/kg liposome-encapsulated MUT mRNA, with a 50% or greater reduction in plasma MMA observed for at least 10 days post-dose (Day 11) as compared to plasma MMA prior to dosing, for two of the three animals tested.

As shown in FIG. 5C, for animals treated with a single dose of 0.1 mg/kg liposome-encapsulated MUT mRNA, the treatment provided 90% or greater reduction in plasma MMA to all animals for at least 3 days post-dose as compared to plasma MMA prior to dosing. Moreover, for the 0.1 mg/kg treatment group, all animals maintained a 50% or greater reduction in plasma MMA for at least 7 days post-dose as compared to plasma MMA prior to dosing. Even at 10 days post dose, 2 of the 3 animals treated with 0.1 mg/kg liposome-encapsulated MUT mRNA maintained a 50% or greater reduction in plasma MMA as compared to plasma MMA prior to dosing. In FIG. 5C, individual animals are identified as M7, M8 and M9, respectively.

Figure 5D:
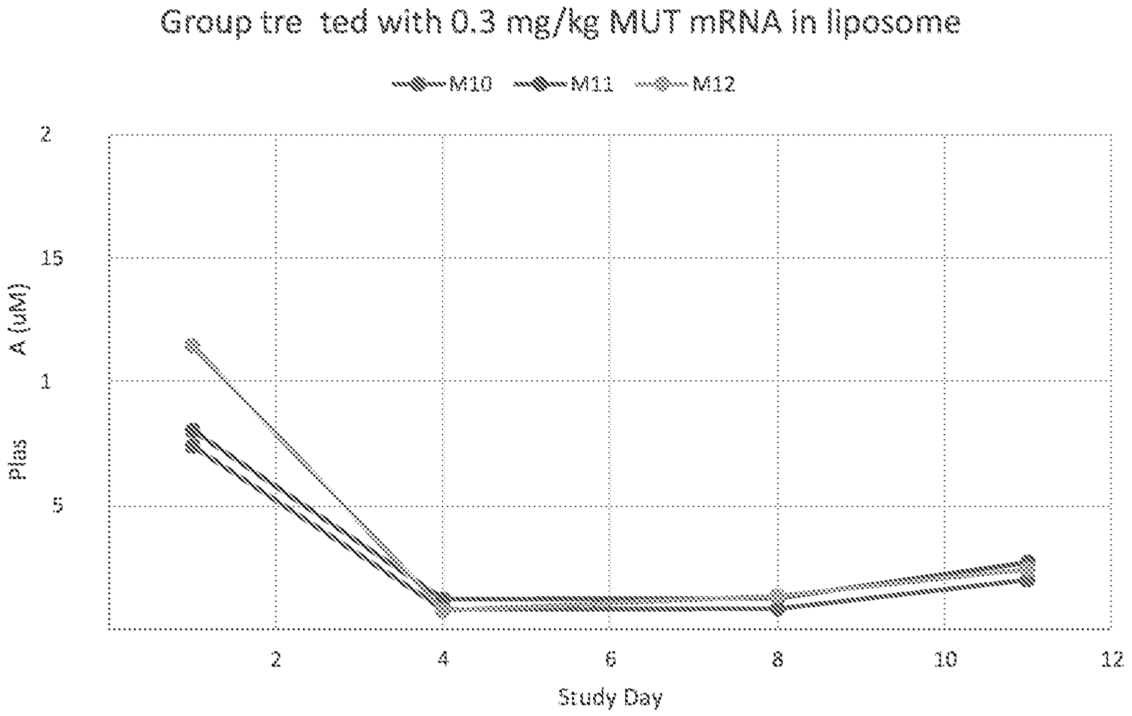
FIG. 5D shows plasma MMA levels for mild MMA mouse models treated with a single dose of 0.3 mg/kg liposome-encapsulated MUT mRNA, with a 65% or greater reduction in plasma MMA observed for at least 10 days post-dose (Day 11) as compared to plasma MMA prior to dosing, for all animals tested.

As shown in FIG. 5D, for animals treated with a single dose of 0.3 mg/kg liposome-encapsulated MUT mRNA, the treatment provided 80% or greater reduction in plasma MMA to all animals for at least 3 days post-dose as compared to plasma MMA prior to dosing. Moreover, for the 0.3 mg/kg treatment group, all animals maintained the 80% or greater reduction in plasma MMA for at least 7 days post-dose as compared to plasma MMA prior to dosing. Even at 10 days post dose, all animals treated with 0.3 mg/kg liposome-encapsulated MUT mRNA maintained a 65% or greater reduction in plasma MMA as compared to plasma MMA prior to dosing. In FIG. 5D, individual animals are identified as M10, M11 and M12, respectively.

These data illustrate that the methods and compositions used herein provide a potent treatment for reducing MMA levels in animals and subjects unable to reduce MMA otherwise.

Example 8. Reduction in Plasma MMA Following Administration of hMUT mRNA in a Liposome-Study Continuation This example demonstrates that repeated administration of hMUT mRNA in a liposome continues to provide reduction in plasma MMA for an extended duration.

The study described in example 7 was continued, with further doses of either 0.1 mg/kg or 0.3 mg/kg of the liposome-encapsulated MRT-1 formulation administered every two weeks (on days 15, 29, 43, 57, 71 and 84). Plasma MMA levels were measured 5 and 10 days after each dose by LC-MS analysis, as described in example 7. The results of this extended dosing study are provided in FIG. 7 (five days post dose) and 8 (ten days post dose). In some of the test animals, repeated dosing resulted in damage to the tail veins, resulting in some doses being administered only partially. Animals with collapsed tail veins were removed from the study. The damage did not appear to be associated with the test article and therefore it is not expected that repeated administration will result in similar problems in human subjects. Based on visual examination of the test animals, repeated administration was otherwise well-tolerated.

Figure 7:
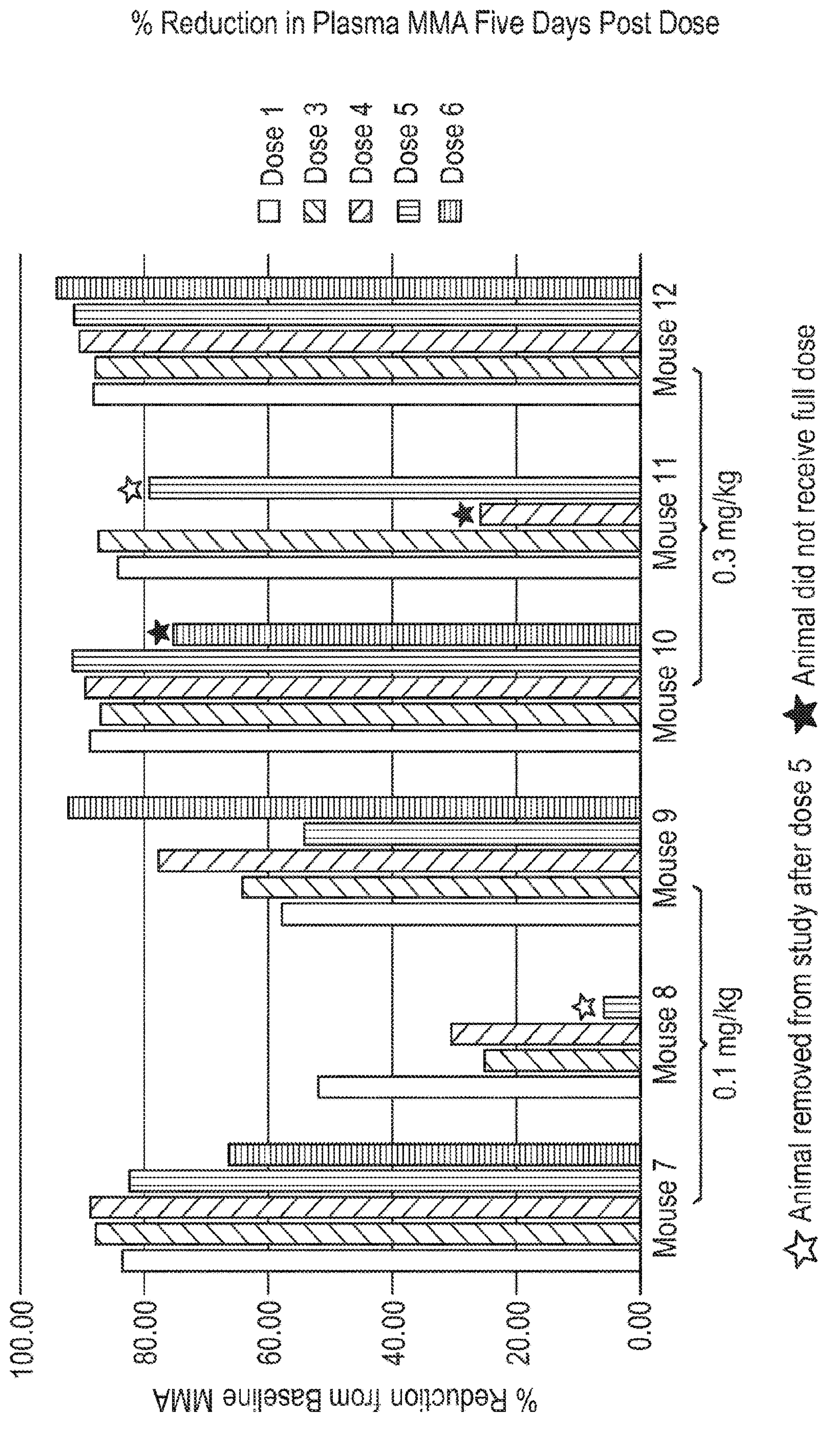
FIG. 7 shows plasma MMA levels at 5 days post-dose relative to individual animal baseline plasma MMA levels for mild MMA mouse models treated with repeated doses of 0.1 mg/kg or 0.3 mg/kg liposome-encapsulated MUT mRNA.

Repeated administration of 0.1 mg/kg and 0.3 mg/kg doses of liposome-encapsulated MUT mRNA maintained a 50% to 90% reduction of MMA plasma levels from baseline 5 days post administration (see FIG. 7). Greater variability between time points was observed for the group of mice receiving the 0.1 mg/kg dose, whereas repeated administration of 0.3 mg/kg consistently achieved an at least 80% reduction of MMA plasma levels from baseline.

Figure 8:
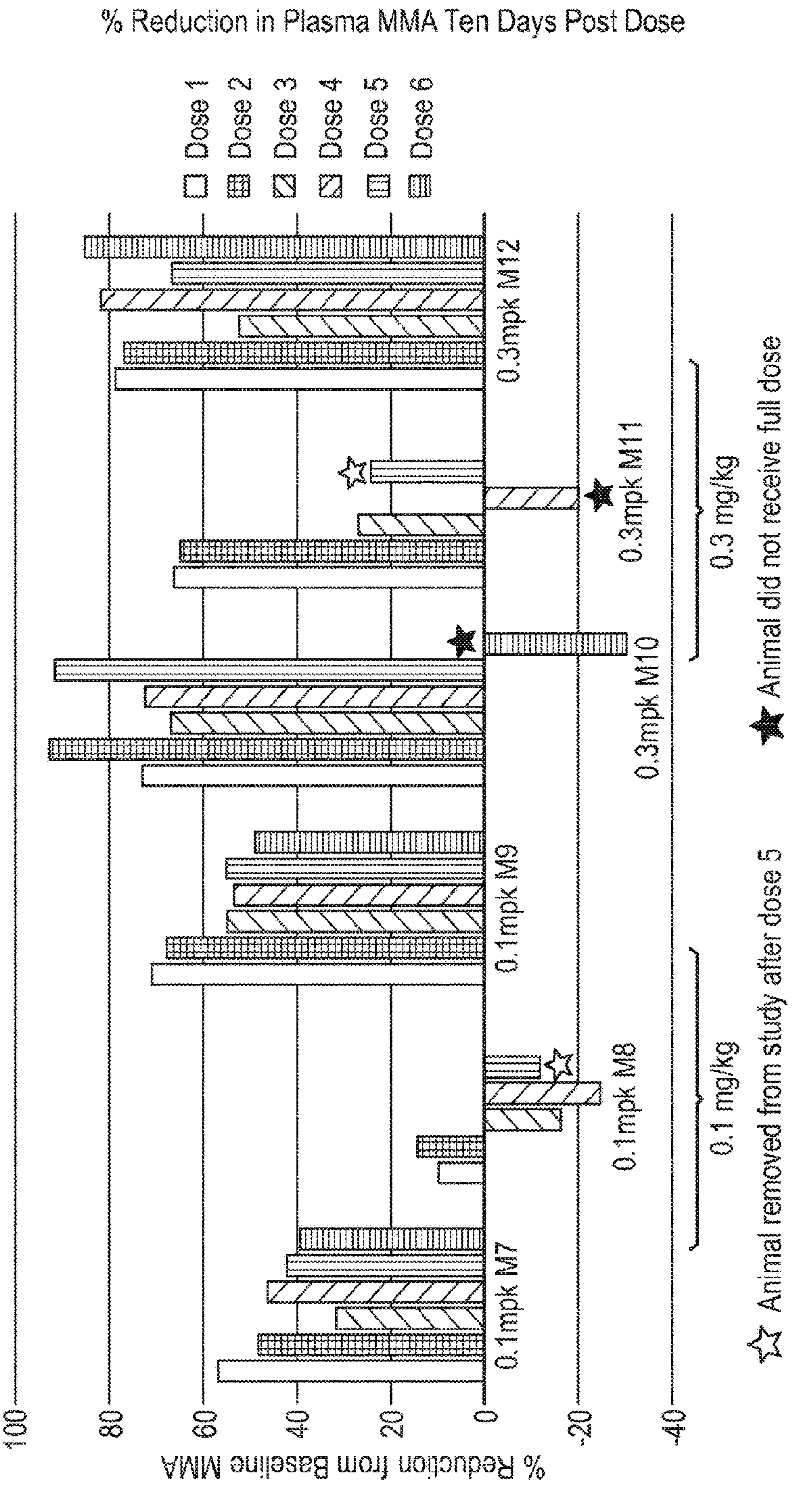
FIG. 8 shows plasma MMA levels at 10 days post-dose relative to individual animal baseline plasma MMA levels for mild MMA mouse models treated with repeated doses of 0.1 mg/kg or 0.3 mg/kg liposome-encapsulated MUT mRNA.

Reduced MMA plasma levels were maintained even after 10 days. In particular, successfully dosed animals in the 0.3 mg/kg dose group maintained about 50% to 90% reduction of MMA plasma levels 10 days post administration, although greater variation was observed between doses (see FIG. 8). Even for the 0.3 mg/kg dose group, MMA plasma levels were about 30% to 70% reduced relative to baseline 10 days post administration if continuous dosing throughout the study period had been achieved.

These data show that the reduction in plasma MMA levels following a single dose of liposome-encapsulated MRT-1 formulation observed in example 7 can be maintained for multiple doses administered at 2 week intervals. The data of this example therefore further illustrate that the methods and compositions used herein provide a potent treatment for reducing MMA levels in animals and subjects unable to reduce MMA otherwise. The data indicate that administration of liposome-encapsulated hMUT mRNA every two weeks may be sufficient to effectively reduce MMA plasma levels, in particular in patients suffering from mild MMA.

Example 9. Reduction in Plasma MMA Following Administration of hMUT mRNA in a Liposome-Study Continuation This example demonstrates that administration of hMUT mRNA in a liposome provides reduction in plasma MMA for an extended duration in an animal model for severe MMA.

Specifically, in this study, 3 $MUV^{-/-}$; $Tg^{INS\text{-}Mck\text{-}MUT}$ mice (lethal $MUT^{-/-}$ phenotype rescued by skeletal muscle expression of a germline transgene), 8-10 weeks of age, were administered with liposome-encapsulated MRT-1 formulation as described in Example 7 at a dose of 0.3 mg/kg via tail vein injection. Whole blood was collected from each animal pre-dose (on Day 1) and at each of Day 8 and Day 15 (i.e., 7 days and 14 days following administration of the saline or liposome-encapsulated MRT-1 formulation). The whole blood samples were processed to plasma and MMA in plasma was quantified by LC/MS, as described in example 7.

Figure 9:
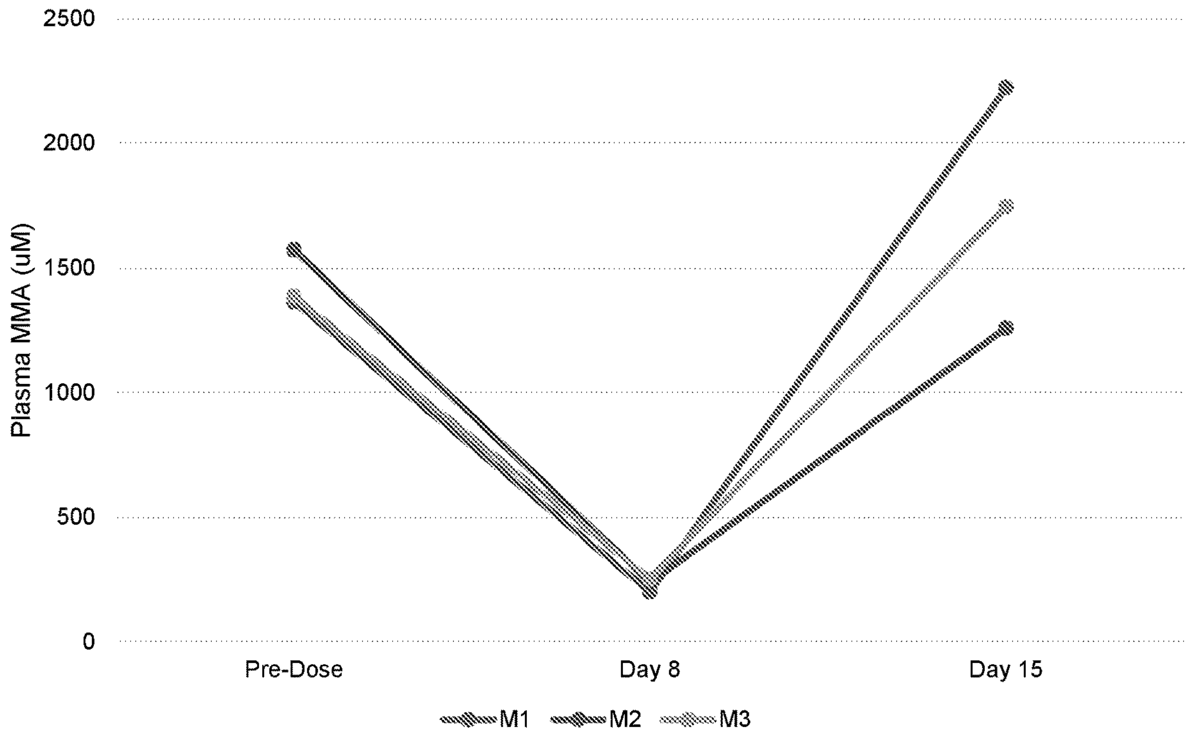
FIG. 9 shows plasma MMA concentration at 7 and 14 days post-dose for severe MMA mouse models treated with a single dose of 0.3 mg/mg liposome-encapsulated MUT mRNA.

The results are provided in FIG. 9. An 84% or greater reduction in plasma MMA was observed at 7 days following administration of the liposome-encapsulated MRT-1 formulation for all animals. These data illustrate that the methods and compositions used herein provide a potent treatment for reducing MMA levels in animals and subjects with severe MMA phenotypes. In particular, they indicate that repeated weekly administration of liposome-encapsulated hMUT mRNA may be sufficient to effectively reduce MMA plasma levels.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of treating methylmalonic acidemia (MMA) in a subject in need thereof, the method comprising intravenously administering to the subject a composition comprising an mRNA comprising a codon-optimized methylmalonyl-CoA mutase (MUT) coding sequence, wherein the mRNA is administered such that MUT expression is detected in the liver, wherein the mRNA is encapsulated within a liposome that comprises one or more cationic lipids, one or more non-cationic lipids, one or more cholesterol-based lipids and one or more PEG-modified lipids, wherein the nucleotides of the mRNA are unmodified, wherein the codon-optimized MUT coding sequence comprises the nucleotide sequence as set forth in SEQ ID NO: 4, and wherein the mRNA comprises a 3' poly(A) tail sequence that is 300-800 nucleotides long, thereby treating MMA in the subject.

2. The method of claim 1, wherein the ratio of cationic lipids: non-cationic lipids: cholesterol lipids: PEGylated lipids is approximately 40:30:20:10 by molar ratio, or approximately 40:30:25:5 by molar ratio, or approximately 40:32:25:3 by molar ratio, or approximately 50:25:20:5 by molar ratio.

3. The method of claim 1, wherein the liposome has a size of about 80 nm to 200 nm.

4. The method of claim 1, wherein the mRNA is administered at a dose ranging from about 0.03-3.0 mg/kg body weight.

5. The method of claim 1, wherein the composition is administered once a week, or once every two weeks, or twice a month, or once a month.

6. The method of claim 1, wherein the administering of the composition results in MUT expression in the liver at or above about 100 ng/mg of total protein.

7. The method of claim 1, wherein the administering of the composition results in a decreased levels of methylmalonic acid level in plasma and/or urine as compared to the baseline methylmalonic acid level before the treatment.

8. The method of claim 1, wherein the mRNA comprises the 3' poly(A) tail nucleotide sequence that is 300 nucleotides long.

9. The method of claim 1, wherein the mRNA comprises the 3' poly(A) tail nucleotide sequence that is 800 nucleotides long.

10. A method of treating methylmalonic acidemia (MMA) in a subject in need thereof, the method comprising intravenously administering to the subject a composition comprising an mRNA comprising a codon-optimized methylmalonyl-CoA mutase (MUT) coding sequence, wherein the mRNA is administered such that MUT expression is detected in the liver, wherein the mRNA is encapsulated within a liposome that comprises one or more cationic lipids, one or more non-cationic lipids, one or more cholesterol-based lipids and one or more PEG-modified lipids, wherein the nucleotides of the mRNA are unmodified, wherein the codon-optimized MUT coding sequence comprises the nucleotide sequence as set forth in SEQ ID NO: 5, and wherein the mRNA comprises a 3' poly(A) tail that is 300-800 nucleotides long, thereby treating MMA in the subject.

11. The method of claim 10, wherein the 3' poly(A) tail nucleotide sequence is 300 nucleotides long.

12. The method of claim 10, wherein the 3' poly(A) tail nucleotide sequence is 800 nucleotides long.

13. The method of claim 10, wherein the ratio of cationic lipids: non-cationic lipids: cholesterol lipids: PEGylated lipids is approximately 40:30:20:10 by molar ratio, or approximately 40:30:25:5 by molar ratio, or approximately 40:32:25:3 by molar ratio, or approximately 50:25:20:5 by molar ratio.

14. The method of claim 10, wherein the mRNA is administered at a dose ranging from about 0.03-3.0 mg/kg body weight.

* * * * *